US011851470B2

(12) United States Patent
Riazifar et al.

(10) Patent No.: US 11,851,470 B2
(45) Date of Patent: Dec. 26, 2023

(54) PLATFORMS, COMPOSITIONS, AND METHODS FOR THERAPEUTIC DELIVERY

(71) Applicant: Entelexo Biotherapeutics, Inc., Irvine, CA (US)

(72) Inventors: Milad Riazifar, Irvine, CA (US); Charles Cameron Taylor, Long Beach, CA (US); Todd Schurr, Long Beach, CA (US)

(73) Assignee: Entelexo Biotherapeutics, Inc., Irvine, CA (US)

( * ) Notice: Subject to any disclaimer, the term of this patent is extended or adjusted under 35 U.S.C. 154(b) by 0 days.

(21) Appl. No.: 17/855,305

(22) Filed: Jun. 30, 2022

(65) Prior Publication Data

US 2022/0389078 A1 Dec. 8, 2022

Related U.S. Application Data

(63) Continuation of application No. 17/556,572, filed on Dec. 20, 2021, which is a continuation of application No. PCT/US2020/038816, filed on Jun. 19, 2020.

(60) Provisional application No. 62/875,001, filed on Jul. 17, 2019, provisional application No. 62/864,566, filed on Jun. 21, 2019.

(51) Int. Cl.
| *C07K 14/70* | (2006.01) |
| *A61P 29/00* | (2006.01) |
| *A61K 9/50* | (2006.01) |
| *C07K 14/705* | (2006.01) |
| *A61K 47/42* | (2017.01) |
| *A61K 38/00* | (2006.01) |

(52) U.S. Cl.
CPC ...... *C07K 14/70521* (2013.01); *A61K 9/5068* (2013.01); *A61K 47/42* (2013.01); *A61P 29/00* (2018.01); *C07K 14/70503* (2013.01); *C07K 14/70532* (2013.01); *C07K 14/70596* (2013.01); *A61K 38/00* (2013.01); *C07K 2319/03* (2013.01)

(58) Field of Classification Search
CPC .. C07K 14/70521; A61P 29/00; A61K 9/5068
See application file for complete search history.

(56) References Cited

U.S. PATENT DOCUMENTS

| 4,229,447 A | 10/1980 | Porter |
| 4,476,116 A | 10/1984 | Anik |
| 4,596,795 A | 6/1986 | Pitha |
| 4,755,386 A | 7/1988 | Hsiao et al. |
| 5,011,692 A | 4/1991 | Fujioka et al. |
| 5,017,381 A | 5/1991 | Maruyama et al. |
| 5,116,817 A | 5/1992 | Anik |
| 5,229,135 A | 7/1993 | Philippon et al. |
| 5,739,136 A | 4/1998 | Ellinwood, Jr. et al. |
| 5,837,284 A | 11/1998 | Mehta et al. |
| 5,840,329 A | 11/1998 | Bai |
| 5,858,401 A | 1/1999 | Bhalani et al. |
| 6,391,452 B1 | 5/2002 | Antonsen et al. |
| 6,667,048 B1 | 12/2003 | Lambert et al. |
| 6,960,563 B2 | 11/2005 | Egbaria et al. |
| 2018/0289805 A1* | 10/2018 | Peyman ............ A61K 45/06 |
| 2022/0112264 A1 | 4/2022 | Riazifar et al. |

FOREIGN PATENT DOCUMENTS

| WO | WO 2017/122095 | * | 7/2017 |
| WO | WO 2017/203260 | * | 11/2017 |
| WO | WO 2018/015535 | * | 1/2018 |
| WO | WO-2018015535 A1 | | 1/2018 |
| WO | WO-2018075825 A1 | | 4/2018 |
| WO | WO-2018129207 A1 | | 7/2018 |
| WO | WO-2018208670 A1 | | 11/2018 |
| WO | WO-2019027847 A1 | | 2/2019 |
| WO | WO 2019/081474 | * | 5/2019 |
| WO | WO 2019/092287 | * | 5/2019 |
| WO | WO-2020257710 A1 | | 12/2020 |
| WO | WO-2021102585 A1 | | 6/2021 |
| WO | WO-2022133301 A1 | | 6/2022 |

OTHER PUBLICATIONS

Whiteside, 2013, Immune modulation of T-cell and NK (natural killer) cell activities by TEXs (tumour-derived exosomes), Biochem Sci Trans, 41(1): 245-251.*
Li et al., 2019, Exosomes in the tumor microenvironment as mediators of cancer therapy resistance, Molecular Cancer, 18: 32 (10 pages).*
Guo et al., 2019, Effects of exosomes on pre-metastatic niche formation in tumors, Molecular Cancer, 18: 39 (11 pages).*
Whiteside, 2018, The emerging role of plasma exosomes in diagnosis, prognosis and therapies of patients with cancer, Contemp Oncol, 22(1A): 38-40.*
Chavez et al., Highly efficient Cas9-mediated transcriptional programming. Nature Methods 12(4): 326-328 (2015).
El-Andaloussi et al.: Exome-mediated delivery of siRNA in vitro and in vivo. Nat Protoc. 7(12):2112-2126 (2012).
Ghosh et al.: Glycobiology 5:505-510 (1991).

(Continued)

Primary Examiner — Amber D Steele

(74) Attorney, Agent, or Firm — Wilson Sonsini Goodrich & Rosati

(57) ABSTRACT

Descried herein are platforms for generating extracellular vesicles. Described herein are compositions of extracellular vesicles. Also described herein are methods of using the extracellular vesicles for therapeutics delivery.

14 Claims, 3 Drawing Sheets

Specification includes a Sequence Listing.

(56) References Cited

OTHER PUBLICATIONS

PCT/US2020/038816 International Preliminary Report on Patentability dated Dec. 30, 2021.
PCT/US2020/038816 International Search Report and Written Opinion dated Nov. 4, 2020.
PCT/US2020/038816 Invitation to Pay Additional Fees dated Sep. 10, 2020.
PCT/US2021/064186 International Search Report and Written Opinion dated Mar. 22, 2022.
Riazifar et al.: Stem Cell-Derived Exosomes as Nanotherapeutics for Autoimmune and Neurodegenerative Disorders. ACS Nano. 13(6):6670-6688, 2019 doi:10.1021/acsnano.9b01004.
Sambrook et al.: Molecular Cloning: A Laboratory Manual. Chapter 18:18.1-18.88 (1989).
Singh et al. Encyclopedia of Pharmaceutical Technology 2nd Ed. pp. 754-757 (2002).
Xitong et al.: Targeted therapeutic delivery using engineered exosomes and its applications in cardiovascular diseases. Gene. 575:377-384 (2016).
Chen et al.: Immunomodulatory effects of mesenchymal stromal cells-derived exosome. Immunology Research. Human Press, Inc. 64(4):831-840 (2016).
European Application No. 20825438.3 Search Report dated Jun. 16, 2023.
Fitts et al.: Exploiting Exosomes in Cancer Liquid Biopsies and Drug Delivery. Advanced Healthcare Materials. 8(6):201801268 1-8 (2019).
Khair et al.: Combining Immune Checkpoint Inhibitors: Established and Emerging Targets and Strategies to Improve Outcomes in Melanoma. Frontiers in Immunology. 10(453):1-20 (2019).

* cited by examiner

PLATFORMS, COMPOSITIONS, AND METHODS FOR THERAPEUTIC DELIVERY

CROSS-REFERENCE

This application is a Continuation of International Application No. PCT/US2020/038816, filed Jun. 19, 2020, which claims the benefit of U.S. Provisional Application Ser. No. 62/864,566 filed on Jun. 21, 2019 and U.S. Provisional Application Ser. No. 62/875,001 filed on Jul. 17, 2019, the entirety of which are hereby incorporated by reference herein.

SEQUENCE LISTING

The instant application contains a Sequence Listing which has been submitted electronically in ASCII format and is hereby incorporated by reference in its entirety. Said ASCII copy, created on Dec. 17, 2021, is named 58743-701_301_SL.txt, and is 40,984 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference. This application incorporates "Riazifar M, Mohammadi M R, Pone E J, et al. Stem Cell-Derived Exosomes as Nanotherapeutics for Autoimmune and Neurodegenerative Disorders. ACS Nano. 2019; 13(6):6670-6688. doi:10.1021/acsnano.9b01004", the entirety of which are hereby incorporated by reference herein.

BACKGROUND

Effective means of delivering therapeutics to a target cell is one of the cornerstones of modern medicine. Extracellular vesicles have been explored and utilized as carriers for delivering therapeutics to a target cell.

SUMMARY

Current methods of delivering therapeutics via extracellular vesicles have drawbacks. The extracellular vesicles can be heterogenous in terms of sizes, numbers, membrane properties, or stability. The amount of therapeutics that can delivered by the extracellular vesicles can be uneven or unpredictable, leading to ineffective treatment outcomes. In some instances, the yield of the extracellular vesicles can be inadequate. Additionally, directing the extracellular vesicles to an in vivo target cell is an ongoing challenge due to majority of the extracellular vesicles in circulation accumulate in liver, spleen, and kidney. Therefore, there remains a need for compositions and pharmaceutical compositions comprising extracellular vesicles for delivering sufficient quantity of therapeutics to a target cell. There remains a need for platforms and methods for producing extracellular vesicles to deliver sufficient quantity of therapeutics to a target cell. There also remains a need for methods of using extracellular vesicles to deliver therapeutics and methods of using extracellular vesicles to treat a disease or a condition.

An aspect of the present disclosure comprises a composition comprising an extracellular vesicle, said extracellular vesicle comprising: an immune checkpoint moiety, wherein said immune checkpoint moiety comprises VISTA, PD-L1, CTLA-4, or any combination thereof; and a transmembrane moiety, wherein said transmembrane moiety comprises CD63, wherein said CD63 comprises 3 transmembrane domains; wherein said immune checkpoint moiety is coupled to said transmembrane moiety. In some embodiments, said immune checkpoint moiety is coupled to an extracellular loop of said CD63 to generate a modified CD63. In some embodiments, said extracellular loop is a large extracellular loop or the second extracellular loop of said modified CD63. In some embodiments, said modified CD63 comprises an amino acid sequence at least 90% identical to any one of the amino acid sequences set forth in SEQ ID Nos: 6-17. In some embodiments, said modified CD63 comprises an amino acid sequence at least 95% identical to any one of the amino acid sequences set forth in SEQ ID Nos: 6-17. In some embodiments, said modified CD63 comprises any one of the amino acid sequences set forth in SEQ ID Nos: 6-17. A composition comprising an extracellular vesicle, said extracellular vesicle comprising: an immune checkpoint moiety, wherein said immune checkpoint moiety comprises PD-L1; and a transmembrane moiety, wherein said transmembrane moiety comprises lactadherin; wherein said immune checkpoint moiety is coupled to said transmembrane moiety. A composition comprising an extracellular vesicle, said extracellular vesicle comprising: an immune checkpoint moiety, wherein said immune checkpoint moiety comprises V-domain Ig suppressor of T cell activation (VISTA), PD-L1, CTLA-4, or any combination thereof; and a transmembrane moiety, wherein said transmembrane moiety comprises glycosylphosphatidylinositol (GPI); wherein said immune checkpoint moiety is coupled to said transmembrane moiety. A composition comprising an extracellular vesicle, said extracellular vesicle comprising at least one of: an immune checkpoint moiety; and a transmembrane moiety. In some embodiments, the immune checkpoint moiety is encapsulated by the extracellular vesicle. In some embodiments, the immune checkpoint moiety is expressed on a surface of the extracellular vesicle. In some embodiments, the immune checkpoint moiety is secreted by the extracellular vesicle. In some embodiments, the immune checkpoint moiety is complexed with the transmembrane moiety. In some embodiments, the immune checkpoint moiety is covalently connected with the transmembrane moiety. In some embodiments, the immune checkpoint moiety comprises VISTA, PD-L1, CTLA-4, PD-L2, B7-1 (CD80), B7-2 (CD86), B7-H3 (CD276), B7-H2, B7-H4 (VTCN1), HVEM (CD270, TNFRSF14), Galectin 9, Galectin3, CEACAM1 (CD66a), OX-2 (CD200), PVR (CD155), PVRL2 (Nectin-2, CD112), FGL-1, PECAM-1, TSG-6, CD47, Stabilin-1 (Clever-1), Neuropilin 1, Neuropilin 2, CD158 (family), IGSF2 (CD101), CD155, GITRL, CD137L, OX40L, LIGHT, CD70, PD-1, RGMB, CTLA-4 (CD152), BTLA, CD160, Tim-3, CD200R, TIGIT, CD112R (PVRIG), LAG-3 (CD223), PECAM-1, CD44, SIRP alpha (CD172a), or a combination thereof. In some embodiments, the immune checkpoint moiety comprises VISTA, PD-L1, CTLA-4, or a combination thereof. In some embodiments, the immune checkpoint moiety comprises PD-L1. In some embodiments, the transmembrane moiety is selected from a group consisting of 14-3-3 protein zeta/delta, 4-3-3 protein epsilon, 78 kDa glucose-regulated protein, acetylcholinesterase/AChE-S, AChE-E, actin, cytoplasmic 1 (ACTA), ADAM10, alkaline phosphatase, alpha-enolase, alpha-synuclein, aminopeptidase N, amyloid beta A4/APP, annexin 5A, annexin A2, AP-1, ATF3, ATP citrate lyase, ATPase, beta actin (ACTB), beta-amyloid 42, caveolin-1, CD10, CD11a, CD11b, CD11c, CD14, CD142, CD146, CD163, CD24, CD26/ DPP4, CD29/ITGB1, CD3, CD37, CD41, CD42a, CD44, CD45, CD47, CD49, CD49d, CD53, CD63, CD64, CD69, CD73 CD81, CD82, CD9, CD90, claudin, claudin-1 cofilin-1, complement-binding proteins CD55 and CD59, cytosolic heat shock protein 90 alpha, cytosolic heat shock protein 90 beta, EBV LMP1, EBV LMP2A, EF-1alpha-1, EF2, EFGR EGFR VIII, emmprin/CD147, enolase 1 alpha (ENO1), EPCAM, ERBB2, tetraspanins (CD9, CD63 and CD81), fatty acid synthase, fetuin-A, flotillin-1, flotillin-2, fructose-bisphosphate aldolase A, glyceraldehyde-3-phosphate dehydrogenase (GAPDH), glycophorin A, GPC1, GPI-anchored 5'nucleotidase, GTPase, heat shock protein 8 (HSPA8), heat shock proteins (HSP70 and HSP90), heparan sulfate proteoglycans, heparinase, heterotrimeric G proteins, HIV Gag, HIV Nef, HLA-DRA, HLA-G, HSV gB, HTLV-1 Tax, huntingtin, ICAM1, integrins, lactadherin, LAMP1/2, leucine-rich receptor kinase 2, L-lactate dehydrogenase A chain, lysosome-associated membrane glycoprotein 1, lysosome-associated membrane glycoprotein 2, MEW class I, MHC class II, MUC1, multidrug resistance-associated protein, muscle pyruvate kinase (PKM2), N-cadherin, NKCC2, PDCD6IP/Alix, PECAM1, phosphoglycerate kinase, placental prion proteins, prostate-specific antigen (PSA), pyruvate kinase (PKM), Rab-14, Rab-5a, Rab-5b, Rab-5c, Rab-7, Rap 1B, resistin, sonic hedgehog (SHH), surviving, syndecan-1, syndecan-4, syntenin-1, transferrin receptor (TFR2), TSG101, TSPAN8, tumor-associated glycoprotein tetraspanin-8, tyrosine 3 monooxygenase/tryptophan 5-monooxygenase activation protein, TYRP-2, vacuolar-sorting protein 35, or zeta polypeptide (YWHAZ). In some embodiments, the transmembrane moiety comprises lactadherin. In some embodiments, the transmembrane moiety comprises LAMP2 or a variation thereof or a fragment thereof, said LAMP2 is at least 70% identical to a peptide sequence of SEQ ID NO: 4 In some embodiments, the transmembrane moiety comprises CD63 or a variation thereof or a fragment thereof, said CD63 is at least 70% identical to a peptide sequence of SEQ ID NO: 5. In some embodiments, the CD63 is a modified CD63. In some embodiments, the modified CD63 is a truncated CD63. In some embodiments, the modified CD63 is modified to comprise at least one additional CD63 transmembrane domain. In some embodiments, the modified CD63 comprises 1 transmembrane domain. In some embodiments, the modified CD63 comprises 2 transmembrane domains. In some embodiments, the modified CD63 comprises 3 transmembrane domains. In some embodiments, the modified CD63 comprises 4 transmembrane domains. In some embodiments, the modified CD63 comprises 5 transmembrane domains. In some embodiments, the immune checkpoint moiety is complexed with the modified CD63 at an extracellular loop of the modified CD63. In some embodiments, the immune checkpoint moiety is complexed with the modified CD63 at a large extracellular loop of the modified CD63. In some embodiments, the composition further comprises a targeting moiety. In some embodiments, the targeting moiety comprises a peptide that targets cytokine. In some embodiments, the targeting moiety comprises a peptide that targets a cancer cell marker. In some embodiments, the composition further comprises a fusogenic moiety. In some embodiments, the fusogenic moiety comprises a viral fusogenic moiety. In some embodiments, the fusogenic moiety comprises a mammalian fusogenic moiety. In some embodiments, the composition further comprises an immune evasion moiety. In some embodiments, the immune evasion moiety comprises CD47. The composition of any one of the previous claims does not comprise enucleated cell. In some embodiments, the extracellular vesicle comprises exosome, microvesicle, retrovirus-like particle, apoptotic body, apoptosome, oncosome, exopher, enveloped virus, exomere, or other very large extracellular vesicle. In some embodiments, the extracellular vesicle comprises exosome. In some embodiments, the extracellular vesicle comprises a plurality of immune checkpoint moieties. In some embodiments, the extracellular vesicle comprises at least 10,000 units of the immune checkpoint moiety per each extracellular vesicle, said extracellular vesicle comprises a diameter of 100 nm. In some embodiments, the extracellular vesicle comprises at least 9,000 units of the immune checkpoint moiety per each extracellular vesicle, said extracellular vesicle comprises a diameter of 100 nm. In some embodiments, the extracellular vesicle comprises at least 8,000 units of the immune checkpoint moiety per each extracellular vesicle, said extracellular vesicle comprises a diameter of 100 nm. In some embodiments, the extracellular vesicle comprises at least 7,000 units of the immune checkpoint moiety per each extracellular vesicle, said extracellular vesicle comprises a diameter of 100 nm. In some embodiments, the extracellular vesicle comprises at least 6,000 units of the immune checkpoint moiety per each extracellular vesicle, said extracellular vesicle comprises a diameter of 100 nm. In some embodiments, the extracellular vesicle comprises at least 5,000 units of the immune checkpoint moiety per each extracellular vesicle, said extracellular vesicle comprises a diameter of 100 nm. In some embodiments, the extracellular vesicle comprises at least 3,000 units of the immune checkpoint moiety per each extracellular vesicle, said extracellular vesicle comprises a diameter of 50 nm. In some embodiments, the extracellular vesicle comprises at least 2,500 units of the immune checkpoint moiety per each extracellular vesicle, said extracellular vesicle comprises a diameter of 50 nm. In some embodiments, the extracellular vesicle comprises at least 2,000 units of the immune checkpoint moiety per each extracellular vesicle, said extracellular vesicle comprises a diameter of 50 nm. In some embodiments, the extracellular vesicle comprises at least 1,500 units of the immune checkpoint moiety per each extracellular vesicle, said extracellular vesicle comprises a diameter of 50 nm. In some embodiments, the composition comprises a plurality of exosome. In some embodiments, the composition comprises a therapeutically effective amount of exosome. In some embodiments, the composition further comprises at least $10^{1'6}$ exosomes. In some embodiments, the composition further comprises at least $10^{1'7}$ exosomes. In some embodiments, the composition further comprises at least $10^{1'8}$ exosomes. In some embodiments, the composition further comprises at least 1 µg of exosomes. In some embodiments, the composition further comprises at least 10 µg of exosomes. In some embodiments, the composition further comprises at least 20 µg of exosomes. In some embodiments, the composition further comprises at least 50 µg of exosomes. In some embodiments, the composition further comprises at least 100 µg of exosomes. In some embodiments, the composition further comprises at least 150 µg of exosomes. In some embodiments, the composition further comprises at least 200 µg of exosomes. In some embodiments, the composition further comprises at least 250 µg of exosomes. In some embodiments, the composition further comprises at least 500 µg of exosomes. In some embodiments, the composition further comprises at least 750 µg of exosomes. In some embodiments, the composition further comprises at least 1 mg of exosomes. In some embodiments, the composition further comprises at least 2 mg of exosomes. In some embodiments, the composition further comprises at least 3 mg of exosomes. In some embodiments, the composition further comprises at least 4 mg of exosomes. In some embodiments, the composition further comprises at least 5 mg of exosomes. In some embodiments, the composition further comprises at least 6 mg of exosomes. In some embodiments, the composition further comprises at least 7 mg of exosomes. In some embodiments, the composition further comprises at least 100 mg of exosomes. In some embodiments, the composition further comprises at least 200 mg of exosomes. In some embodiments, the composition further comprises at least 300 mg of exosomes. In some embodiments, the composition further comprises at least 400 mg of exosomes. In some embodiments, the composition further comprises at least 500 mg of exosomes. In some embodiments, the composition further comprises at least 600 mg of exosomes. In some embodiments, the composition further comprises at least 700 mg of exosomes. In some embodiments, the composition is derived from a cell. In some embodiments, the composition is cryopreserved. In some embodiments, the composition is lyophilized. In some embodiments, the composition is stable at 37° C. for 24 hours. In some embodiments, the composition is stable at 37° C. for 48 hours. In some embodiments, the composition is stable at 37° C. for 72 hours.

Another aspect of the present disclosure comprises a cell configured to generate the extracellular vesicle or exosome of any one of the embodiments described herein. In some embodiments, said cell is a stem cell. In some embodiments, wherein the cell is a human cell. In some embodiments, the cell is a non-human cell. In some embodiments, the cell is a mesenchymal stem cell. In some embodiments, the cell is a genetically modified cell. In some embodiments, the cell is genetically modified to produce the extracellular vesicles or exosomes described in any one of the embodiments described herein.

Another aspect of the present disclosure comprises a method of purifying extracellular vesicle configured to express one or more immune checkpoint moiety, said method comprising: obtaining a heterogenous population of extracellular vesicle; subjecting the heterogenous population of extracellular vesicle to a detection assay solution, said detection assay solution comprising a detecting moiety for complexing with the immune checkpoint moiety; and detecting a signal generated from complex formed between the immune checkpoint moiety and the detecting moiety, wherein intensity of the signal is proportional to units of immune checkpoint moiety expressed; and isolating a subpopulation of the extracellular vesicle based on the intensity of the signal. In some embodiments, the detecting moiety comprises an antibody. In some embodiments, the detecting moiety comprises anti-VISTA antibody, anti-PD-L1 antibody, anti-CTLA-4 or a combination thereof. In some embodiments, the detecting moiety comprises a ligand of the immune checkpoint moiety. In some embodiments, the detection assay solution further comprises a peptide configured to bind to said immune checkpoint moiety. In some embodiments, the peptide configured to bind to said immune checkpoint moiety comprises PD-1, CD80, CD86, or a combination thereof.

Another aspect of the present disclosure comprises a pharmaceutical composition comprising the composition of any one of the embodiments described herein. In some embodiments, the pharmaceutical composition further comprises a pharmaceutically acceptable carrier. In some embodiments, the pharmaceutical composition further comprises at least one additional active agent. In some embodiments, the pharmaceutical composition is formulated for administering intrathecally, intraocularly, intravitreally, retinally, intravenously, intramuscularly, intraventricularly, intracerebrally, intracerebellarly, intracerebroventricularly, intraparenchymally, subcutaneously, or a combination thereof.

Another aspect of the present disclosure comprises a method of treating an autoimmune disease, the method comprising administering the pharmaceutical composition of any one of the embodiments described herein. In some embodiments, said autoimmune disease is Rheumatoid arthritis, Systemic lupus erythematosus, Psoriasis, Type 1 diabetes mellitus, Multiple sclerosis, Inflammatory bowel disease, Celiac disease, Crohn's disease, Graves' disease, Juvenile arthritis, Lyme disease chronic, Optic neuritis, Psoriatic arthritis, Scleritis, Scleroderma, Ulcerative colitis (UC), Uveitis, Inflammatory eye conditions, Vitiligo, COPD, complication from Organ transplantation, or graft-versus-host disease. In some embodiments, said autoimmune disease is Rheumatoid arthritis.

Another aspect of the present disclosure comprises a method of suppressing CD8+CD25+ cells in a patient in need thereof, the method comprising administering the composition of any one of the embodiments described herein.

Another aspect of the present disclosure comprises a kit comprising the pharmaceutical composition of any one of the embodiments described herein.

Another aspect of the present disclosure comprises a platform comprising components for generating the composition of any one of the embodiments described herein.

BRIEF DESCRIPTION OF THE DRAWINGS

This patent application contains at least one drawing executed in color. Copies of this patent or patent application with color drawing(s) will be provided by the Office upon request and payment of the necessary fee.

Programmed death ligand-1 (PD-L1).

Figure 2:
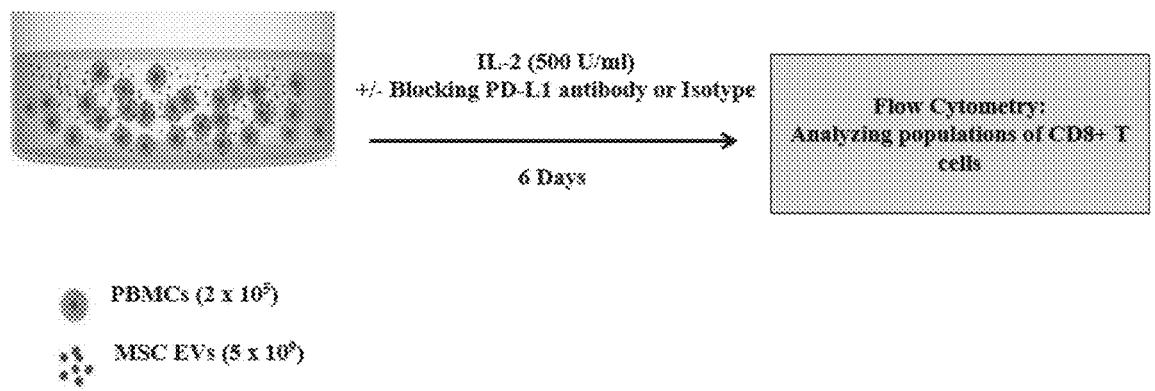

FIG. 2 illustrates an experimental design for blocking PD-L1 to determine how blocking PD-L1 affected CD8+ T cells.

Figure 3:
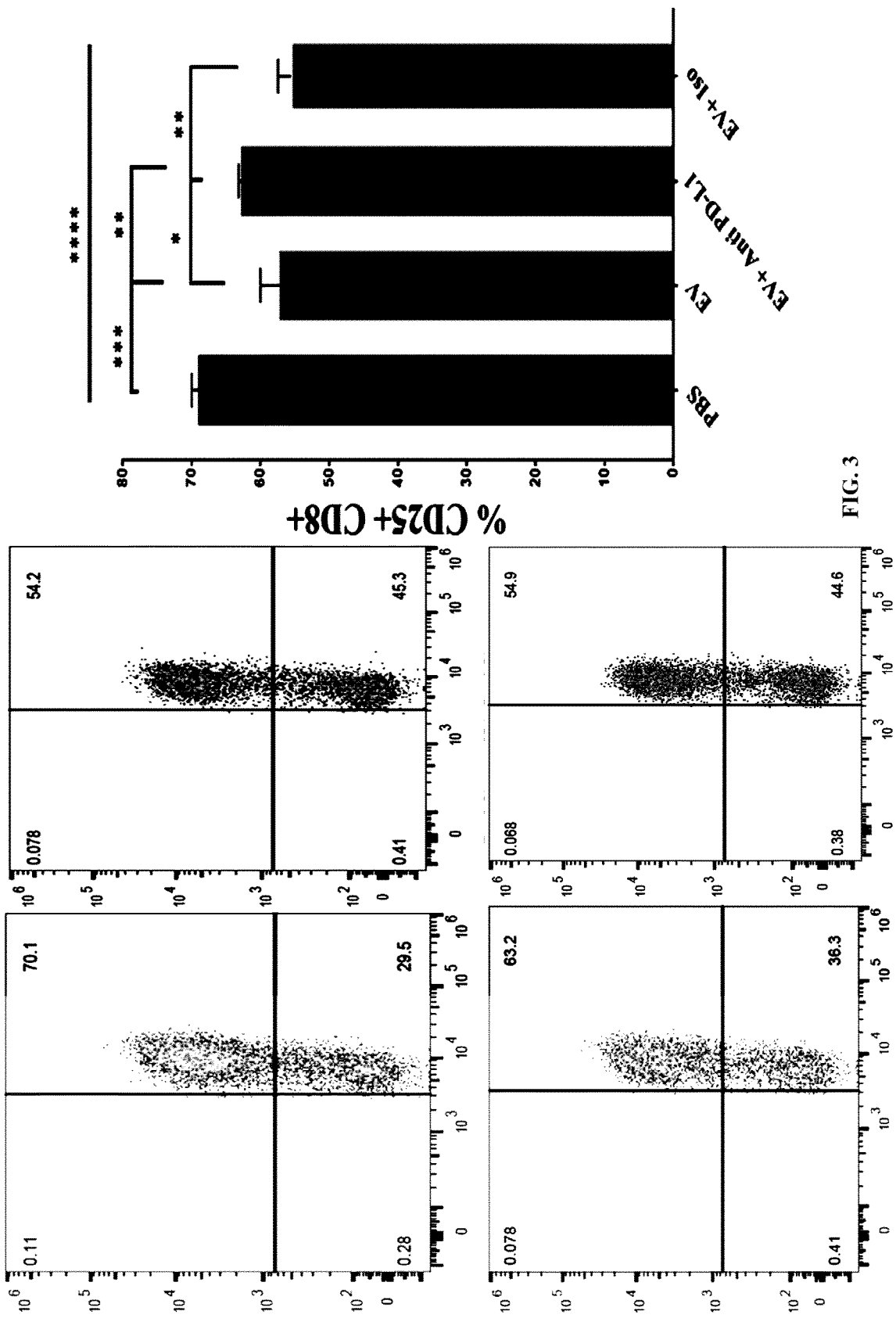

FIG. 3 illustrates that the presence of blocking PD-L1 antibody abolished the effected of PD-L1 on CD25+CD8+ cell.

DETAILED DESCRIPTION

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Use of absolute or sequential terms, for example, "will," "will not," "shall," "shall not," "must," "must not," "first," "initially," "next," "subsequently," "before," "after,"

"lastly," and "finally," are not meant to limit scope of the present embodiments disclosed herein but as exemplary.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C", and "A, B, and/or C" means A alone, B alone, C alone, A and B together, A and C together, B and C together, or A, B and C together.

Any systems, methods, software, and platforms described herein are modular and not limited to sequential steps. Accordingly, terms such as "first" and "second" do not necessarily imply priority, order of importance, or order of acts.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "increased" or "increase" are used herein to generally mean an increase by a statically significant amount; in some embodiments, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90%, or up to and including a 100% increase, or any increase between 10-100% as compared to a reference level, standard, or control. Other examples of "increase" include an increase of at least 2-fold, at least 5-fold, at least 10-fold, at least 20-fold, at least 50-fold, at least 100-fold, at least 1000-fold, or more as compared to a reference level.

The terms "decreased" or "decrease" are used herein generally to mean a decrease by a statistically significant amount. In some embodiments, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90%, or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

The terms "individual," "patient," or "subject" are used interchangeably. None of the terms require or are limited to situation characterized by the supervision (e.g., constant or intermittent) of a health care worker (e.g., a doctor, a registered nurse, a nurse practitioner, a physician's assistant, an orderly, or a hospice worker).

As used herein, a "cell" generally refers to a biological cell. A cell can be the basic structural, functional and/or biological unit of a living organism. A cell can originate from any organism having one or more cells. Some non-limiting examples include: a prokaryotic cell, eukaryotic cell, a bacterial cell, an archaeal cell, a cell of a single-cell eukaryotic organism, a protozoa cell, a cell from a plant (e.g., cells from plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses), an algal cell, (e.g., *Botryococcus braunii, Chlamydomonas reinhardtii, Nannochloropsis gaditana, Chlorella pyrenoidosa, Sargassum patens C. Agardh*, and the like), seaweeds (e.g., kelp), a fungal cell (e.g., a yeast cell, a cell from a mushroom), an animal cell, a cell from an invertebrate animal (e.g., fruit fly, cnidarian, echinoderm, nematode, etc.), a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.), and etcetera. Sometimes a cell is not originating from a natural organism (e.g., a cell can be a synthetically made, sometimes termed an artificial cell).

The term "nucleotide," as used herein, generally refers to a base-sugar-phosphate combination. A nucleotide can comprise a synthetic nucleotide. A nucleotide can comprise a synthetic nucleotide analog. Nucleotides can be monomeric units of a nucleic acid sequence (e.g., deoxyribonucleic acid (DNA) and ribonucleic acid (RNA)). The term nucleotide can include ribonucleoside triphosphates adenosine triphosphate (ATP), uridine triphosphate (UTP), cytosine triphosphate (CTP), guanosine triphosphate (GTP) and deoxyribonucleoside triphosphates such as dATP, dCTP, dITP, dUTP, dGTP, dTTP, or derivatives thereof. Such derivatives can include, for example, [αS]dATP, 7-deaza-dGTP and 7-deaza-dATP, and nucleotide derivatives that confer nuclease resistance on the nucleic acid molecule containing them. The term nucleotide as used herein can refer to dideoxyribonucleoside triphosphates (ddNTPs) and their derivatives. Illustrative examples of dideoxyribonucleoside triphosphates can include, but are not limited to, ddATP, ddCTP, ddGTP, ddITP, and ddTTP. A nucleotide can be unlabeled or detectably labeled by well-known techniques. Labeling can also be carried out with quantum dots. Detectable labels can include, for example, radioactive isotopes, fluorescent labels, chemiluminescent labels, bioluminescent labels and enzyme labels. Fluorescent labels of nucleotides can include but are not limited fluorescein, 5-carboxyfluorescein (FAM), 2'7'-dimethoxy-4'5-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides can include [R6G]dUTP, [TAMRA]dUTP, [R110]dCTP, [R6G]dCTP, [TAMRA]dCTP, [JOE]ddATP, [R6G]ddATP, [FAM]ddCTP, [R110]ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif; FluoroLink DeoxyNucleotides, FluoroLink Cy3-dCTP, FluoroLink Cy5-dCTP, FluoroLink Fluor X-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosome Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg. Nucleotides can also be labeled or marked by chemical modification. A chemically-modified single nucleotide can be biotin-dNTP. Some non-limiting examples of biotinylated dNTPs can include, biotin-dATP (e.g., bio-N6-ddATP, biotin-14-dATP), biotin-dCTP (e.g., biotin-11-dCTP, biotin-14-dCTP), and biotin-dUTP (e.g., biotin-11-dUTP, biotin-16-dUTP, biotin-20-dUTP).

The terms "polynucleotide," "oligonucleotide," and "nucleic acid" are used interchangeably to refer to a polymeric form of nucleotides of any length, either deoxyribonucleotides or ribonucleotides, or analogs thereof, either in single-, double-, or multi-stranded form. A polynucleotide can be exogenous or endogenous to a cell. A polynucleotide can exist in a cell-free environment. A polynucleotide can be a gene or fragment thereof. A polynucleotide can be DNA. A polynucleotide can be RNA. A polynucleotide can have any three dimensional structure, and can perform any function, known or unknown. A polynucleotide can comprise one or more analogs (e.g., altered backbone, sugar, or nucleobase). If present, modifications to the nucleotide structure can be imparted before or after assembly of the polymer. Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, fluorophores (e.g., rhodamine or fluorescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. Non-limiting examples of polynucleotides include coding or non-coding regions of a gene or gene fragment, loci (locus) defined from linkage analysis, exons, introns, messenger RNA (mRNA), transfer RNA (tRNA), ribosomal RNA (rRNA), short interfering RNA (siRNA), short-hairpin RNA (shRNA), microRNA (miRNA), ribozymes, cDNA, recombinant polynucleotides, branched polynucleotides, plasmids, vectors, isolated DNA of any sequence, isolated RNA of any sequence, cell-free polynucleotides including cell-free DNA (cfDNA) and cell-free RNA (cfRNA), nucleic acid probes, and primers. The sequence of nucleotides can be interrupted by non-nucleotide components.

The terms "transfection" or "transfected" generally refers to introduction of a nucleic acid into a cell by non-viral or viral-based methods. The nucleic acid molecules can be gene sequences encoding complete proteins or functional portions thereof. See, e.g., Sambrook et al., 1989, Molecular Cloning: A Laboratory Manual, 18.1-18.88.

The term "expression" or "expressing" refers to one or more processes by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides can be collectively referred to as "gene product." If the polynucleotide is derived from genomic DNA, expression can include splicing of the mRNA in a eukaryotic cell. "Up-regulated," with reference to expression, generally refers to an increased expression level of a polynucleotide (e.g., RNA such as mRNA) and/or polypeptide sequence relative to its expression level in a wild-type state while "down-regulated" generally refers to a decreased expression level of a polynucleotide (e.g., RNA such as mRNA) and/or polypeptide sequence relative to its expression in a wild-type state.

The term "gene," as used herein, refers to a segment of nucleic acid that encodes an individual protein or RNA (also referred to as a "coding sequence" or "coding region"), optionally together with associated regulatory region such as promoter, operator, terminator and the like, which can be located upstream or downstream of the coding sequence. The term "gene" is to be interpreted broadly, and can encompass mRNA, cDNA, cRNA and genomic DNA forms of a gene. In some uses, the term "gene" encompasses the transcribed sequences, including 5' and 3' untranslated regions (5'-UTR and 3'-UTR), exons and introns. In some genes, the transcribed region will contain "open reading frames" that encode polypeptides. In some uses of the term, a "gene" comprises only the coding sequences (e.g., an "open reading frame" or "coding region") necessary for encoding a polypeptide. In some aspects, genes do not encode a polypeptide, for example, ribosomal RNA genes (rRNA) and transfer RNA (tRNA) genes. In some aspects, the term "gene" includes not only the transcribed sequences, but in addition, also includes non-transcribed regions including upstream and downstream regulatory regions, enhancers and promoters. The term "gene" can encompass mRNA, cDNA and genomic forms of a gene.

As used herein, the terms "polypeptide," "peptide" and "protein" can be used interchangeably herein in reference to a polymer of amino acid residues. A protein can refer to a full-length polypeptide as translated from a coding open reading frame, or as processed to its mature form, while a polypeptide or peptide can refer to a degradation fragment or a processing fragment of a protein that nonetheless uniquely or identifiably maps to a particular protein. A polypeptide can be a single linear polymer chain of amino acids bonded together by peptide bonds between the carboxyl and amino groups of adjacent amino acid residues. Polypeptides can be modified, for example, by the addition of carbohydrate, phosphorylation, etc. Proteins can comprise one or more polypeptides.

As used herein, the terms "fragment," or equivalent terms can refer to a portion of a protein that has less than the full length of the protein and optionally maintains the function of the protein. Further, when the portion of the protein is blasted against the protein, the portion of the protein sequence can align, for example, at least with 80% identity to a part of the protein sequence.

The terms "complement," "complements," "complementary," and "complementarity," as used herein, generally refer to a sequence that is fully complementary to and hybridizable to the given sequence. In some cases, a sequence hybridized with a given nucleic acid is referred to as the "complement" or "reverse-complement" of the given molecule if its sequence of bases over a given region is capable of complementarily binding those of its binding partner, such that, for example, A-T, A-U, G-C, and G-U base pairs are formed. In general, a first sequence that is hybridizable to a second sequence is specifically or selectively hybridizable to the second sequence, such that hybridization to the second sequence or set of second sequences is preferred (e.g., thermodynamically more stable under a given set of conditions, such as stringent conditions commonly used in the art) to hybridization with non-target sequences during a hybridization reaction. Typically, hybridizable sequences share a degree of sequence complementarity over all or a portion of their respective lengths, such as between 25%-100% complementarity, including at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, and 100% sequence complementarity. Sequence identity, such as for the purpose of assessing percent complementarity, can be measured by any suitable alignment algorithm, including but not limited to the Needleman-Wunsch algorithm (see e.g., the EMBOSS Needle aligner), the BLAST algorithm (see e.g. the BLAST alignment tool), or the Smith-Waterman algorithm (see e.g. the EMBOSS Water aligner). Optimal alignment can be assessed using any suitable parameters of a chosen algorithm, including default parameters.

The term "percent (%) identity," as used herein, generally refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment, for purposes of determining percent identity, can be achieved in various ways that are within the skill in the art, for instance, using publicly available computer software such as BLAST, ALIGN, or Megalign (DNASTAR) software. Percent identity of two sequences can be calculated by aligning a test sequence with a comparison sequence using BLAST, determining the number of amino acids or nucleotides in the aligned test sequence that are identical to amino acids or nucleotides in the same position of the comparison sequence, and dividing the number of identical amino acids or nucleotides by the number of amino acids or nucleotides in the comparison sequence.

The term "mismatch" generally refers to lack of complementarity between two nucleotides when aligned. Complementary bases in DNA are A-T and G-C. Complementary bases in RNA are A-U and G-C. Thus a mismatch occurs when two oligonucleotide sequences are aligned and at one or more nucleotide positions that an A is not paired with T or a G is not paired with C in DNA or an A is not paired with U or a G is not paired with C in RNA.

As used herein, the term "in vivo" can be used to describe an event that takes place in a subject's body.

As used herein, the term "ex vivo" can be used to describe an event that takes place outside of a subject's body. An "ex vivo" assay cannot be performed on a subject. Rather, it can be performed upon a sample separate from a subject. Ex vivo can be used to describe an event occurring in an intact cell outside a subject's body.

As used herein, the term "in vitro" can be used to describe an event that takes places contained in a container for holding laboratory reagent such that it is separated from the living biological source organism from which the material is obtained. In vitro assays can encompass cell-based assays in which cells alive or dead are employed. In vitro assays can also encompass a cell-free assay in which no intact cells are employed.

"Treating" or "treatment" can refer to both therapeutic treatment and prophylactic or preventative measures, wherein the object is to prevent or slow down (lessen) a targeted pathologic condition or disorder. Those in need of treatment include those already with the disorder, as well as those prone to have the disorder, or those in whom the disorder is to be prevented. A therapeutic benefit can refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject can still be afflicted with the underlying disorder. A prophylactic effect can include delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease can undergo treatment, even though a diagnosis of this disease cannot have been made.

The term "effective amount" and "therapeutically effective amount," as used interchangeably herein, generally refer to the quantity of a composition, for example a composition comprising immune cells such as lymphocytes (e.g., T lymphocytes and/or NK cells) comprising a system of the present disclosure, that is sufficient to result in a desired activity upon administration to a subject in need thereof. Within the context of the present disclosure, the term "therapeutically effective" refers to that quantity of a composition that is sufficient to delay the manifestation, arrest the progression, relieve or alleviate at least one symptom of a disorder treated by the methods of the present disclosure.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. A component can be "pharmaceutically acceptable" in the sense of being compatible with the other ingredients of a pharmaceutical formulation. It can also be suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st Edition; Lippincott Williams & Wilkins: Philadelphia, P A, 2005; Handbook of Pharmaceutical Excipients, 5th Edition"; Rowe et al., Eds., The Pharmaceutical Press and the American Pharmaceutical Association: 2005; and Handbook of Pharmaceutical Additives, 3rd Edition; Ash and Ash Eds., Gower Publishing Company: 2007; Pharmaceutical Preformulation and Formulation, Gibson Ed., CRC Press LLC: Boca Raton, F L, 2004).

The term "pharmaceutical composition" refers to a mixture of a compound disclosed herein with other chemical components, such as diluents or carriers. The pharmaceutical composition can facilitate administration of the compound to an organism. Multiple techniques of administering a compound exist in the art including, but not limited to, oral, injection, aerosol, parenteral, and topical administration.

The instant disclosure is directed to mesenchymal stem cell exosomes engineered with PD-L1: a novel cell free therapeutics to induce tolerance in autoimmune diseases and transplantation. Extracellular vesicles, such as exosomes and microvesicles (also known as shedding vesicles), carry bioactive molecules that influence the extracellular environment and the immune system. It has been shown that exosomal PD-L1 has the same membrane topology as cell surface PD-L1, with its extracellular domain exposed on the surface of the exosomes. Exosomal PD-L1 binds PD-1 in a concentration-dependent manner, and this interaction can be disrupted by PD-L1-blocking antibodies. High levels of exosomal PD-L1 may reflect the 'exhaustion' of T cells to a stage at which they can no longer be reinvigorated by anti-PD-1 treatment. Moreover, increase in exosomal PD-L1 in response to IFN-γ could enable tumour cells to adaptively inactivate CD8 T cells.

Mesenchymal stem is first isolated from healthy individuals. Once expanded, these cells can be stored for further use. These cells can then be engineered with PD-L1. To this end, PDL1 gene can be fused with Lactadherin gene. This allows the PD-L1 molecule to be inserted outside the exosomes. Upon confirmation of successful engineering, these cells are grown on bioreactor and conditioned media can be harvested to isolate exosomes. For exosome isolation, tangential flow filtration will be used to harvest and purify exosomes. These exosomes have the ability to suppress immune system in particular CD8+ and CD25+ effector cells. These effector cells are the key in pathogenesis of all autoimmune diseases and rejection processes in transplantation. Once these exosomes are generated under cGMP facilities and pass all potency and other requirements, they can be used to treat patients. In some embodiments, the mesenchymal stem cells exosomes can be engineered with PD-L1 to enhance their suppressive activity. In some embodiments, the PD-L1 engineered mesenchymal stem cell exosomes can be a treatment for all autoimmune diseases and transplantation including Type I diabetes, Multiple Sclerosis, COPD, Lupus, inflammatory bowel disease, Rheumatoid arthritis, or Psoriasis. In some embodiments, the function of the PD-L1 engineered mesenchymal stem cell exosome can be increased if engineered regulatory T cells are cultured under hypoxia conditions. In some embodiments, the PD-L1 engineered mesenchymal stem cell exosome can have the ability to suppress activated immune system in particular, CD8+CD25+ cells in patients. In some embodiments, using the platform described herein, any other cells or exosomes can be engineered to comprise PD-L1, similar to mesenchymal stem cell and mesenchymal stem cell derived exosomes. In some embodiments, the PD-L1 engineered mesenchymal stem cell exosomes can be prepared under cGMP facility. In some embodiments, the PD-L1 engineered mesenchymal stem cell exosomes can be considered as clinical-grade exosomes to treat all autoimmune disease and patients who received any organ as transplantation procedures.

The instant disclosure is directed to mesenchymal stem cell exosomes engineered with VISTA/PD-L1/CTLA-4: A novel cell free therapeutics to induce tolerance in autoimmune diseases and transplantation. Extracellular vesicles, such as exosomes and microvesicles (also known as shedding vesicles), carry bioactive molecules that influence the extracellular environment and the immune system. It has been shown that exosomal PD-L1 has the same membrane topology as cell surface PD-L1, with its extracellular domain exposed on the surface of the exosomes. Exosomal PD-L1 binds PD-1 in a concentration-dependent manner, and this interaction can be disrupted by PD-L1-blocking antibodies. High levels of exosomal PD-L1 may reflect the "exhaustion" of T cells to a stage at which they can no longer be reinvigorated by anti-PD-1 treatment. Moreover, increase in exosomal PD-L1 in response to IFN-γ can enable tumour cells to adaptively inactivate CD8 T cells. V-domain Ig suppressor of T cell activation (VISTA) is a potent negative regulator of T-cell function that is expressed on hematopoietic cells. VISTA levels are heightened within the tumor microenvironment, in which its blockade can enhance antitumor immune responses in mice. VISTA is expressed predominantly within the hematopoietic compartment with highest expression within the myeloid lineage. VISTA-Ig suppressed proliferation of T cells and blunted the production of T-cell cytokines and activation markers. VISTA is an inhibitory immune-checkpoint molecule that suppresses CD4+ and CD8+ T cell activation when expressed on antigen-presenting cells. VISTA critically regulates the inflammatory responses mediated by DCs and IL-17-producing TCRγδ+ and CD4+Th17 T cells following TLR7 stimulation. CTLA4 or CTLA-4 (cytotoxic T-lymphocyte-associated protein 4), also known as CD152 (cluster of differentiation 152), is a protein receptor that functions as an immune checkpoint and downregulates immune responses. CTLA4 is constitutively expressed in regulatory T cells but only upregulated in conventional T cells after activation—a phenomenon which is particularly notable in cancers. It acts as an "off" switch when bound to CD80 or CD86 on the surface of antigen-presenting cells.

In some embodiments, mesenchymal stem cell can be first isolated from healthy individuals. Once expanded, these cells can be stored for further use. These cells can then be engineered with VISTA/PD-L1/CTLA-4 alone or in combination. The following immune check points can be used instead or in combination of VISTA, PD-L1 and CTLA-4: PD-L2, B7-1 (CD80), B7-2 (CD86), B7-H3 (CD276), B7-H2, B7-H4 (VTCN1), HVEM (CD270, TNFRSF14), Galectin 9, Galectin3, CEACAM1 (CD66a), OX-2 (CD200), PVR (CD155), PVRL2 (Nectin-2, CD112), FGL-1, PECAM-1, TSG-6, CD47, Stabilin-1 (Clever-1), Neuropilin 1, Neuropilin 2, CD158 (family), IGSF2 (CD101), CD155, GITRL, CD137L, OX40L, LIGHT, CD70, PD-1, RGMB, CTLA-4 (CD152), BTLA, CD160, Tim-3, CD200R, TIGIT, CD112R (PVRIG), LAG-3 (CD223), PECAM-1, CD44, or SIRP alpha (CD172a).

To this end, one or combination of the immune check point genes described herein can be fused with Lactadherin gene or GPI proteins or other protein or linkers. This allows the check points protein to be inserted outside the exosomes. Upon confirmation of successful engineering, these cells are grown on bioreactor and conditioned media can be harvested to isolate exosomes. For exosome isolation, tangential flow filtration can be used to harvest and purify exosomes. These exosomes have the ability to suppress immune system in particular CD4+/CD25+; CD8+CD25+ effector cells or dendritic cells and B cells. This suppression depends on combination of check point molecules on the surface of exosomes. These effector cells are the key in pathogenesis of all autoimmune diseases and rejection processes in transplantation. Once these exosomes are generated under cGMP facilities and pass all potency and other requirements, they can be used to treat patients. In some embodiments, mesenchymal stem cells exosomes can be engineered with check point molecules to enhance their suppressive activity. This check point can be combination of VISTA/PD-L1/CTLA-4 or alone. In some embodiments, the check point can be any combination of the immune check point genes described herein. In some embodiments, the check point decorated mesenchymal stem cell exosomes can be a treatment for all autoimmune diseases and transplantation including but not limited to rheumatoid arthritis, systemic lupus erythematosus, psoriasis, type 1 diabetes mellitus, multiple sclerosis, inflammatory bowel disease, celiac disease, Crohn's disease, Graves' disease, juvenile arthritis, Lyme disease, optic neuritis, psoriatic arthritis, scleritis, scleroderma, ulcerative colitis (UC), uveitis, inflammatory eye conditions, vitiligo, COPD, or organ transplantation. In some embodiments, any other cells or exosomes can be engineered with the immune check point (similar to mesenchymal stem cell and their exosomes of human fibroblast) by utilizing the platforms described herein. In some embodiments, decorated exosomes with check point molecules can be manufactured as injectable, eye drop, nebulizer or spray, cream and topical ointment or any other form 30 accepted as a medication. In some embodiments, there exosomes can be prepared under cGMP facility and can be considered as clinical-grade exosomes to treat all autoimmune disease and patients who received any organ as transplantation procedures.

I. Compositions

Described herein, in some embodiments, is a composition comprising extracellular vesicle generated from the platforms and methods described herein. In some embodiments, the extracellular vesicle is a membrane-bound particle secreted by a cell. In some embodiments, the extracellular vesicle is a membrane-bound particle generated in vitro. In some embodiments, the extracellular vesicle is a membrane-bound particle generated ex vivo. In some embodiments, the extracellular vesicle is a membrane-bound particle generated without a cell. In some embodiments, the extracellular vesicle is exosome, microvesicle, retrovirus-like particle, apoptotic body, apoptosome, oncosome, exopher, enveloped viruses, exomere, or other very large extracellular vesicle. In some embodiments, the extracellular vesicle is exosome.

In some instances, the extracellular vesicle comprises a diameter about 1 nm to about 10,000 nm. In some instances, the extracellular vesicle comprises a diameter about 1 nm to about 5 nm, about 1 nm to about 10 nm, about 1 nm to about 20 nm, about 1 nm to about 50 nm, about 1 nm to about 100 nm, about 1 nm to about 200 nm, about 1 nm to about 500 nm, about 1 nm to about 1,000 nm, about 1 nm to about 2,000 nm, about 1 nm to about 5,000 nm, about 1 nm to about 10,000 nm, about 5 nm to about 10 nm, about 5 nm to about 20 nm, about 5 nm to about 50 nm, about 5 nm to about 100 nm, about 5 nm to about 200 nm, about 5 nm to about 500 nm, about 5 nm to about 1,000 nm, about 5 nm to about 2,000 nm, about 5 nm to about 5,000 nm, about 5 nm to about 10,000 nm, about 10 nm to about 20 nm, about 10 nm to about 50 nm, about 10 nm to about 100 nm, about 10 nm to about 200 nm, about 10 nm to about 500 nm, about 10 nm to about 1,000 nm, about 10 nm to about 2,000 nm, about 10 nm to about 5,000 nm, about 10 nm to about 10,000 nm, about 20 nm to about 50 nm, about 20 nm to about 100 nm, about 20 nm to about 200 nm, about 20 nm to about 500 nm, about 20 nm to about 1,000 nm, about 20 nm to about 2,000 nm, about 20 nm to about 5,000 nm, about 20 nm to about 10,000 nm, about 50 nm to about 100 nm, about 50 nm to about 200 nm, about 50 nm to about 500 nm, about 50 nm to about 1,000 nm, about 50 nm to about 2,000 nm, about 50 nm to about 5,000 nm, about 50 nm to about 10,000 nm, about 100 nm to about 200 nm, about 100 nm to about 500 nm, about 100 nm to about 1,000 nm, about 100 nm to about 2,000 nm, about 100 nm to about 5,000 nm, about 100 nm to about 10,000 nm, about 200 nm to about 500 nm, about 200 nm to about 1,000 nm, about 200 nm to about 2,000 nm, about 200 nm to about 5,000 nm, about 200 nm to about 10,000 nm, about 500 nm to about 1,000 nm, about 500 nm to about 2,000 nm, about 500 nm to about 5,000 nm, about 500 nm to about 10,000 nm, about 1,000 nm to about 2,000 nm, about 1,000 nm to about 5,000 nm, about 1,000 nm to about 10,000 nm, about 2,000 nm to about 5,000 nm, about 2,000 nm to about 10,000 nm, or about 5,000 nm to about 10,000 nm. In some instances, the extracellular vesicle comprises a diameter about 1 nm, about 5 nm, about 10 nm, about 20 nm, about 50 nm, about 100 nm, about 200 nm, about 500 nm, about 1,000 nm, about 2,000 nm, about 5,000 nm, or about 10,000 nm. In some instances, the extracellular vesicle comprises a diameter at least about 1 nm, about 5 nm, about 10 nm, about 20 nm, about 50 nm, about 100 nm, about 200 nm, about 500 nm, about 1,000 nm, about 2,000 nm, or about 5,000 nm. In some instances, the extracellular vesicle comprises a diameter at most about 5 nm, about 10 nm, about 20 nm, about 50 nm, about 100 nm, about 200 nm, about 500 nm, about 1,000 nm, about 2,000 nm, about 5,000 nm, or about 10,000 nm.

In some embodiments, the extracellular vesicle comprises a diameter that is at least about 1 nm to about 10,000 nm. In some embodiments, the extracellular vesicle comprises a diameter that is at least about 1 nm to about 5 nm, about 1 nm to about 10 nm, about 1 nm to about 20 nm, about 1 nm to about 50 nm, about 1 nm to about 100 nm, about 1 nm to about 200 nm, about 1 nm to about 500 nm, about 1 nm to about 1,000 nm, about 1 nm to about 2,000 nm, about 1 nm to about 5,000 nm, about 1 nm to about 10,000 nm, about 5 nm to about 10 nm, about 5 nm to about 20 nm, about 5 nm to about 50 nm, about 5 nm to about 100 nm, about 5 nm to about 200 nm, about 5 nm to about 500 nm, about 5 nm to about 1,000 nm, about 5 nm to about 2,000 nm, about 5 nm to about 5,000 nm, about 5 nm to about 10,000 nm, about 10 nm to about 20 nm, about 10 nm to about 50 nm, about 10 nm to about 100 nm, about 10 nm to about 200 nm, about 10 nm to about 500 nm, about 10 nm to about 1,000 nm, about 10 nm to about 2,000 nm, about 10 nm to about 5,000 nm, about 10 nm to about 10,000 nm, about 20 nm to about 50 nm, about 20 nm to about 100 nm, about 20 nm to about 200 nm, about 20 nm to about 500 nm, about 20 nm to about 1,000 nm, about 20 nm to about 2,000 nm, about 20 nm to about 5,000 nm, about 20 nm to about 10,000 nm, about 50 nm to about 100 nm, about 50 nm to about 200 nm, about 50 nm to about 500 nm, about 50 nm to about 1,000 nm, about 50 nm to about 2,000 nm, about 50 nm to about 5,000 nm, about 50 nm to about 10,000 nm, about 100 nm to about 200 nm, about 100 nm to about 500 nm, about 100 nm to about 1,000 nm, about 100 nm to about 2,000 nm, about 100 nm to about 5,000 nm, about 100 nm to about 10,000 nm, about 200 nm to about 500 nm, about 200 nm to about 1,000 nm, about 200 nm to about 2,000 nm, about 200 nm to about 5,000 nm, about 200 nm to about 10,000 nm, about 500 nm to about 1,000 nm, about 500 nm to about 2,000 nm, about 500 nm to about 5,000 nm, about 500 nm to about 10,000 nm, about 1,000 nm to about 2,000 nm, about 1,000 nm to about 5,000 nm, about 1,000 nm to about 10,000 nm, about 2,000 nm to about 5,000 nm, about 2,000 nm to about 10,000 nm, or about 5,000 nm to about 10,000 nm. In some embodiments, the extracellular vesicle comprises a diameter that is at least about 1 nm, about 5 nm, about 10 nm, about 20 nm, about 50 nm, about 100 nm, about 200 nm, about 500 nm, about 1,000 nm, about 2,000 nm, about 5,000 nm, or about 10,000 nm. In some embodiments, the extracellular vesicle comprises a diameter that is at least at least about 1 nm, about 5 nm, about 10 nm, about 20 nm, about 50 nm, about 100 nm, about 200 nm, about 500 nm, about 1,000 nm, about 2,000 nm, or about 5,000 nm. In some embodiments, the extracellular vesicle comprises a diameter that is at least at most about 5 nm, about 10 nm, about 20 nm, about 50 nm, about 100 nm, about 200 nm, about 500 nm, about 1,000 nm, about 2,000 nm, about 5,000 nm, or about 10,000 nm.

In some embodiments, the composition comprises a heterogenous population of a plurality of extracellular vesicles. In some embodiments, the heterogeneous population of the extracellular vesicles comprises a diameter between about 1 nm to about 10,000 nm. In some embodiments, the heterogeneous population of the extracellular vesicles comprises a diameter between about 1 nm to about 5 nm, about 1 nm to about 10 nm, about 1 nm to about 20 nm, about 1 nm to about 50 nm, about 1 nm to about 100 nm, about 1 nm to about 200 nm, about 1 nm to about 500 nm, about 1 nm to about 1,000 nm, about 1 nm to about 2,000 nm, about 1 nm to about 5,000 nm, about 1 nm to about 10,000 nm, about 5 nm to about 10 nm, about 5 nm to about 20 nm, about 5 nm to about 50 nm, about 5 nm to about 100 nm, about 5 nm to about 200 nm, about 5 nm to about 500 nm, about 5 nm to about 1,000 nm, about 5 nm to about 2,000 nm, about 5 nm to about 5,000 nm, about 5 nm to about 10,000 nm, about 10 nm to about 20 nm, about 10 nm to about 50 nm, about 10 nm to about 100 nm, about 10 nm to about 200 nm, about 10 nm to about 500 nm, about 10 nm to about 1,000 nm, about 10 nm to about 2,000 nm, about 10 nm to about 5,000 nm, about 10 nm to about 10,000 nm, about 20 nm to about 50 nm, about 20 nm to about 100 nm, about 20 nm to about 200 nm, about 20 nm to about 500 nm, about 20 nm to about 1,000 nm, about 20 nm to about 2,000 nm, about 20 nm to about 5,000 nm, about 20 nm to about 10,000 nm, about 50 nm to about 100 nm, about 50 nm to about 200 nm, about 50 nm to about 500 nm, about 50 nm to about 1,000 nm, about 50 nm to about 2,000 nm, about 50 nm to about 5,000 nm, about 50 nm to about 10,000 nm, about 100 nm to about 200 nm, about 100 nm to about 500 nm, about 100 nm to about 1,000 nm, about 100 nm to about 2,000 nm, about 100 nm to about 5,000 nm, about 100 nm to about 10,000 nm, about 200 nm to about 500 nm, about 200 nm to about 1,000 nm, about 200 nm to about 2,000 nm, about 200 nm to about 5,000 nm, about 200 nm to about 10,000 nm, about 500 nm to about 1,000 nm, about 500 nm to about 2,000 nm, about 500 nm to about 5,000 nm, about 500 nm to about 10,000 nm, about 1,000 nm to about 2,000 nm, about 1,000 nm to about 5,000 nm, about 1,000 nm to about 10,000 nm, about 2,000 nm to about 5,000 nm, about 2,000 nm to about 10,000 nm, or about 5,000 nm to about 10,000 nm. In some embodiments, the heterogeneous population of the extracellular vesicles comprises a diameter between about 1 nm, about 5 nm, about 10 nm, about 20 nm, about 50 nm, about 100 nm, about 200 nm, about 500 nm, about 1,000 nm, about 2,000 nm, about 5,000 nm, or about 10,000 nm. In some embodiments, the heterogeneous population of the extracellular vesicles comprises a diameter between at least about 1 nm, about 5 nm, about 10 nm, about 20 nm, about 50 nm, about 100 nm, about 200 nm, about 500 nm, about 1,000 nm, about 2,000 nm, or about 5,000 nm. In some embodiments, the heterogeneous population of the extracellular vesicles comprises a diameter between at most about 5 nm, about 10 nm, about 20 nm, about 50 nm, about 100 nm, about 200 nm, about 500 nm, about 1,000 nm, about 2,000 nm, about 5,000 nm, or about 10,000 nm.

In some embodiments, the heterogeneous population of the extracellular vesicles comprises a diameter that is at least about 1 nm to about 10,000 nm. In some embodiments, the heterogeneous population of the extracellular vesicles comprises a diameter that is at least about 1 nm to about 5 nm, about 1 nm to about 10 nm, about 1 nm to about 20 nm, about 1 nm to about 50 nm, about 1 nm to about 100 nm, about 1 nm to about 200 nm, about 1 nm to about 500 nm, about 1 nm to about 1,000 nm, about 1 nm to about 2,000 nm, about 1 nm to about 5,000 nm, about 1 nm to about 10,000 nm, about 5 nm to about 10 nm, about 5 nm to about 20 nm, about 5 nm to about 50 nm, about 5 nm to about 100 nm, about 5 nm to about 200 nm, about 5 nm to about 500 nm, about 5 nm to about 1,000 nm, about 5 nm to about 2,000 nm, about 5 nm to about 5,000 nm, about 5 nm to about 10,000 nm, about 10 nm to about 20 nm, about 10 nm to about 50 nm, about 10 nm to about 100 nm, about 10 nm to about 200 nm, about 10 nm to about 500 nm, about 10 nm to about 1,000 nm, about 10 nm to about 2,000 nm, about 10 nm to about 5,000 nm, about 10 nm to about 10,000 nm, about 20 nm to about 50 nm, about 20 nm to about 100 nm, about 20 nm to about 200 nm, about 20 nm to about 500 nm, about 20 nm to about 1,000 nm, about 20 nm to about 2,000 nm, about 20 nm to about 5,000 nm, about 20 nm to about 10,000 nm, about 50 nm to about 100 nm, about 50 nm to about 200 nm, about 50 nm to about 500 nm, about 50 nm to about 1,000 nm, about 50 nm to about 2,000 nm, about 50 nm to about 5,000 nm, about 50 nm to about 10,000 nm, about 100 nm to about 200 nm, about 100 nm to about 500 nm, about 100 nm to about 1,000 nm, about 100 nm to about 2,000 nm, about 100 nm to about 5,000 nm, about 100 nm to about 10,000 nm, about 200 nm to about 500 nm, about 200 nm to about 1,000 nm, about 200 nm to about 2,000 nm, about 200 nm to about 5,000 nm, about 200 nm to about 10,000 nm, about 500 nm to about 1,000 nm, about 500 nm to about 2,000 nm, about 500 nm to about 5,000 nm, about 500 nm to about 10,000 nm, about 1,000 nm to about 2,000 nm, about 1,000 nm to about 5,000 nm, about 1,000 nm to about 10,000 nm, about 2,000 nm to about 5,000 nm, about 2,000 nm to about 10,000 nm, or about 5,000 nm to about 10,000 nm. In some embodiments, the heterogeneous population of the extracellular vesicles comprises a diameter that is at least about 1 nm, about 5 nm, about 10 nm, about 20 nm, about 50 nm, about 100 nm, about 200 nm, about 500 nm, about 1,000 nm, about 2,000 nm, about 5,000 nm, or about 10,000 nm. In some embodiments, the heterogeneous population of the extracellular vesicles comprises a diameter that is at least at least about 1 nm, about 5 nm, about 10 nm, about 20 nm, about 50 nm, about 100 nm, about 200 nm, about 500 nm, about 1,000 nm, about 2,000 nm, or about 5,000 nm. In some embodiments, the heterogeneous population of the extracellular vesicles comprises a diameter that is at least at most about 5 nm, about 10 nm, about 20 nm, about 50 nm, about 100 nm, about 200 nm, about 500 nm, about 1,000 nm, about 2,000 nm, about 5,000 nm, or about 10,000 nm.

In some embodiments, the composition comprises a homogeneous population of a plurality of extracellular vesicles. In some embodiments, the homogeneous population of the extracellular vesicles comprises a diameter between about 10 nm to about 150 nm. In some embodiments, the homogeneous population of the extracellular vesicles comprises a diameter between about 10 nm to about 30 nm, about 10 nm to about 40 nm, about 10 nm to about 50 nm, about 10 nm to about 60 nm, about 10 nm to about 70 nm, about 10 nm to about 80 nm, about 10 nm to about 90 nm, about 10 nm to about 100 nm, about 10 nm to about 110 nm, about 10 nm to about 120 nm, about 10 nm to about 150 nm, about 30 nm to about 40 nm, about 30 nm to about 50 nm, about 30 nm to about 60 nm, about 30 nm to about 70 nm, about 30 nm to about 80 nm, about 30 nm to about 90 nm, about 30 nm to about 100 nm, about 30 nm to about 110 nm, about 30 nm to about 120 nm, about 30 nm to about 150 nm, about 40 nm to about 50 nm, about 40 nm to about 60 nm, about 40 nm to about 70 nm, about 40 nm to about 80 nm, about 40 nm to about 90 nm, about 40 nm to about 100 nm, about 40 nm to about 110 nm, about 40 nm to about 120 nm, about 40 nm to about 150 nm, about 50 nm to about 60 nm, about 50 nm to about 70 nm, about 50 nm to about 80 nm, about 50 nm to about 90 nm, about 50 nm to about 100 nm, about 50 nm to about 110 nm, about 50 nm to about 120 nm, about 50 nm to about 150 nm, about 60 nm to about 70 nm, about 60 nm to about 80 nm, about 60 nm to about 90 nm, about 60 nm to about 100 nm, about 60 nm to about 110 nm, about 60 nm to about 120 nm, about 60 nm to about 150 nm, about 70 nm to about 80 nm, about 70 nm to about 90 nm, about 70 nm to about 100 nm, about 70 nm to about 110 nm, about 70 nm to about 120 nm, about 70 nm to about 150 nm, about 80 nm to about 90 nm, about 80 nm to about 100 nm, about 80 nm to about 110 nm, about 80 nm to about 120 nm, about 80 nm to about 150 nm, about 90 nm to about 100 nm, about 90 nm to about 110 nm, about 90 nm to about 120 nm, about 90 nm to about 150 nm, about 100 nm to about 110 nm, about 100 nm to about 120 nm, about 100 nm to about 150 nm, about 110 nm to about 120 nm, about 110 nm to about 150 nm, or about 120 nm to about 150 nm. In some embodiments, the homogeneous population of the extracellular vesicles comprises a diameter between about 10 nm, about 30 nm, about 40 nm, about 50 nm, about 60 nm, about 70 nm, about 80 nm, about 90 nm, about 100 nm, about 110 nm, about 120 nm, or about 150 nm. In some embodiments, the homogeneous population of the extracellular vesicles comprises a diameter between about at least about 10 nm, about 30 nm, about 40 nm, about 50 nm, about 60 nm, about 70 nm, about 80 nm, about 90 nm, about 100 nm, about 110 nm, or about 120 nm. In some embodiments, the homogeneous population of the extracellular vesicles comprises a diameter between about at most about 30 nm, about 40 nm, about 50 nm, about 60 nm, about 70 nm, about 80 nm, about 90 nm, about 100 nm, about 110 nm, about 120 nm, or about 150 nm.

Immune Checkpoint Moiety

Discredited herein, in some embodiments, are compositions comprising extracellular vesicles comprising immune checkpoint moiety. In some embodiments, the extracellular vesicle comprises a plurality of immune checkpoint moieties, where the immune check point moieties can be the same or different. In some embodiments, the immune checkpoint moiety is encapsulated by the extracellular vesicle. In some embodiments, the immune checkpoint moiety is expressed on the surface of the extracellular vesicle. In some embodiments, the immune checkpoint moiety is secreted by the extracellular vesicle. In some embodiments, the immune checkpoint moiety is encapsulated by the extracellular vesicle. In some embodiments, the immune checkpoint moiety is expressed on the surface of the extracellular vesicle; is secreted by the extracellular vesicle; is delivered by the extracellular to a target cell or a target microenvironment; or a combination thereof. In some embodiments, the immune checkpoint moiety comprises therapeutic properties for treating a disease or disorder. In some embodiments, the disease or disorder is an autoimmune disease. In some embodiments, the composition comprising extracellular vesicle comprising the immune checkpoint moiety can be administered to a subject to treat a disease or disorder.

In some embodiments, the immune checkpoint moiety comprises a polypeptide comprising a peptide sequence encoding VISTA, PD-L1, CTLA-4, PD-L2, B7-1 (CD80), B7-2 (CD86), B7-H3 (CD276), B7-H2, B7-H3, B7-H4 (VTCN1), IDO, KIR, LAG3, A2AR, HVEM (CD270, TNFRSF14), Galectin 9, Galectin3, CEACAM1 (CD66a), OX-2 (CD200), PVR (CD155), PVRL2 (Nectin-2, CD112), FGL-1, PECAM-1, TSG-6, CD47, Stabilin-1 (Clever-1), Neuropilin 1, Neuropilin 2, CD158 (family), IGSF2 (CD101), CD155, GITRL, CD137L, OX40L, LIGHT, CD70, PD-1, RGMB, CTLA-4 (CD152), BTLA, CD160, Tim-3, CD200R, TIGIT, CD112R (PVRIG), LAG-3 (CD223), PECAM-1, CD44, or SIRP alpha (CD172a). In some embodiments, the immune checkpoint moiety comprises a peptide sequence encoding VISTA or a variation thereof or a fragment thereof. In some embodiments, the immune checkpoint moiety comprises a peptide sequence that is at least 50%, 55%, 60%, 65%, 70%, 75%, 80%. 85%. 90%, 95%, or 99% identical to SEQ ID NO: 1. In some embodiments, the immune checkpoint moiety comprises a peptide sequence that is 100% identical to SEQ ID NO: 1 (Table 1). In some embodiments, the immune checkpoint moiety comprises a peptide sequence encoding PD-L1 or a variation thereof or a fragment thereof. In some embodiments, the immune checkpoint moiety comprises a peptide sequence that is at least 50%, 55%, 60%, 65%, 70%, 75%, 80%. 85%. 90%, 95%, or 99% identical to SEQ ID NO: 2. In some embodiments, the immune checkpoint moiety comprises a peptide sequence that is 100% identical to SEQ ID NO: 2 (Table 1). In some embodiments, the immune checkpoint moiety comprises a peptide sequence encoding CTLA-4 or a variation thereof or a fragment thereof. In some embodiments, the immune checkpoint moiety comprises a peptide sequence that is at least 50%, 55%, 60%, 65%, 70%, 75%, 80%. 85%. 90%, 95%, or 99% identical to SEQ ID NO: 3. In some embodiments, the immune checkpoint moiety comprises a peptide sequence that is 100% identical to SEQ ID NO: 3 (Table 1).

TABLE 1

Peptide Sequence of VISTA, CTLA-4, PD-L1, and CTLA-4

| SEQ ID NO | |
|---|---|
| | VISTA, Accession Number Q9H7M9 |
| 1 | MGVPTALEAGSWRWGSLLFALFLAASLGPVAAFKVATPYSLYVCPEGQNVTLTCRLLGPVDKGHDVT FYKTWYRSSRGEVQTCSERRPIRNLTFQDLHLHHGGHQAANTSHDLAQRHGLESASDHHGNFSITM RNLTLLDSGLYCCLVVEIRHHHSEHRVHGAMELQVQTGKDAPSNCVVYPSSSQDSENITAAALATGAC IVGILCLPLILLLVYKQRQAASNRRAQELVRMDSNIQGIENPGFEASPPAQGIPEAKVRHPLSYVAQRQ PSESGRHLLSEPSTPLSPPGPGDVFFPSLDPVPDSPNFEVI |

TABLE 1-continued

Peptide Sequence of VISTA, CTLA-4, PD-L1, and CTLA-4

| SEQ ID NO | |
|---|---|
| | PD-L1 (CD274), Accession Number Q9NZQ7 |
| 2 | MRIFAVFIFMTYWHLLNAFTVTVPKDLYVVEYGSNMTIECKFPVEKQLDLAALIVYWEMEDKNIIQFVHG<br>EEDLKVQHSSYRQRARLLKDQLSLGNAALQITDVKLQDAGVYRCMISYGGADYKRITVKVNAPYNKINQR<br>ILVVDPVTSEHELTCQAEGYPKAEVIWTSSDHQVLSGKTTTTNSKREEKLFNVTSTLRINTTTNEIFYCT<br>FRRLDPEENHTAELVIPELPLAHPPNERTHLVILGAILLCLGVALTFIFRLRKGRMMDVKKCGIQDTNSK<br>KQSDTHLEET |
| | CTLA-4, Accession Number P16410 |
| 3 | MACLGFQRHKAQLNLATRTWPCTLLFFLLFIPVFCKAMHVAQPAVVLASSRGIASFVCEYASPGKATEVR<br>VTVLRQADSQVTEVCAATYMMGNELTFLDDSICTGTSSGNQVNLTIQGLRAMDTGLYICKVELMYPPPYY<br>LGIGNGTQIYVIDPEPCPDSDFLLWILAAVSSGLFFYSFLLTAVSLSKMLKKRSPLTTGVYVKMPPTEPE<br>CEKQFQPYFIPIN |

In some embodiments, the immune checkpoint moiety comprises a heterologous polynucleotide. In some embodiments, the heterologous polynucleotide comprises mRNA, rRNA, SRP RNA, tRNA, tmRNA, snRNA, snoRNA, gRNA, aRNA, crRNA, lncRNA, miRNA, ncRNA, piRNA, siRNA, and shRNA. In some cases, the heterologous polynucleotide comprises mRNA. In some embodiments, the heterologous polynucleotide encodes a nucleic sequence of VISTA, PD-L1, CTLA-4, PD-L2, B7-1 (CD80), B7-2 (CD86), B7-H3 (CD276), B7-H2, B7-H3, B7-H4 (VTCN1), IDO, KIR, LAG3, A2AR, HVEM (CD270, TNFRSF14), Galectin 9, Galectin3, CEACAM1 (CD66a), OX-2 (CD200), PVR (CD155), PVRL2 (Nectin-2, CD112), FGL-1, PECAM-1, TSG-6, CD47, Stabilin-1 (Clever-1), Neuro-pilin 1, Neuropilin 2, CD158 (family), IGSF2 (CD101), CD155, GITRL, CD137L, OX40L, LIGHT, CD70, PD-1, RGMB, CTLA-4 (CD152), BTLA, CD160, Tim-3, CD200R, TIGIT, CD112R (PVRIG), LAG-3 (CD223), PECAM-1, CD44, or SIRP alpha (CD172a). In some embodiments, the immune checkpoint moiety comprises a heterologous polynucleotide encoding VISTA. In some embodiments, the immune checkpoint moiety comprises a heterologous polynucleotide encoding PD-L1. In some embodiments, the immune checkpoint moiety comprises a heterologous polynucleotide encoding CTLA-4.

In some embodiments, the immune checkpoint moiety comprises a heterologous polynucleotide encoding a cytokine. In some embodiments, the immune checkpoint moiety comprises a polypeptide comprising a peptide sequence of the cytokine. Exemplary cytokines that can be utilized as the immune check point moiety includes 4-1BBL, acylation stimulating protein, adipokine, albinterferon, APRIL, Arh, BAFF, Bcl-6, CCL1, CCL1/TCA3, CCL11, CCL12/MCP-5, CCL13/MCP-4, CCL14, CCL15, CCL16, CCL17/TARC, CCL18, CCL19, CCL2, CCL2/MCP-1, CCL20, CCL21, CCL22/1 VDC, CCL23, CCL24, CCL25, CCL26, CCL27, CCL28, CCL3, CCL3L3, CCL4, CCL4L1/LAG-1, CCL5, CCL6, CCL7, CCL8, CCL9, CCR10, CCR3, CCR4, CCR5, CCR6, CCR7, CCR8, CD153, CD154, CD178, CD40LG, CD70, CD95L/CD178, Cerberus (protein), chemokines, CLCF1, CNTF, colony-stimulating factor, common b chain (CD131), common g chain (CD132), CX3CL1, CX3CR1, CXCL1, CXCL10, CXCL11, CXCL12, CXCL13, CXCL14, CXCL15, CXCL16, CXCL17, CXCL2, CXCL2/MIP-2, CXCL3, CXCL4, CXCL5, CXCL6, CXCL7, CXCL9, CXCR3, CXCR4, CXCR5, EDA-A1, Epo, erythropoietin, FAM19A1, FAM19A2, FAM19A3, FAM19A4, FAM19A5, Flt-3L, FMS-like tyrosine kinase 3 ligand, Foxp3, GATA-3, GcMAF, G-CSF, GITRL, GM-CSF, granulocyte colony-stimulating factor, granulocyte-macrophage colony-stimulating factor, hepatocyte growth factor, IFNA1, IFNA10, IFNA13, IFNA14, IFNA2, IFNA4, IFNA5/IFNaG, IFNA7, IFNA8, IFNB1, IFNE, IFNG, IFNZ, IFN-α, IFN-β, IFN-γ, IFNω/IFNW1, IL-1, IL-10, IL-10 family, IL-10-like, IL-11, IL-12, IL-13, IL-14, IL-15, IL-16, IL-17, IL-17 family, IL-17A-F, IL-18, IL-18BP, IL-19, IL-1A, IL-1B, IL-1F10, IL-1F3/IL-1RA, IL-1F5, IL-1F6, IL-1F7, IL-1F8, IL-1F9, IL-1-like, IL-1RA, IL-1RL2, IL-1α, IL-1β, IL-2, IL-20, IL-21, IL-22, IL-23, IL-24, IL-28A, IL-28B, IL-29, IL-3, IL-31, IL-33, IL-35, IL-4, IL-5, IL-6, IL-6-like, IL-7, IL-8/CXCL8, IL-9, inflammasome, interferome, interferon, interferon beta-1a, interferon beta-1b, interferon gamma, interferon type I, interferon type II, interferon type III, interferons, interleukin, interleukin 1 receptor antagonist, Interleukin 8, IRF4, Leptin, leukemia inhibitory factor (LIF), leukocyte-promoting factor, LIGHT, LTA/TNFB, LT-β, lymphokine, lymphotoxin, lymphotoxin alpha, lymphotoxin beta, macrophage colony-stimulating factor, macrophage inflammatory protein, macrophage-activating factor, M-CSF, MHC class III, miscellaneous hematopoietins, monokine, MSP, myokine, myonectin, nicotinamide phosphoribosyltransferase, oncostatin M (OSM), oprelvekin, OX40L, platelet factor 4, promegapoietin, RANKL, SCF, STAT3, STAT4, STATE, stromal cell-derived factor 1, TALL-1, TBX21, TGF-α, TGF-β, TGF-β1, TGF-β2, TGF-β3, TNF, TNFSF10, TNFSF11, TNFSF12, TNFSF13, TNFSF14, TNFSF15, TNFSF4, TNFSF8, TNF-α, TNF-β, Tpo, TRAIL, TRANCE, TWEAK, vascular endothelial growth inhibitor, XCL1, or XCL2.

In some embodiments, the immune checkpoint moiety can be complexed with the transmembrane moiety described herein. In some embodiments, the immune checkpoint moiety can be non-covalently complexed with the transmembrane moiety described herein. In some embodiments, the immune checkpoint moiety can be covalently complexed with the transmembrane moiety described herein. In some embodiments, the immune checkpoint moiety can be expressed as part of a fusion protein comprising both the immune checkpoint moiety and the transmembrane moiety. In some embodiments, the immune checkpoint moiety can be expressed as part of a fusion protein comprising both the immune checkpoint moiety and a fragment of the transmembrane moiety, In some embodiments, the N-terminus of the immune checkpoint moiety can be fused to the transmembrane moiety. In some embodiments, the C-terminus of the immune checkpoint moiety can be fused to the transmembrane moiety described herein. In some embodiments, the immune checkpoint moiety can be fused and flanked by the transmembrane moiety on both N and C-terminus of the immune checkpoint moiety. For example, the immune checkpoint moiety can be inserted into a transmembrane moiety as part of a fusion peptide, where the N-terminus of the fusion peptide comprises a fragment of the transmembrane moiety, followed by the immune checkpoint moiety (or a variation there or a fragment thereof), and followed by the C-terminus of the fusion peptide comprising another fragment of the transmembrane moiety. In some embodiments, the immune checkpoint moiety comprises the fusion peptide, where the immune checkpoint moiety is fused to the transmembrane moiety. In some embodiments, the immune checkpoint moiety comprises the immune checkpoint moiety complexed with the transmembrane moiety. In some embodiments, the immune checkpoint moiety comprises the immune checkpoint moiety non-covalently complexed with the transmembrane moiety. In some embodiments, the immune checkpoint moiety comprises the immune checkpoint moiety covalently complexed with the transmembrane moiety.

In some embodiments, the extracellular vesicle comprises a plurality of the immune checkpoint moiety described herein. In some embodiments, the plurality of the immune checkpoint moieties are encapsulated in the extracellular vesicle. In some embodiments, the extracellular vesicle encapsulates at least one, ten, 100, 500, 1,000, 5,000, 10,000, 50,000, 100,000, 500,000, 1,000,000, 5,000,000, or more units of the immune checkpoint moiety. In some embodiments, the extracellular vesicle delivers the encapsulated immune checkpoint to a target cell or a target microenvironment.

In some embodiments, the extracellular vesicle secretes a plurality of the immune checkpoint moiety described herein. In some embodiments, the extracellular vesicle secretes at least one, ten, 100, 500, 1,000, 5,000, 10,000, 50,000, 100,000, 500,000, 1,000,000, 5,000,000, or more units of the immune checkpoint moiety. In some embodiments, the extracellular vesicle secretes the immune checkpoint moiety to a target cell or a target environment.

In some embodiments, the plurality of the immune checkpoint moiety is expressed on the surface of the extracellular vesicle. In some embodiments, the plurality of the immune checkpoint moieties are expressed as part of the fusion peptide comprising immune checkpoint moiety and transmembrane moiety. In some instances, the extracellular vesicle comprising the immune checkpoint moiety expressed on the surface of the extracellular vesicle contacts with a target cell or a target environment.

In some embodiments, the number of units of the immune checkpoint moiety that can be expressed on the surface of the extracellular vesicle is limited by a theoretical maximum as determined by the ratio between: the dimensions of the extracellular vesicle; and the dimensions of the expressed immune checkpoint moiety or the expressed fusion peptide comprising the immune checkpoint moiety. In some embodiments, the platforms and methods described herein can generate and select for an extracellular vesicle expressing a number of units of immune checkpoint moiety that is at least 30%, 35%, 40%, 45%, 50%, 55%, 60%, 65%, 70%, 75%, 80%, 85%, 90%, 95%, or 99% of the theoretical maximum of number of units of immune checkpoint moiety that can expressed on the surface of the extracellular vesicle. In some embodiments, the platforms and methods described herein can generate and select for a homogenous population of extracellular vesicles expressing a number of units of immune checkpoint moiety that is at least 30%, 35%, 40%, 45%, 50%, 55%, 60%, 65%, 70%, 75%, 80%, 85%, 90%, 95%, or 99% of the theoretical maximum of number of units of immune checkpoint moiety that can expressed on the surface of the extracellular vesicle. In some embodiments, the platforms and methods described herein can generate and select for a homogenous population of extracellular vesicles expressing a number of units of immune checkpoint moiety on the surface of the extracellular vesicle that is at least 30% of the theoretical maximum number of units of immune checkpoint moiety that can be expressed on the surface of the extracellular vesicle. In some embodiments, the platforms and methods described herein can generate and select for a homogenous population of extracellular vesicles expressing a number of units of immune checkpoint moiety on the surface of the extracellular vesicle that is at least 70% of the theoretical maximum number of units of immune checkpoint moiety that can be expressed on the surface of the extracellular vesicle. In some embodiments, the platforms and methods described herein can generate and select for a homogenous population of extracellular vesicles expressing a number of units of immune checkpoint moiety on the surface of the extracellular vesicle that is at least 75% of the theoretical maximum number of units of immune checkpoint moiety that can be expressed on the surface of the extracellular vesicle. In some embodiments, the platforms and methods described herein can generate and select for a homogenous population of extracellular vesicles expressing a number of units of immune checkpoint moiety on the surface of the extracellular vesicle that is at least 80% of the theoretical maximum number of units of immune checkpoint moiety that can be expressed on the surface of the extracellular vesicle. In some embodiments, the platforms and methods described herein can generate and select for a homogenous population of extracellular vesicles expressing a number of units of immune checkpoint moiety on the surface of the extracellular vesicle that is at least 85% of the theoretical maximum number of units of immune checkpoint moiety that can be expressed on the surface of the extracellular vesicle. In some embodiments, the platforms and methods described herein can generate and select for a homogenous population of extracellular vesicles expressing a number of units of immune checkpoint moiety on the surface of the extracellular vesicle that is at least 90% of the theoretical maximum number of units of immune checkpoint moiety that can be expressed on the surface of the extracellular vesicle. In some embodiments, the platforms and methods described herein can generate and select for a homogenous population of extracellular vesicles expressing a number of units of immune checkpoint moiety on the surface of the extracellular vesicle that is at least 95% of the theoretical maximum number of units of immune checkpoint moiety that can be expressed on the surface of the extracellular vesicle. In some embodiments, the platforms and methods described herein can generate and select for a homogenous population of extracellular vesicles expressing a number of units of immune checkpoint moiety on the surface of the extracellular vesicle that is at least 95% of the theoretical maximum number of units of immune checkpoint moiety that can be expressed on the surface of the extracellular vesicle.

In some embodiments, each extracellular vesicle expresses a number of units of immune checkpoint moiety on the surface of the extracellular vesicle, where the number can be about 5 units to about 1,000,000 units. In some embodiments, each extracellular vesicle expresses a number of units of immune checkpoint moiety on the surface of the extracellular vesicle, where the number can be about 5 units to about 10 units, about 5 units to about 50 units, about 5 units to about 100 units, about 5 units to about 500 units, about 5 units to about 1,000 units, about 5 units to about 5,000 units, about 5 units to about 10,000 units, about 5 units to about 50,000 units, about 5 units to about 100,000 units, about 5 units to about 500,000 units, about 5 units to about 1,000,000 units, about 10 units to about 50 units, about 10 units to about 100 units, about 10 units to about 500 units, about 10 units to about 1,000 units, about 10 units to about 5,000 units, about 10 units to about 10,000 units, about 10 units to about 50,000 units, about 10 units to about 100,000 units, about 10 units to about 500,000 units, about 10 units to about 1,000,000 units, about 50 units to about 100 units, about 50 units to about 500 units, about 50 units to about 1,000 units, about 50 units to about 5,000 units, about 50 units to about 10,000 units, about 50 units to about 50,000 units, about 50 units to about 100,000 units, about 50 units to about 500,000 units, about 50 units to about 1,000,000 units, about 100 units to about 500 units, about 100 units to about 1,000 units, about 100 units to about 5,000 units, about 100 units to about 10,000 units, about 100 units to about 50,000 units, about 100 units to about 100,000 units, about 100 units to about 500,000 units, about 100 units to about 1,000,000 units, about 500 units to about 1,000 units, about 500 units to about 5,000 units, about 500 units to about 10,000 units, about 500 units to about 50,000 units, about 500 units to about 100,000 units, about 500 units to about 500,000 units, about 500 units to about 1,000,000 units, about 1,000 units to about 5,000 units, about 1,000 units to about 10,000 units, about 1,000 units to about 50,000 units, about 1,000 units to about 100,000 units, about 1,000 units to about 500,000 units, about 1,000 units to about 1,000,000 units, about 5,000 units to about 10,000 units, about 5,000 units to about 50,000 units, about 5,000 units to about 100,000 units, about 5,000 units to about 500,000 units, about 5,000 units to about 1,000,000 units, about 10,000 units to about 50,000 units, about 10,000 units to about 100,000 units, about 10,000 units to about 500,000 units, about 10,000 units to about 1,000,000 units, about 50,000 units to about 100,000 units, about 50,000 units to about 500,000 units, about 50,000 units to about 1,000,000 units, about 100,000 units to about 500,000 units, about 100,000 units to about 1,000,000 units, or about 500,000 units to about 1,000,000 units. In some embodiments, each extracellular vesicle expresses a number of units of immune checkpoint moiety on the surface of the extracellular vesicle, where the number can be about 5 units, about 10 units, about 50 units, about 100 units, about 500 units, about 1,000 units, about 5,000 units, about 10,000 units, about 50,000 units, about 100,000 units, about 500,000 units, or about 1,000,000 units. In some embodiments, each extracellular vesicle expresses a number of units of immune checkpoint moiety on the surface of the extracellular vesicle, where the number can be at least about 5 units, about 10 units, about 50 units, about 100 units, about 500 units, about 1,000 units, about 5,000 units, about 10,000 units, about 50,000 units, about 100,000 units, or about 500,000 units. In some embodiments, each extracellular vesicle expresses a number of units of immune checkpoint moiety on the surface of the extracellular vesicle, where the number can be at most about 10 units, about 50 units, about 100 units, about 500 units, about 1,000 units, about 5,000 units, about 10,000 units, about 50,000 units, about 100,000 units, about 500,000 units, or about 1,000,000 units.

In some embodiments, the composition described herein comprises a heterogenous population of extracellular vesicles expressing any number of units of the immune checkpoint moiety described herein on the surface of the extracellular vesicles. In some embodiments, the composition described herein comprises a homogeneous population of extracellular vesicles expressing a range of number of units of the immune checkpoint moiety on the surface of the extracellular vesicles. In some embodiments, the homogeneous population of extracellular vesicles expresses a number of units of the immune checkpoint moiety that is at least about 5 units to about 1,000,000 units. In some embodiments, the homogeneous population of extracellular vesicles expresses a number of units of the immune checkpoint moiety that is at least about 5 units to about 10 units, about 5 units to about 50 units, about 5 units to about 100 units, about 5 units to about 500 units, about 5 units to about 1,000 units, about 5 units to about 5,000 units, about 5 units to about 10,000 units, about 5 units to about 50,000 units, about 5 units to about 100,000 units, about 5 units to about 500,000 units, about 5 units to about 1,000,000 units, about 10 units to about 50 units, about 10 units to about 100 units, about 10 units to about 500 units, about 10 units to about 1,000 units, about 10 units to about 5,000 units, about 10 units to about 10,000 units, about 10 units to about 50,000 units, about 10 units to about 100,000 units, about 10 units to about 500,000 units, about 10 units to about 1,000,000 units, about 50 units to about 100 units, about 50 units to about 500 units, about 50 units to about 1,000 units, about 50 units to about 5,000 units, about 50 units to about 10,000 units, about 50 units to about 50,000 units, about 50 units to about 100,000 units, about 50 units to about 500,000 units, about 50 units to about 1,000,000 units, about 100 units to about 500 units, about 100 units to about 1,000 units, about 100 units to about 5,000 units, about 100 units to about 10,000 units, about 100 units to about 50,000 units, about 100 units to about 100,000 units, about 100 units to about 500,000 units, about 100 units to about 1,000,000 units, about 500 units to about 1,000 units, about 500 units to about 5,000 units, about 500 units to about 10,000 units, about 500 units to about 50,000 units, about 500 units to about 100,000 units, about 500 units to about 500,000 units, about 500 units to about 1,000,000 units, about 1,000 units to about 5,000 units, about 1,000 units to about 10,000 units, about 1,000 units to about 50,000 units, about 1,000 units to about 100,000 units, about 1,000 units to about 500,000 units, about 1,000 units to about 1,000,000 units, about 5,000 units to about 10,000 units, about 5,000 units to about 50,000 units, about 5,000 units to about 100,000 units, about 5,000 units to about 500,000 units, about 5,000 units to about 1,000,000 units, about 10,000 units to about 50,000 units, about 10,000 units to about 100,000 units, about 10,000 units to about 500,000 units, about 10,000 units to about 1,000,000 units, about 50,000 units to about 100,000 units, about 50,000 units to about 500,000 units, about 50,000 units to about 1,000,000 units, about 100,000 units to about 500,000 units, about 100,000 units to about 1,000,000 units, or about 500,000 units to about 1,000,000 units. In some embodiments, the homogeneous population of extracellular vesicles expresses a number of units of the immune checkpoint moiety that is at least about 5 units, about 10 units, about 50 units, about 100 units, about 500 units, about 1,000 units, about 5,000 units, about 10,000 units, about 50,000 units, about 100,000 units, about 500,000 units, or about 1,000,000 units. In some embodiments, the homogeneous population of extracellular vesicles expresses a number of units of the immune checkpoint moiety that is at least at least about 5 units, about 10 units, about 50 units, about 100 units, about 500 units, about 1,000 units, about 5,000 units, about 10,000 units, about 50,000 units, about 100,000 units, or about 500,000 units. In some embodiments, the homogeneous population of extracellular vesicles expresses a number of units of the immune checkpoint moiety that is at least at most about 10 units, about 50 units, about 100 units, about 500 units, about 1,000 units, about 5,000 units, about 10,000 units, about 50,000 units, about 100,000 units, about 500,000 units, or about 1,000,000 units.

In some embodiments, the homogeneous population of extracellular vesicles expresses a number of units of the immune checkpoint moiety that is at most about 5 units to about 1,000,000 units. In some embodiments, the homogeneous population of extracellular vesicles expresses a number of units of the immune checkpoint moiety that is at most about 5 units to about 10 units, about 5 units to about 50 units, about 5 units to about 100 units, about 5 units to about 500 units, about 5 units to about 1,000 units, about 5 units to about 5,000 units, about 5 units to about 10,000 units, about 5 units to about 50,000 units, about 5 units to about 100,000 units, about 5 units to about 500,000 units, about 5 units to about 1,000,000 units, about 10 units to about 50 units, about 10 units to about 100 units, about 10 units to about 500 units, about 10 units to about 1,000 units, about 10 units to about 5,000 units, about 10 units to about 10,000 units, about 10 units to about 50,000 units, about 10 units to about 100,000 units, about 10 units to about 500,000 units, about 10 units to about 1,000,000 units, about 50 units to about 100 units, about 50 units to about 500 units, about 50 units to about 1,000 units, about 50 units to about 5,000 units, about 50 units to about 10,000 units, about 50 units to about 50,000 units, about 50 units to about 100,000 units, about 50 units to about 500,000 units, about 50 units to about 1,000,000 units, about 100 units to about 500 units, about 100 units to about 1,000 units, about 100 units to about 5,000 units, about 100 units to about 10,000 units, about 100 units to about 50,000 units, about 100 units to about 100,000 units, about 100 units to about 500,000 units, about 100 units to about 1,000,000 units, about 500 units to about 1,000 units, about 500 units to about 5,000 units, about 500 units to about 10,000 units, about 500 units to about 50,000 units, about 500 units to about 100,000 units, about 500 units to about 500,000 units, about 500 units to about 1,000,000 units, about 1,000 units to about 5,000 units, about 1,000 units to about 10,000 units, about 1,000 units to about 50,000 units, about 1,000 units to about 100,000 units, about 1,000 units to about 500,000 units, about 1,000 units to about 1,000,000 units, about 5,000 units to about 10,000 units, about 5,000 units to about 50,000 units, about 5,000 units to about 100,000 units, about 5,000 units to about 500,000 units, about 5,000 units to about 1,000,000 units, about 10,000 units to about 50,000 units, about 10,000 units to about 100,000 units, about 10,000 units to about 500,000 units, about 10,000 units to about 1,000,000 units, about 50,000 units to about 100,000 units, about 50,000 units to about 500,000 units, about 50,000 units to about 1,000,000 units, about 100,000 units to about 500,000 units, about 100,000 units to about 1,000,000 units, or about 500,000 units to about 1,000,000 units. In some embodiments, the homogeneous population of extracellular vesicles expresses a number of units of the immune checkpoint moiety that is at most about 5 units, about 10 units, about 50 units, about 100 units, about 500 units, about 1,000 units, about 5,000 units, about 10,000 units, about 50,000 units, about 100,000 units, about 500,000 units, or about 1,000,000 units. In some embodiments, the homogeneous population of extracellular vesicles expresses a number of units of the immune checkpoint moiety that is at most at least about 5 units, about 10 units, about 50 units, about 100 units, about 500 units, about 1,000 units, about 5,000 units, about 10,000 units, about 50,000 units, about 100,000 units, or about 500,000 units. In some embodiments, the homogeneous population of extracellular vesicles expresses a number of units of the immune checkpoint moiety that is at most at most about 10 units, about 50 units, about 100 units, about 500 units, about 1,000 units, about 5,000 units, about 10,000 units, about 50,000 units, about 100,000 units, about 500,000 units, or about 1,000,000 units.

In some embodiments, the homogeneous population of extracellular vesicles expresses a number of units of the immune checkpoint moiety that is between about 1,000 units to about 10,000 units. In some embodiments, the homogeneous population of extracellular vesicles expresses a number of units of the immune checkpoint moiety that is between about 1,000 units to about 1,500 units, about 1,000 units to about 2,000 units, about 1,000 units to about 2,500 units, about 1,000 units to about 3,000 units, about 1,000 units to about 4,000 units, about 1,000 units to about 5,000 units, about 1,000 units to about 6,000 units, about 1,000 units to about 7,000 units, about 1,000 units to about 8,000 units, about 1,000 units to about 9,000 units, about 1,000 units to about 10,000 units, about 1,500 units to about 2,000 units, about 1,500 units to about 2,500 units, about 1,500 units to about 3,000 units, about 1,500 units to about 4,000 units, about 1,500 units to about 5,000 units, about 1,500 units to about 6,000 units, about 1,500 units to about 7,000 units, about 1,500 units to about 8,000 units, about 1,500 units to about 9,000 units, about 1,500 units to about 10,000 units, about 2,000 units to about 2,500 units, about 2,000 units to about 3,000 units, about 2,000 units to about 4,000 units, about 2,000 units to about 5,000 units, about 2,000 units to about 6,000 units, about 2,000 units to about 7,000 units, about 2,000 units to about 8,000 units, about 2,000 units to about 9,000 units, about 2,000 units to about 10,000 units, about 2,500 units to about 3,000 units, about 2,500 units to about 4,000 units, about 2,500 units to about 5,000 units, about 2,500 units to about 6,000 units, about 2,500 units to about 7,000 units, about 2,500 units to about 8,000 units, about 2,500 units to about 9,000 units, about 2,500 units to about 10,000 units, about 3,000 units to about 4,000 units, about 3,000 units to about 5,000 units, about 3,000 units to about 6,000 units, about 3,000 units to about 7,000 units, about 3,000 units to about 8,000 units, about 3,000 units to about 9,000 units, about 3,000 units to about 10,000 units, about 4,000 units to about 5,000 units, about 4,000 units to about 6,000 units, about 4,000 units to about 7,000 units, about 4,000 units to about 8,000 units, about 4,000 units to about 9,000 units, about 4,000 units to about 10,000 units, about 5,000 units to about 6,000 units, about 5,000 units to about 7,000 units, about 5,000 units to about 8,000 units, about 5,000 units to about 9,000 units, about 5,000 units to about 10,000 units, about 6,000 units to about 7,000 units, about 6,000 units to about 8,000 units, about 6,000 units to about 9,000 units, about 6,000 units to about 10,000 units, about 7,000 units to about 8,000 units, about 7,000 units to about 9,000 units, about 7,000 units to about 10,000 units, about 8,000 units to about 9,000 units, about 8,000 units to about 10,000 units, or about 9,000 units to about 10,000 units. In some embodiments, the homogeneous population of extracellular vesicles expresses a number of units of the immune checkpoint moiety that is between about 1,000 units, about 1,500 units, about 2,000 units, about 2,500 units, about 3,000 units, about 4,000 units, about 5,000 units, about 6,000 units, about 7,000 units, about 8,000 units, about 9,000 units, or about 10,000 units. In some embodiments, the homogeneous population of extracellular vesicles expresses a number of units of the immune checkpoint moiety that is between at least about 1,000 units, about 1,500 units, about 2,000 units, about 2,500 units, about 3,000 units, about 4,000 units, about 5,000 units, about 6,000 units, about 7,000 units, about 8,000 units, or about 9,000 units. In some embodiments, the homogeneous population of extracellular vesicles expresses a number of units of the immune checkpoint moiety that is between at most about 1,500 units, about 2,000 units, about 2,500 units, about 3,000 units, about 4,000 units, about 5,000 units, about 6,000 units, about 7,000 units, about 8,000 units, about 9,000 units, or about 10,000 units.

Transmembrane Moiety

Discredited herein, in some embodiments, are compositions comprising extracellular vesicles comprising transmembrane moiety. In some embodiments, the transmembrane moiety comprises a full length protein or a variation thereof or a fragment thereof. In some embodiments, the transmembrane is selected from a group consisting of: 14-3-3 protein zeta/delta, 4-3-3 protein epsilon, 78 kDa glucose-regulated protein, acetylcholinesterase/AChE-S, AChE-E, actin, cytoplasmic 1 (ACTA), ADAM10, alkaline phosphatase, alpha-enolase, alpha-synuclein, aminopeptidase N, amyloid beta A4/APP, annexin 5A, annexin A2, AP-1, ATF3, ATP citrate lyase, ATPase, beta actin (ACTB), beta-amyloid 42, caveolin-1, CD10, CD11a, CD11b, CD11c, CD14, CD142, CD146, CD163, CD24, CD26/DPP4, CD29/ITGB1, CD3, CD37, CD41, CD42a, CD44, CD45, CD47, CD49, CD49d, CD53, CD63, CD64, CD69, CD73 CD81, CD82, CD9, CD90, claudin, claudin-1 cofilin-1, complement-binding proteins CD55 and CD59, cytosolic heat shock protein 90 alpha, cytosolic heat shock protein 90 beta, EBV LMP1, EBV LMP2A, EF-1alpha-1, EF2, EFGR EGFR VIII, emmprin/CD147, enolase 1 alpha (ENO1), EPCAM, ERBB2, tetraspanins (CD9, CD63 and CD81), fatty acid synthase, fetuin-A, flotillin-1, flotillin-2, fructose-bisphosphate aldolase A, glyceraldehyde-3-phosphate dehydrogenase (GAPDH), glycophorin A, GPC1, GPI-anchored 5'nucleotidase, GTPase, heat shock protein 8 (HSPA8), heat shock proteins (HSP70 and HSP90), heparan sulfate proteoglycans, heparinase, heterotrimeric G proteins, HIV Gag, HIV Nef, HLA-DRA, HLA-G, HSV gB, HTLV-1 Tax, huntingtin, ICAM1, integrins, lactadherin, LAMP1/2, LAMP2b, leucine-rich receptor kinase 2, L-lactate dehydrogenase A chain, lysosome-associated membrane glycoprotein 1, lysosome-associated membrane glycoprotein 2, MHC class I, MHC class II, MUC1, multidrug resistance-associated protein, muscle pyruvate kinase (PKM2), N-cadherin, NKCC2, PDCD6IP/Alix, PECAM1, phosphoglycerate kinase, placental prion proteins, prostate-specific antigen (PSA), pyruvate kinase (PKM), Rab-14, Rab-5a, Rab-5b, Rab-5c, Rab-7, Rap 1B, resistin, sonic hedgehog (SHH), surviving, syndecan-1, syndecan-4, syntenin-1, transferrin receptor (TFR2), TSG101, TSPAN8, tumor-associated glycoprotein tetraspanin-8, tyrosine 3 monooxygenase/tryptophan 5-monooxygenase activation protein, TYRP-2, vacuolar-sorting protein 35, or zeta polypeptide (YWHAZ). In some embodiments, the transmembrane moiety comprises lactadherin. In some embodiments, the transmembrane moiety comprises C1C2 domain of lactadherin. In some embodiments, the transmembrane moiety comprises LAMP2. In some embodiments, the transmembrane moiety comprises LAMP-like domain 1 of LAMP2. In some embodiments, the transmembrane moiety comprises LAMP2b. In some embodiments, the transmembrane moiety comprises a peptide that is at least 50%, 55%, 60%, 65%, 70%, 75%, 80%. 85%. 90%, 95%, or 99% identical to SEQ ID NO: 4 (Table 2). In some embodiments, the transmembrane moiety comprises a peptide that is 100% identical to SEQ ID NO: 4. In some embodiments, the transmembrane moiety comprises glycosylphosphatidylinositol (GPI) protein. In some embodiments, the transmembrane moiety comprises glycan portion of GPI. In some embodiments, the transmembrane moiety comprises lipid portion of GPI. In some cases, the transmembrane moiety comprises CD63. In some embodiments, the transmembrane moiety comprises a peptide is at least 50%, 55%, 60%, 65%, 70%, 75%, 80%. 85%. 90%, 95%, or 99% identical to SEQ ID NO: 5 (Table 2). In some embodiments, the transmembrane moiety comprises a peptide that is 100% identical to SEQ ID NO: 5. In some embodiments, the transmembrane moiety comprises a modified CD63. In some embodiments, the modified CD63 comprises at least one CD63 transmembrane domain. The transmembrane domain can be transmembrane domain 1 (TM1) of CD63, transmembrane domain 2 (TM2) of CD63, transmembrane domain 3 (TM3) of CD63, transmembrane domain 4 (TM4) of CD63, or any combination thereof. In some embodiments, the modified CD63 comprises one, two, three, four, five, six, seven, eight, nine, ten or more of transmembrane domains of CD63. In some embodiments, the modified CD63 comprises one transmembrane domain. In some embodiments, the modified CD63 comprises two transmembrane domains. In some embodiments, the modified CD63 comprises three transmembrane domains. In some embodiments, the modified CD63 comprises four transmembrane domains. In some embodiments, the modified CD63 comprises five transmembrane domains. In some embodiments, the modified CD63 comprises six transmembrane domains. In some embodiments, the modified CD63 comprises seven transmembrane domains. In some embodiments, the modified CD63 comprises eight transmembrane domains. In some embodiments, the modified CD63 comprises nine transmembrane domains. In some embodiments, the modified CD63 comprises ten transmembrane domains. In some embodiments, the modified CD63 can be a truncated CD63, where at least one transmembrane domain is removed. In some embodiments, the modified CD63 comprises both truncation of CD63 and additional of at least one transmembrane domain of CD63. For example, a modified CD63 can be truncated at N-terminus to remove TM1 and further comprises additional TM3 and TM4, resulting in a modified CD63 comprising, in order of transmembrane domains of CD63, TM2, TM3, TM4, TM3, and TM4.

TABLE 2

Peptide Sequences of Lamp2b and CD63

| SEQ ID NO | |
|---|---|
| | Lamp2b, Accession Number P13473-2 |
| 4 | MVCFRLFPVPGSGLVLVCLVLGAVRSYALELNLTDSENATCLYAKWQMNFTVRYETTN KTYKTVTISDHGTVTYNGSICGDDQNGPKIAVQFGPGFSWIANFTKAASTYSIDSVSF SYNTGDNTTFPDAEDKGILTVDELLAIRIPLNDLFRCNSLSTLEKNDVVQHYWDVLVQ AFVQNGTVSTNEFLCDKDKTSTVAPTIHTTVPSPTTTPTPKEKPEAGTYSVNNGNDTC LLATMGLQLNITQDKVASVININPNTTHSTGSCRSHTALLRLNSSTIKYLDFVFAVKN ENRFYLKEVNISMYLVNGSVFSIANNNLSYWDAPLGSSYMCNKEQTVSVSGAFQINTF DLRVQPFNVTQGKYSTAQDCSADDDNFLVPIAVGAALAGVLILVLLAYFIGLKHHHAG YEQF |
| | CD63, Accession Number A0A024RB05 |
| 5 | MAVEGGMKCVKFLLYVLLLAFCACAVGLIAVGVGAQLVLSQTIIQGATPGSLLPVVIIAV GVFLFLVAFVGCCGACKENYCLMITFAIFLSLIMLVEVAAAIAGYVFRDKVMSEFNNNFR QQMENYPKNNHTASILDRMQADFKCCGAANYTDWEKIPSMSKNRVPDSCCINVTVGCGIN FNEKAIHKEGCVEKIGGWLRKNVLVVAAAALGIAFVEVLGIVFACCLVKSIRSGYEVM |

In some embodiments, the modified CD63 comprises inserting or substituting the non-transmembrane domains (either cytoplasmic loop or extracellular loop) of the modified CD63. In some embodiments, the modified CD63 comprises a cytoplasmic loop inserted or substituted with the immune checkpoint moiety. In some embodiments, the modified CD63 comprises an extracellular loop inserted or substituted with the immune checkpoint moiety. For example, a polypeptide comprising the immune checkpoint moiety can be inserted into the extracellular loop of the modified CD63. Alternatively, polypeptide comprising the immune checkpoint moiety can substitute a fragment of the extracellular loop of the modified CD63. In some embodiments, the immune checkpoint moiety can be fused to a truncated version of the modified CD63. In some embodiments, the immune checkpoint moiety can be fused to the N-terminus of the modified CD63, where the modified CD63 is truncated at the N-terminus to remove at least one of the transmembrane domains and/or at least one of the non-transmembrane domains. In some embodiments, the immune checkpoint moiety can be fused to the N-terminus of the modified CD63, where the modified CD63 is truncated at the N-terminus to remove at least one of the transmembrane domains and/or at least one of the non-transmembrane domains.

In some embodiments, the immune checkpoint moiety can be fused to the transmembrane moiety such as CD63 via a linker. In some embodiments, the linker is a linker peptide. The linker peptides not only serves to connect the moieties, but in some cases also provides many other functions, such as maintaining cooperative inter-domain interactions or preserving biological activity (Gokhale R S, Khosla C. Role of linkers in communication between protein modules. Curr Opin Chem Biol. 2000; 4: 22-27; Ikebe M, Kambara T, Stafford W F, Sata M, Katayama E, Ikebe R. A hinge at the central helix of the regulatory light chain of myosin is critical for phosphorylation-dependent regulation of smooth muscle myosin motor activity. J Biol Chem. 1998; 273: 17702-17707; and Chen X Y, Zaro J, and Shen W C. Fusion protein linkers: property, design and functionality. Adv Drug Deliv Rev 2014; 65, 1357-1369 are incorporated herein). The linker peptides can be grouped into small, medium, and large linkers with average length of less than or up to 4.5±0.7, 9.1±2.4, and 21.0±7.6 residues or greater, respectively, although examples anywhere within the set defined by these three ranges are also contemplated. In some embodiments, the linker peptide comprises 5 to 200 amino acids. In other embodiments, the linker peptide comprises 5 to 25 amino acids. In some embodiments, the linker peptide is a cleavable (e.g., a linker peptide comprising a peptide sequence that can be recognized and cleaved by Tev protease).

SEQ ID NOS: 6-17 illustrate various arrangements of the immune checkpoint moiety PD-L1 fusing to the transmembrane moiety CD63 (Table 3).

TABLE 3

Peptide Sequence of Fusion of Immune Checkpoint Moiety and Transmembrane Moiety

| SEQ ID NO | Immune Checkpoint Moiety and Transmembrane Moiety Fusion Peptide | Comment |
|---|---|---|
| 6 | MAVEGGMKCVKFLLYVLLLAFCACAVGLIAVGVGAQLVLSQTIIQGATPGSLLPVVIIAVG VFLFLVAFVGCCGACKENYCLMITFAIFLSLIMLVEVAAAIAGYVFRDKVMSEGGGGS[X] | X is an extracellular domain of an Immune Checkpoint Inhibitor |
| 7 | MAVEGGMKCVKFLLYVLLLAFCACAVGLIAVGVGAQLVLSQTIIQGATPGSLLPVVIIAVGV FLFLVAFVGCCGACKENYCLMITFAIFLSLIMLVEVAAAIAGYVFRDKVMSEGGGGSFTVTV | |

TABLE 3-continued

Peptide Sequence of Fusion of Immune Checkpoint Moiety and Transmembrane Moiety

| SEQ ID NO | Immune Checkpoint Moiety and Transmembrane Moiety Fusion Peptide | Comment |
|---|---|---|
|  | PKDLYVVEYGSNMTIECKFPVEKQLDLAALIVYWEMEDKNIIQFVHGEEDLKVQHSSYRQRA RLLKDQLSLGNAALQITDVKLQDAGVYRCMISYGGADYKRITVKVNAPYNKINQRILVVDPV TSEHELTCQAEGYPKAEVIWTSSDHQVLSGKTTTTNSKREEKLFNVTSTLRINTTTNEIFYC TFRRLDPEENHTAELVIPELPLAHPPNER |  |
| 8 | MAVEGGMKCVKFLLYVLLLAFCACAVGLIAVGVGAQLVLSQTIIQGATPGSLLPVVIIAVGV FLFLVAFVGCCGACKENYCLMITFAIFLSLIMLVEVAAAIAGYVFRDKVMSEGGGGSGGGGS GGGGS[X] | X is an extracellular domain of an Immune Checkpoint Inhibitor |
| 9 | MAVEGGMKCVKFLLYVLLLAFCACAVGLIAVGVGAQLVLSQTIIQGATPGSLLPVVIIAVGV FLFLVAFVGCCGACKENYCLMITFAIFLSLIMLVEVTWAIAGYVFRDKVMSEGGGGSGGGGS GGGGSFTVTVPKDLYVVEYGSNMTIECKFPVEKQLDLAALIVYWEMEDKNIIQFVHGEEDLK VQHSSYRQRARLLKDQLSLGNAALQITDVKLQDAGVYRCMISYGGADYKRITVKVNAPYNKI NQRILVVDPVTSEHELTCQAEGYPKAEVIWTSSDHQVLSGKTTTTNSKREEKLFNVTSTLRI NTTTNEIFYCTFRRLDPEENHTAELVIPELPLAHPPNER |  |
| 10 | MAVEGGMKCVKFLLYVLLLAFCACAVGLIAVGVGAQLVLSQTIIQGATPGSLLPVVIIAVGV FLFLVAFVGCCGACKENYCLMITFAIFLSLIMLVEVAAAIAGYVFRDKVMSEVMSEFNNNFR QQGGGGSX | wherein X is an extracellular domain of an Immune Checkpoint Inhibitor |
| 11 | MAVEGGMKCVKFLLYVLLLAFCACAVGLIAVGVGAQLVLSQTIIQGATPGSLLPVVIIAVGV FLFLVAFVGCCGACKENYCLMITFAIFLSLIMLVEVTWAIAGYVFRDKVMSEVMSEFNNNFR QQGGGGSFTVTVPKDLYVVEYGSNMTIECKFPVEKQLDLAALIVYWEMEDKNIIQFVHGEED LKVQHSSYRQRARLLKDQLSLGNAALQITDVKLQDAGVYRCMISYGGADYKRITVKVNAPYN KINQRILVVDPVTSEHELTCQAEGYPKAEVIWTSSDHQVLSGKTTTTNSKREEKLFNVTSTL RINTTTNEIFYCTFRRLDPEENHTAELVIPELPLAHPPNER |  |
| 12 | MAVEGGMKCVKFLLYVLLLAFCACAVGLIAVGVGAQLVLSQTIIQGATPGSLLPVVIIAVGV FLFLVAFVGCCGACKENYCLMITFAIFLSLIMLVEVAAAIAGYVFRDKVMSEVMSEFNNNFR QQGGGGSGGGGSGGGGS[X] | X is an extracellular domain of an Immune Checkpoint Inhibitor |
| 13 | MAVEGGMKCVKFLLYVLLLAFCACAVGLIAVGVGAQLVLSQTIIQGATPGSLLPVVIIAVGV FLFLVAFVGCCGACKENYCLMITFAIFLSLIMLVEVTWAIAGYVFRDKVMSEVMSEFNNNFR QQGGGGSGGGGSGGGGSFTVTVPKDLYVVEYGSNMTIECKFPVEKQLDLAALIVYWEMEDKN IIQFVHGEEDLKVQHSSYRQRARLLKDQLSLGNAALQITDVKLQDAGVYRCMISYGGADYKR ITVKVNAPYNKINQRILVVDPVTSEHELTCQAEGYPKAEVIWTSSDHQVLSGKTTTTNSKRE EKLFNVTSTLRINTTTNEIFYCTFRRLDPEENHTAELVIPELPLAHPPNER |  |
| 14 | MAVEGGMKCVKFLLYVLLLAFCACAVGLIAVGVGAQLVLSQTIIQGATPGSLLPVVIIAVGV FLFLVAFVGCCGACKENYCLMITFAIFLSLIMLVEVAAAIAGYVFRDKVMSEVMSEFNNNFR QQMENYPKNNHTGGGGSX | X is an extracellular domain of an Immune Checkpoint Inhibitor |
| 15 | MAVEGGMKCVKFLLYVLLLAFCACAVGLIAVGVGAQLVLSQTIIQGATPGSLLPVVIIAVGV FLFLVAFVGCCGACKENYCLMITFAIFLSLIMLVEVTWAIAGYVFRDKVMSEVMSEFNNNFR QQMENYPKNNHTGGGGSFTVTVPKDLYVVEYGSNMTIECKFPVEKQLDLAALIVYWEMEDKN IIQFVHGEEDLKVQHSSYRQRARLLKDQLSLGNAALQITDVKLQDAGVYRCMISYGGADYKR ITVKVNAPYNKINQRILVVDPVTSEHELTCQAEGYPKAEVIWTSSDHQVLSGKTTTTNSKRE EKLFNVTSTLRINTTTNEIFYCTFRRLDPEENHTAELVIPELPLAHPPNER |  |

TABLE 3-continued

Peptide Sequence of Fusion of Immune Checkpoint Moiety and Transmembrane Moiety

| SEQ ID NO | Immune Checkpoint Moiety and Transmembrane Moiety Fusion Peptide | Comment |
|---|---|---|
| 16 | MAVEGGMKCVKFLLYVLLLAFCACAVGLIAVGVGAQLVLSQTIIQGATPGSLLPVVIIAVGV FLFLVAFVGCCGACKENYCLMITFAIFLSLIMLVEVAAAIAGYVFRDKVMSEVMSEFNNNFR QQMENYPKNNHTGGGGSGGGGSGGGGS[X] | X is an extracellular domain of an Immune Checkpoint Inhibitor X is an |
| 17 | MAVEGGMKCVKFLLYVLLLAFCACAVGLIAVGVGAQLVLSQTIIQGATPGSLLPVVIIAVGV FLFLVAFVGCCGACKENYCLMITFAIFLSLIMLVEVAAAIAGYVFRDKVMSEVMSEFNNNFR QQMENYPKNNHTGGGGSGGGGSGGGGSFTVTVPKDLYVVEYGSNMTIECKFPVEKQLDLAAL IVYWEMEDKNIIQFVHGEEDLKVQHSSYRQRARLLKDQLSLGNAALQITDVKLQDAGVYRCM ISYGGADYKRITVKVNAPYNKINQRILVVDPVTSEHELTCQAEGYPKAEVIWTSSDHQVLSG KTTTTNSKREEKLFNVTSTLRINTTTNEIFYCTFRRLDPEENHTAELVIPELPLAHPPNER | 0 |

In some embodiments, the extracellular vesicle described herein expresses a polypeptide that is at least 50%, 55%, 60%, 65%, 70%, 75%, 80%. 85%. 90%, 95%, or 99% identical to SEQ ID NO: 6. In some embodiments, the extracellular vesicle described herein expresses a polypeptide that is 100% identical to SEQ ID NO: 6. In some embodiments, the expressed polypeptide corresponding to SEQ ID NO: 6 is partially embedded in the membrane of the extracellular vesicle and is partially expressed on the surface of the extracellular vesicle.

7 In some embodiments, the extracellular vesicle described herein expresses a polypeptide that is at least 50%, 55%, 60%, 65%, 70%, 75%, 80%. 85%. 90%, 95%, or 99% identical to SEQ ID NO: 7. In some embodiments, the extracellular vesicle described herein expresses a polypeptide that is 100% identical to SEQ ID NO: 7. In some embodiments, the expressed polypeptide corresponding to SEQ ID NO: 7 is partially embedded in the membrane of the extracellular vesicle and is partially expressed on the surface of the extracellular vesicle.

In some embodiments, the extracellular vesicle described herein expresses a polypeptide that is at least 50%, 55%, 60%, 65%, 70%, 75%, 80%. 85%. 90%, 95%, or 99% identical to SEQ ID NO: 8. In some embodiments, the extracellular vesicle described herein expresses a polypeptide that is 100% identical to SEQ ID NO: 8. In some embodiments, the expressed polypeptide corresponding to SEQ ID NO: 8 is partially embedded in the membrane of the extracellular vesicle and is partially expressed on the surface of the extracellular vesicle.

In some embodiments, the extracellular vesicle described herein expresses a polypeptide that is at least 50%, 55%, 60%, 65%, 70%, 75%, 80%. 85%. 90%, 95%, or 99% identical to SEQ ID NO: 9. In some embodiments, the extracellular vesicle described herein expresses a polypeptide that is 100% identical to SEQ ID NO: 9. In some embodiments, the expressed polypeptide corresponding to SEQ ID NO: 9 is partially embedded in the membrane of the extracellular vesicle and is partially expressed on the surface of the extracellular vesicle.

In some embodiments, the extracellular vesicle described herein expresses a polypeptide that is at least 50%, 55%, 60%, 65%, 70%, 75%, 80%. 85%. 90%, 95%, or 99% identical to SEQ ID NO: 10. In some embodiments, the extracellular vesicle described herein expresses a polypeptide that is 100% identical to SEQ ID NO: 10. In some embodiments, the expressed polypeptide corresponding to SEQ ID NO: 10 is partially embedded in the membrane of the extracellular vesicle and is partially expressed on the surface of the extracellular vesicle.

In some embodiments, the extracellular vesicle described herein expresses a polypeptide that is at least 50%, 55%, 60%, 65%, 70%, 75%, 80%. 85%. 90%, 95%, or 99% identical to SEQ ID NO: 11. In some embodiments, the extracellular vesicle described herein expresses a polypeptide that is 100% identical to SEQ ID NO: 11. In some embodiments, the expressed polypeptide corresponding to SEQ ID NO: 11 is partially embedded in the membrane of the extracellular vesicle and is partially expressed on the surface of the extracellular vesicle.

In some embodiments, the extracellular vesicle described herein expresses a polypeptide that is at least 50%, 55%, 60%, 65%, 70%, 75%, 80%. 85%. 90%, 95%, or 99% identical to SEQ ID NO: 12. In some embodiments, the extracellular vesicle described herein expresses a polypeptide that is 100% identical to SEQ ID NO: 12. In some embodiments, the expressed polypeptide corresponding to SEQ ID NO: 12 is partially embedded in the membrane of the extracellular vesicle and is partially expressed on the surface of the extracellular vesicle.

In some embodiments, the extracellular vesicle described herein expresses a polypeptide that is at least 50%, 55%, 60%, 65%, 70%, 75%, 80%. 85%. 90%, 95%, or 99% identical to SEQ ID NO: 13. In some embodiments, the extracellular vesicle described herein expresses a polypeptide that is 100% identical to SEQ ID NO: 13. In some embodiments, the expressed polypeptide corresponding to SEQ ID NO: 13 is partially embedded in the membrane of the extracellular vesicle and is partially expressed on the surface of the extracellular vesicle.

In some embodiments, the extracellular vesicle described herein expresses a polypeptide that is at least 50%, 55%, 60%, 65%, 70%, 75%, 80%. 85%. 90%, 95%, or 99% identical to SEQ ID NO: 14. In some embodiments, the extracellular vesicle described herein expresses a polypeptide that is 100% identical to SEQ ID NO: 14. In some embodiments, the expressed polypeptide corresponding to SEQ ID NO: 14 is partially embedded in the membrane of the extracellular vesicle and is partially expressed on the surface of the extracellular vesicle.

In some embodiments, the extracellular vesicle described herein expresses a polypeptide that is at least 50%, 55%, 60%, 65%, 70%, 75%, 80%. 85%. 90%, 95%, or 99% identical to SEQ ID NO: 15. In some embodiments, the extracellular vesicle described herein expresses a polypeptide that is 100% identical to SEQ ID NO: 15. In some embodiments, the expressed polypeptide corresponding to SEQ ID NO: 15 is partially embedded in the membrane of the extracellular vesicle and is partially expressed on the surface of the extracellular vesicle.

In some embodiments, the extracellular vesicle described herein expresses a polypeptide that is at least 50%, 55%, 60%, 65%, 70%, 75%, 80%. 85%. 90%, 95%, or 99% identical to SEQ ID NO: 16. In some embodiments, the extracellular vesicle described herein expresses a polypeptide that is 100% identical to SEQ ID NO: 16. In some embodiments, the expressed polypeptide corresponding to SEQ ID NO: 16 is partially embedded in the membrane of the extracellular vesicle and is partially expressed on the surface of the extracellular vesicle.

In some embodiments, the extracellular vesicle described herein expresses a polypeptide that is at least 50%, 55%, 60%, 65%, 70%, 75%, 80%. 85%. 90%, 95%, or 99% identical to SEQ ID NO: 17. In some embodiments, the extracellular vesicle described herein expresses a polypeptide that is 100% identical to SEQ ID NO: 17. In some embodiments, the expressed polypeptide corresponding to SEQ ID NO: 17 is partially embedded in the membrane of the extracellular vesicle and is partially expressed on the surface of the extracellular vesicle.

In some embodiments, the transmembrane moiety can be complexed with the immune checkpoint moiety described herein. In some embodiments, the transmembrane moiety can be non-covalently complex with the immune checkpoint moiety described herein. In some embodiments, the transmembrane moiety can be covalently complexed with the immune checkpoint moiety described herein. In some embodiments, the transmembrane moiety can be fused to the immune checkpoint moiety described herein at the N-terminus of the transmembrane moiety. In some embodiments, the transmembrane moiety can be fused to the immune checkpoint moiety described herein at the C-terminus of the transmembrane moiety.

In some embodiments, the immune checkpoint moiety comprises therapeutic properties for treating a disease or a disorder. In some embodiments, the immune checkpoint moiety comprises therapeutic properties for treating an autoimmune disease described herein. In some embodiments, the immune checkpoint moiety targets and modulates activities of immune cells. In some embodiments, the immune cells can be T cell, including Cytotoxic T cell, Natural Killer T cell, Regulatory T cell, and T helper cells.

Targeting Moiety

Described herein, in some embodiments, are extracellular vesicles comprising targeting moiety. In some embodiments, the targeting moiety can be expressed on the surface of the extracellular vesicle. In some embodiments, the targeting moiety can be secreted by the extracellular vesicle. The extracellular vehicles comprising the targeting moiety localizes at the target cell or target environment is at least 2 fold, 5 fold, 10 fold, 50 fold, 100 fold, 200 fold, 500 fold, 1,000 fold, 5,000 fold, or 10,000 fold higher compared to localization of an extracellular vesicle lacking the targeting moiety. In some embodiments, the targeting moiety comprises EBV glycoprotein 350, which targets CD19+ B cells. In some embodiments, the targeting moiety comprises Lamp2b, which targets acetylcholine receptors on neurons. In some embodiments, the targeting moiety comprises C1C2 domain of lactadherin, which target immune cells or blood cells, In some embodiments, the targeting moiety comprises PDGFR, which targets EGFR or cells expressing EGFR. In some embodiments, the targeting moiety comprises GPI-anchored membrane proteins.

In some embodiments, the targeting moiety can target a cell surface protein or a protein secreted by the target cell. Non-limiting examples of the cell surface or secreted proteins include any one of the chemokines described herein.

Pharmaceutical Compositions

Described herein are pharmaceutical compositions comprising the compositions described herein. In some embodiments, the pharmaceutical composition comprises both the composition comprising the extracellular vesicle and the cells that secret the extracellular vesicles. A pharmaceutical composition, as used herein, refers to a mixture of a therapeutic agent comprising extracellular vesicle, with other chemical components (i.e., pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. Optionally, the compositions include two or more therapeutic agent (e.g., one or more therapeutic agents and one or more additional agents) as discussed herein. In practicing the methods of treatment or use provided herein, therapeutically effective amounts of therapeutic agents described herein are administered in a pharmaceutical composition to a mammal having a disease, disorder, or condition to be treated, e.g., an autoimmune disease. In some embodiments, the mammal is a human. A therapeutically effective amount can vary widely depending on the severity of the disease, the age and relative health of the subject, the potency of the therapeutic agent used and other factors. The therapeutic agents can be used singly or in combination with one or more therapeutic agents as components of mixtures.

The pharmaceutical formulations described herein are administered to a subject by appropriate administration routes, including but not limited to, intravenous, intraarterial, oral, parenteral, buccal, topical, transdermal, rectal, intramuscular, subcutaneous, intraosseous, transmucosal, inhalation, or intraperitoneal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a therapeutic agent are manufactured in a conventional manner, such as, by way of example only, by means of conventional mixing, dissolving, granulating, dragee-making, levigating, emulsifying, encapsulating, entrapping or compression processes.

The pharmaceutical compositions may include at least a therapeutic agent as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity. In some embodiments, therapeutic agents exist in unsolvated form or in solvated forms with pharmaceutically acceptable solvents such as water, ethanol, and the like. The solvated forms of the therapeutic agents are also considered to be disclosed herein.

In some embodiments, a therapeutic agent exists as a tautomer. All tautomers are included within the scope of the agents presented herein. As such, it is to be understood that a therapeutic agent or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound.

In some embodiments, a therapeutic agent exists as an enantiomer, diastereomer, or other steroisomeric form. The agents disclosed herein include all enantiomeric, diastereomeric, and epimeric forms as well as mixtures thereof.

In some embodiments, therapeutic agents described herein may be prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a therapeutic agent described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the therapeutic agent. In certain embodiments, a prodrug is enzymatically metabolized by one or more steps or processes to the biologically, pharmaceutically or therapeutically active form of the therapeutic agent.

Prodrug forms of the therapeutic agents, wherein the prodrug is metabolized in vivo to produce an agent as set forth herein are included within the scope of the claims. Prodrug forms of the herein described therapeutic agents, wherein the prodrug is metabolized in vivo to produce an agent as set forth herein are included within the scope of the claims. In some cases, some of the therapeutic agents described herein may be a prodrug for another derivative or active compound. In some embodiments described herein, hydrazones are metabolized in vivo to produce a therapeutic agent.

In certain embodiments, compositions provided herein include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

The pharmaceutical compositions described herein are formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In one aspect, a therapeutic agent as discussed herein, e.g., therapeutic agent is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. In some embodiments, formulations suitable for subcutaneous injection also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. In some cases it is desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections or drips or infusions, a therapeutic agent described herein is formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

For administration by inhalation, a therapeutic agent is formulated for use as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the therapeutic agent described herein and a suitable powder base such as lactose or starch.

Representative intranasal formulations are described in, for example, U.S. Pat. Nos. 4,476,116, 5,116,817 and 6,391,452. Formulations that include a therapeutic agent are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

Pharmaceutical preparations for oral use are obtained by mixing one or more solid excipient with one or more of the therapeutic agents described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active therapeutic agent doses.

In some embodiments, pharmaceutical formulations of a therapeutic agent are in the form of a capsules, including push fit capsules made of gelatin, as well as soft, sealed capsules made of gelatin and a plasticizer, such as glycerol or sorbitol. The push fit capsules contain the active ingredients in admixture with filler such as lactose, binders such as starches, and/or lubricants such as talc or magnesium stearate and, optionally, stabilizers. In soft capsules, the active therapeutic agent is dissolved or suspended in suitable liquids, such as fatty oils, liquid paraffin, or liquid polyethylene glycols. In some embodiments, stabilizers are added. A capsule may be prepared, for example, by placing the bulk blend of the formulation of the therapeutic agent inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

All formulations for oral administration are in dosages suitable for such administration. In one aspect, solid oral dosage forms are prepared by mixing a therapeutic agent with one or more of the following: antioxidants, flavoring agents, and carrier materials such as binders, suspending agents, disintegration agents, filling agents, surfactants, solubilizers, stabilizers, lubricants, wetting agents, and diluents. In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder. Compressed tablets are solid dosage forms prepared by compacting the bulk blend of the formulations described above. In various embodiments, tablets will include one or more flavoring agents. In other embodiments, the tablets will include a film surrounding the final compressed tablet. In some embodiments, the film coating can provide a delayed release of a therapeutic agent from the formulation. In other embodiments, the film coating aids in patient compliance (e.g., Opadry® coatings or sugar coating). Film coatings including Opadry® typically range from about 1% to about 3% of the tablet weight. In some embodiments, solid dosage forms, e.g., tablets, effervescent tablets, and capsules, are prepared by mixing particles of a therapeutic agent with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents. Exemplary useful microencapsulation materials include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG,HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

Liquid formulation dosage forms for oral administration are optionally aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to therapeutic agent the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further includes a crystal-forming inhibitor.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401, 6,667,048, and 6,960,563.

Buccal formulations that include a therapeutic agent are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

For intravenous injections, a therapeutic agent is optionally formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or nonaqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, a pharmaceutical composition described herein is in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an agent that modulates the activity of a carotid body in water soluble form. Additionally, suspensions of an agent that modulates the activity of a carotid body are optionally prepared as appropriate, e.g., oily injection suspensions.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

Suitable disintegrants for use in the solid dosage forms described herein include, but are not limited to, natural starch such as corn starch or potato starch, a pregelatinized starch, or sodium starch glycolate, a cellulose such as methylcrystalline cellulose, methylcellulose, microcrystalline cellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a gum such as agar, guar, locust bean, Karaya, pectin, or tragacanth, sodium starch glycolate, bentonite, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose, hydroxypropylmethylcellulose, hydroxypropylmethylcellulose acetate stearate, hydroxyethylcellulose, hydroxypropylcellulose, ethylcellulose, and microcrystalline cellulose, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose, glucose, dextrose, molasses, mannitol, sorbitol, xylitol, lactose, a natural or synthetic gum such as acacia, tragacanth, ghatti gum, mucilage of isapol husks, starch, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Binder levels of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 100), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms of the pharmaceutical compositions described herein. The amounts of such additives can be readily determined by one skilled in the art, according to the particular properties desired.

In various embodiments, the particles of a therapeutic agents and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In other embodiments, a powder including a therapeutic agent is formulated to include one or more pharmaceutical excipients and flavors. Such a powder is prepared, for example, by mixing the therapeutic agent and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared. Effervescent salts have been used to disperse medicines in water for oral administration.

In some embodiments, the pharmaceutical dosage forms are formulated to provide a controlled release of a therapeutic agent. Controlled release refers to the release of the therapeutic agent from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules, which include a therapeutic agent that are coated or uncoated.

Any coatings should be applied to a sufficient thickness such that the entire coating does not dissolve in the gastrointestinal fluids at pH below about 5, but does dissolve at pH about 5 and above. Coatings are typically selected from any of the following: Shellac—this coating dissolves in media of pH>7; Acrylic polymers—examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine; Poly Vinyl Acetate Phthalate (PVAP)—PVAP dissolves in pH>5, and it is much less permeable to water vapor and gastric fluids. Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e., multiparticulate) each containing the formulation described herein. The first group of particles provides a substantially immediate dose of a therapeutic agent upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or known in the art.

In some embodiments, pharmaceutical formulations are provided that include particles of a therapeutic agent and at least one dispersing agent or suspending agent for oral administration to a subject. The formulations may be a powder and/or granules for suspension, and upon admixture with water, a substantially uniform suspension is obtained.

In some embodiments, particles formulated for controlled release are incorporated in a gel or a patch or a wound dressing.

In one aspect, liquid formulation dosage forms for oral administration and/or for topical administration as a wash are in the form of aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of a therapeutic agent, the liquid dosage forms include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

In some embodiments, the liquid formulations also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In one embodiment, the aqueous suspensions and dispersions described herein remain in a homogenous state, as defined in The USP Pharmacists' Pharmacopeia (2005 edition, chapter 905), for at least 4 hours. In one embodiment, an aqueous suspension is re-suspended into a homogenous suspension by physical agitation lasting less than 1 minute. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch, or sodium starch glycolate; a cellulose such as methylcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein include, for example, hydrophilic polymers, electrolytes, Tween® 60 or 80, PEG, polyvinylpyrrolidone, and the carbohydrate-based dispersing agents such as, for example, hydroxypropylcellulose and hydroxypropyl cellulose ethers, hydroxypropyl methylcellulose and hydroxypropyl methylcellulose ethers, carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer, 4-(1,1,3,3-tetramethylbutyl)-phenol polymer with ethylene oxide and formaldehyde (also known as tyloxapol), poloxamers; and poloxamines. In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers; hydroxypropyl methylcellulose and hydroxypropyl methylcellulose ethers; carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers; or poloxamines.

Wetting agents suitable for the aqueous suspensions and dispersions described herein include, but are not limited to, cetyl alcohol, glycerol monostearate, polyoxyethylene sorbitan fatty acid esters (e.g., the commercially available Tweens® such as e.g., Tween 20® and Tween 80®, and polyethylene glycols, oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like.

Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, aspartame, chocolate, cinnamon, citrus, cocoa, cyclamate, dextrose, fructose, ginger, glycyrrhetinate, glycyrrhiza (licorice) syrup, monoammonium glyrrhizinate (MagnaSweet®), malitol, mannitol, menthol, neohesperidine DC, neotame, Prosweet® Powder, saccharin, sorbitol, stevia, sucralose, sucrose, sodium saccharin, saccharin, aspartame, acesulfame potassium, mannitol, sucralose, tagatose, thaumatin, vanilla, xylitol, or any combination thereof.

In some embodiments, a therapeutic agent is prepared as transdermal dosage form. In some embodiments, the transdermal formulations described herein include at least three components: (1) a therapeutic agent; (2) a penetration enhancer; and (3) an optional aqueous adjuvant. In some embodiments the transdermal formulations include additional components such as, but not limited to, gelling agents, creams and ointment bases, and the like. In some embodiments, the transdermal formulation is presented as a patch or a wound dressing. In some embodiments, the transdermal formulation further include a woven or non-woven backing material to enhance absorption and prevent the removal of the transdermal formulation from the skin. In other embodiments, the transdermal formulations described herein can maintain a saturated or supersaturated state to promote diffusion into the skin.

In one aspect, formulations suitable for transdermal administration of a therapeutic agent described herein employ transdermal delivery devices and transdermal delivery patches and can be lipophilic emulsions or buffered, aqueous solutions, dissolved and/or dispersed in a polymer or an adhesive. In one aspect, such patches are constructed for continuous, pulsatile, or on demand delivery of pharmaceutical agents. Still further, transdermal delivery of the therapeutic agents described herein can be accomplished by means of iontophoretic patches and the like. In one aspect, transdermal patches provide controlled delivery of a therapeutic agent. In one aspect, transdermal devices are in the form of a bandage comprising a backing member, a reservoir containing the therapeutic agent optionally with carriers, optionally a rate controlling barrier to deliver the therapeutic agent to the skin of the host at a controlled and predetermined rate over a prolonged period of time, and means to secure the device to the skin.

In further embodiments, topical formulations include gel formulations (e.g., gel patches which adhere to the skin). In some of such embodiments, a gel composition includes any polymer that forms a gel upon contact with the body (e.g., gel formulations comprising hyaluronic acid, pluronic polymers, poly(lactic-co-glycolic acid (PLGA)-based polymers or the like). In some forms of the compositions, the formulation comprises a low-melting wax such as, but not limited to, a mixture of fatty acid glycerides, optionally in combination with cocoa butter which is first melted. Optionally, the formulations further comprise a moisturizing agent.

In certain embodiments, delivery systems for pharmaceutical therapeutic agents may be employed, such as, for example, liposomes and emulsions. In certain embodiments, compositions provided herein can also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, a therapeutic agent described herein may be administered topically and can be formulated into a variety of topically administrable compositions, such as solutions, suspensions, lotions, gels, pastes, medicated sticks, balms, creams or ointments. Such pharmaceutical therapeutic agents can contain solubilizers, stabilizers, tonicity enhancing agents, buffers and preservatives.

An aerosol formulation for nasal administration is generally an aqueous solution designed to be administered to the nasal passages in drops or sprays. Nasal solutions can be similar to nasal secretions in that they are generally isotonic and slightly buffered to maintain a pH of about 5.5 to about 6.5, although pH values outside of this range can additionally be used. Antimicrobial agents or preservatives can also be included in the formulation.

An aerosol formulation for inhalations and inhalants can be designed so that the agent or combination of agents is carried into the respiratory tree of the subject when administered by the nasal or oral respiratory route. Inhalation solutions can be administered, for example, by a nebulizer. Inhalations or insufflations, comprising finely powdered or liquid drugs, can be delivered to the respiratory system as a pharmaceutical aerosol of a solution or suspension of the agent or combination of agents in a propellant, e.g., to aid in disbursement. Propellants can be liquefied gases, including halocarbons, for example, fluorocarbons such as fluorinated chlorinated hydrocarbons, hydrochlorofluorocarbons, and hydrochlorocarbons, as well as hydrocarbons and hydrocarbon ethers.

Halocarbon propellants can include fluorocarbon propellants in which all hydrogens are replaced with fluorine, chlorofluorocarbon propellants in which all hydrogens are replaced with chlorine and at least one fluorine, hydrogen-containing fluorocarbon propellants, and hydrogen-containing chlorofluorocarbon propellants. Hydrocarbon propellants useful include, for example, propane, isobutane, n-butane, pentane, isopentane and neopentane. A blend of hydrocarbons can also be used as a propellant. Ether propellants include, for example, dimethyl ether as well as the ethers. An aerosol formulation can also comprise more than one propellant. For example, the aerosol formulation can comprise more than one propellant from the same class, such as two or more fluorocarbons; or more than one, more than two, more than three propellants from different classes, such as a fluorohydrocarbon and a hydrocarbon. Pharmaceutical compositions of the present disclosure can also be dispensed with a compressed gas, e.g., an inert gas such as carbon dioxide, nitrous oxide or nitrogen.

Aerosol formulations can also include other components, for example, ethanol, isopropanol, propylene glycol, as well as surfactants or other components such as oils and detergents. These components can serve to stabilize the formulation and/or lubricate valve components.

The aerosol formulation can be packaged under pressure and can be formulated as an aerosol using solutions, suspensions, emulsions, powders and semisolid preparations. For example, a solution aerosol formulation can comprise a solution of an agent such as a transporter, carrier, or ion channel inhibitor in (substantially) pure propellant or as a mixture of propellant and solvent. The solvent can be used to dissolve the agent and/or retard the evaporation of the propellant. Solvents can include, for example, water, ethanol and glycols. Any combination of suitable solvents can be use, optionally combined with preservatives, antioxidants, and/or other aerosol components.

An aerosol formulation can be a dispersion or suspension. A suspension aerosol formulation can comprise a suspension of an agent or combination of agents, e.g., a transporter, carrier, or ion channel inhibitor, and a dispersing agent. Dispersing agents can include, for example, sorbitan trioleate, oleyl alcohol, oleic acid, lecithin and corn oil. A suspension aerosol formulation can also include lubricants, preservatives, antioxidant, and/or other aerosol components.

An aerosol formulation can similarly be formulated as an emulsion. An emulsion aerosol formulation can include, for example, an alcohol such as ethanol, a surfactant, water and a propellant, as well as an agent or combination of agents, e.g., a transporter, carrier, or ion channel. The surfactant used can be nonionic, anionic or cationic. One example of an emulsion aerosol formulation comprises, for example, ethanol, surfactant, water and propellant. Another example of an emulsion aerosol formulation comprises, for example, vegetable oil, glyceryl monostearate and propane.

Kits

Disclosed herein, in some embodiments, are kits for using the compositions described herein. In some embodiments, the kits disclosed herein may be used to treat a disease or disorder in a subject; or select a subject for treatment and/or monitor a treatment disclosed herein. In some embodiments, the kit comprises the compositions described herein, which can be used to perform the methods described herein. Kits comprise an assemblage of materials or components, including at least one of the compositions. Thus, in some embodiments the kit contains a composition including of the pharmaceutical composition, for the treatment of an autoimmune disease.

In some instances, the kits described herein comprise components for selecting for the homogenous population of extracellular vesicles. In some embodiments, the kit comprises the components for assaying the number of units of the immune checkpoint moiety expressed on the surface of the extracellular vesicle. In some embodiments, the kit comprises components for performing assays such as enzyme-linked immunosorbent assay (ELISA), single-molecular array (Simoa), PCR, and qPCR. The exact nature of the components configured in the kit depends on its intended purpose. For example, some embodiments are configured for the purpose of treating a disease or condition disclosed herein (e.g., autoimmune disease) in a subject. In some embodiments, the kit is configured particularly for the purpose of treating mammalian subjects. In some embodiments, the kit is configured particularly for the purpose of treating human subjects.

Instructions for use may be included in the kit. Optionally, the kit also contains other useful components, such as, diluents, buffers, pharmaceutically acceptable carriers, syringes, catheters, applicators, pipetting or measuring tools, bandaging materials or other useful paraphernalia. The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as compositions and the like. The packaging material is constructed by well-known methods, preferably to provide a sterile, contaminant-free environment. The packaging materials employed in the kit are those customarily utilized in gene expression assays and in the administration of treatments. As used herein, the term "package" refers to a suitable solid matrix or material such as glass, plastic, paper, foil, and the like, capable of holding the individual kit components. Thus, for example, a package can be a glass vial or prefilled syringes used to contain suitable quantities of the pharmaceutical composition. The packaging material has an external label which indicates the contents and/or purpose of the kit and its components.

II. Platforms

Described herein, in some embodiments, are platforms for generating the extracellular vesicles described herein. In some embodiments, the platforms conform to good manufacturing practices (GMP) standard. In some embodiments, the composition comprising the extracellular vesicle is generated according to good manufacturing practices (GMP). In some embodiments, the composition comprises a pathogen level that is substantially free of pathogens. In some embodiments, the composition has a contaminant level that is substantially free of contaminants. In some embodiments, the composition comprises low immunogenicity.

In some embodiments, the composition described herein is generated and isolated via hypotonic treatment and centrifugation. In some embodiments, the extracellular vesicles are isolated from mesenchymal stem cells (MSC) expressing the extracellular vesicles primarily by using hypotonic treatment such that the MSC ruptures and extracellular vesicles are released. In some instances, the MSC are resuspended in hypotonic solution to induce cell swelling. In some embodiments, the platform comprises phase-contrast microscopy to monitor cell swelling. In some embodiments, the platform comprises a homogenizer to rupture the swollen cells to release extracellular vesicles. In some embodiments, the platform comprises means for separating the ruptured cells in a gradient (e.g., a sucrose gradient) to separate out the extracellular vesicles. In some embodiments, the platform comprises other components to generate extracellular vesicles other approaches of lysing the MSC such as mild sonication, freeze-thaw, French-press, or needle-passaging. In some embodiments, the platform comprises centrifuges to centrifuge and isolate the fraction comprising the extracellular vesicles. In some embodiments, the platform comprises means for separating a fraction comprising the extracellular vesicle by floatation in a discontinuous sucrose density gradient.

In some embodiments, the platform comprises means for generating the extracellular vesicles by extrusion. In some embodiments, the extrusion process separates and isolates the extracellular vesicles based on the sizes or diameters of the extracellular vesicles. Exemplary extrusion process comprises the use of membranes with various pore sizes. The membranes can separate the extracellular vesicles based on the sizes or diameters of the extracellular vesicles from a solution comprising the ruptured MSC. Extracellular vesicles can be further isolated and reduced in size by continued extrusion following extrusion with increasingly smaller membrane pore sizes, ranging from 150 nm to 10 nm. When the final extrusion is complete, extracellular vesicle can be are pelleted by centrifugation. In some embodiments, the platform comprises components for performing sonication, extrusion, high pressure/homogenization, microfluidization, or detergent dialysis.

In some embodiments, the platform comprises components for determining unit numbers of immune checkpoint moiety per extracellular vesicle.

III. Methods

Generating Extracellular Vesicles

Described herein, in some embodiments, are methods of generating the compositions descried herein utilizing the platforms described herein. In some embodiments, extracellular vesicles can be isolated from or secreted by a cell. For example, extracellular vesicles can be generated from lysing the cells to release the extracellular vesicles. In some cases, the cells secretes the extracellular vesicles, where the extracellular vesicles can then be isolated.

In some embodiments, the cell for generating the extracellular vesicle can be from a cell line, stem cells, primary cells, or differentiated cells. In some embodiments, the extracellular vesicle donor cells can be selected from the group consisting of human embryonic fibroblasts (HEF), dendritic cells, mesenchymal stem cells, bone marrow-derived dendritic cells, bone marrow derived stromal cells, adipose stromal cells, endothelial cells, enucleated cells, neural stem cells, immature dendritic cells, and immune cells. bone marrow stromal cells, marrow derived adult progenitor cells (MAPCs), endothelial progenitor cells (EPC), blast cells, intermediate progenitor cells formed in the subventricular zone, neural stem cells, muscle stem cells, satellite cells, liver stem cells, hematopoietic stem cells, bone marrow stromal cells, epidermal stem cells, embryonic stem cells, umbilical cord stem cells, precursor cells, muscle precursor cells, myoblast, cardiomyoblast, neural precursor cells, glial precursor cells, neuronal precursor cells, or hepatoblasts.

In some embodiments, the cell for generating the extracellular vesicles can be a genetically modified cell, where a genetic modification moiety is introduced into the modified cell. In some embodiments, at least one heterologous polynucleotide encoding a transgene is introduced into the modified cell. In some embodiments, the heterologous polynucleotide encodes any one of the immune checkpoint moiety described herein. In some embodiments, the heterologous polynucleotide encodes any one of the targeting moiety described herein. In some embodiments, the heterologous polynucleotide encodes any one of the transmembrane moiety described herein. In some embodiments, the heterologous polynucleotide encodes any one of the fusion peptide described herein. In some embodiments, the heterologous polynucleotide encodes any one of the immune evasion moiety described herein. In some embodiments, the heterologous polynucleotide can be integrated into the chromosome of the modified cell. In some embodiments, the heterologous polynucleotide is not integrated into the chromosome of the modified cell.

In some embodiments, the a genetic modification moiety regulates the expressions of the heterologous polynucleotide. In some embodiments, the a genetic modification moiety increases the expressions of the heterologous polynucleotide. In some embodiments, the genetic modification moiety comprises a CRISPR-Cas polypeptide. In some embodiments, the genetic modification moiety can be, for example, Class 1 CRISPR-associated (Cas) polypeptides, Class 2 Cas polypeptides, type I Cas polypeptides, type II Cas polypeptides, type III Cas polypeptides, type IV Cas polypeptides, type V Cas polypeptides, and type VI, CRISPR-associated RNA binding proteins, or a functional fragment thereof. Cas polypeptides suitable for use with the present disclosure can include Cas9, Cas12, Cas13, Cpf1 (or Cas12a), C2C1, C2C2 (or Cas13a), Cas13b, Cas13c, Cas13d, C2C3, Cas1, Cas1B, Cas2, Cas3, Cas4, Cas5, Cas5e (CasD), Cash, Cas6e, Cas6f, Cas7, Cas8a, Cas8al, Cas8a2, Cas8b, Cas8c, Csn1, Csx12, Cas10, Cas10d, CaslO, CaslOd, CasF, CasG, CasH, Csy1, Csy2, Csy3, Cse1 (CasA), Cse2 (CasB), Cse3 (CasE), Cse4 (CasC), Cscl, Csc2, Csa5, Csn2, Csm2, Csm3, Csm4, Csm5, Csm6, Cmr1, Cmr3, Cmr4, Cmr5, Cmr6, Csbl, Csb2, Csb3, Csx17, Csx14, Csx10, Csx16, CsaX, Csx3, Csx1, Csx15, Csf1, Csf2, Csf3, Csf4, or Cul966; any derivative thereof; any variant thereof; or any fragment thereof. In some embodiments, Cas13 can include, but are not limited to, Cas13a, Cas13b, Cas13c, and Cas 13d (e.g., CasRx). CRISPR/Cas can be DNA and/or RNA cleaving, or can exhibit reduced cleavage activity. Genetic modification moiety can be configured to complex with at least one heterologous RNA polynucleotide. In some cases, the genetic modification moiety can be fused with a transcription activator or transcription repressor.

Any suitable nuclease (e.g., endonuclease) can be used in as the genetic modification moiety. Suitable nucleases include, but are not limited to, CRISPR-associated (Cas) proteins or Cas nucleases including type I CRISPR-associated (Cas) polypeptides, type II CRISPR-associated (Cas) polypeptides, type III CRISPR-associated (Cas) polypeptides, type IV CRISPR-associated (Cas) polypeptides, type V CRISPR-associated (Cas) polypeptides, and type VI CRISPR-associated (Cas) polypeptides; zinc finger nucleases (ZFN); transcription activator-like effector nucleases (TALEN); meganucleases; RNA-binding proteins (RBP); CRISPR-associated RNA binding proteins; recombinases; flippases; transposases; Argonaute (Ago) proteins (e.g., prokaryotic Argonaute (pAgo), archaeal Argonaute (aAgo), eukaryotic Argonaute (eAgo), and Natronobacterium gregoryi Argonaute (NgAgo)); Adenosine deaminases acting on RNA (ADAR); CIRT, PUF, homing endonuclease, or any functional fragment thereof, any derivative thereof; any variant thereof; and any fragment thereof.

A genetic modification moiety as disclosed herein can be coupled (e.g., linked or fused) to additional peptide sequences which are not involved in regulating gene expression, for example linker sequences, targeting sequences, etc. The term "targeting sequence," as used herein, refers to a nucleotide sequence and the corresponding amino acid sequence which encodes a targeting polypeptide which mediates the localization (or retention) of a protein to a sub-cellular location, e.g., plasma membrane or membrane of a given organelle, nucleus, cytosol, mitochondria, endoplasmic reticulum (ER), Golgi, chloroplast, apoplast, peroxisome or other organelle. For example, a targeting sequence can direct a protein (e.g., a receptor polypeptide or an adaptor polypeptide) to a nucleus utilizing a nuclear localization signal (NLS); outside of a nucleus of a cell, for example to the cytoplasm, utilizing a nuclear export signal (NES); mitochondria utilizing a mitochondrial targeting signal; the endoplasmic reticulum (ER) utilizing an ER-retention signal; a peroxisome utilizing a peroxisomal targeting signal; plasma membrane utilizing a membrane localization signal; or combinations thereof.

A genetic modification moiety as disclosed herein can be a part of a fusion construct (e.g., a fusion protein). As used herein, "fusion" can refer to a protein and/or nucleic acid comprising one or more non-native sequences (e.g., moieties). A fusion can comprise one or more of the same non-native sequences. A fusion can comprise one or more of different non-native sequences. A fusion can be a chimera. A fusion can comprise a nucleic acid affinity tag. A fusion can comprise a barcode. A fusion can comprise a peptide affinity tag. A fusion can provide for subcellular localization of the site-directed polypeptide (e.g., a nuclear localization signal (NLS) for targeting to the nucleus, a mitochondrial localization signal for targeting to the mitochondria, a chloroplast localization signal for targeting to a chloroplast, an endoplasmic reticulum (ER) retention signal, and the like). A fusion can provide a non-native sequence (e.g., affinity tag) that can be used to track or purify. A fusion can be a small molecule such as biotin or a dye such as Alexa fluor dyes, Cyanine3 dye, Cyanine5 dye.

A fusion can refer to any protein with a functional effect. For example, a fusion protein can comprise methyltransferase activity, demethylase activity, dismutase activity, alkylation activity, depurination activity, oxidation activity, pyrimidine dimer forming activity, integrase activity, transposase activity, recombinase activity, polymerase activity (e.g., a reverse transcriptase activity), ligase activity, helicase activity, photolyase activity or glycosylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, remodelling activity, protease activity, oxidoreductase activity, transferase activity, hydrolase activity, lyase activity, isomerase activity, synthase activity, synthetase activity, or demyristoylation activity. An effector protein can modify a genomic locus. A fusion protein can be a fusion in a Cas protein. A fusion protein can be a non-native sequence in a Cas protein.

In some embodiments, the genetic modification moiety can be fused to one or more transcription repressor domains, activator domains, epigenetic domains, recombinase domains, transposase domains, flippase domains, nickase domains, or any combination thereof. The activator domain can include one or more tandem activation domains located at the carboxyl terminus of the protein. In some cases, the genetic modification moiety includes one or more tandem repressor domains located at the carboxyl terminus of the protein. Non-limiting exemplary activation domains include GAL4, herpes simplex activation domain VP16, VP64 (a tetramer of the herpes simplex activation domain VP16), NF-κB p65 subunit, Epstein-Barr virus R transactivator (Rta) and are described in Chavez et al., Nat Methods, 2015, 12(4):326-328. Non-limiting exemplary repression domains include the KRAB (Kruppel-associated box) domain of Kox1, the Mad mSIN3 interaction domain (SID), ERF repressor domain (ERD), and are described in Chavez et al., Nat Methods, 2015, 12(4):326-328. In some embodiments, the genetic modification moiety includes one or more tandem repressor domains located at the amino terminus of the protein.

In some embodiments, the nuclease disclosed herein can be a protein that lacks nucleic acid cleavage activity. In some cases, a Cas protein is a dead Cas protein. A dead Cas protein can be a protein that lacks nucleic acid cleavage activity. A Cas protein can comprise a modified form of a wild type Cas protein. The modified form of the wild type Cas protein can comprise an amino acid change (e.g., deletion, insertion, or substitution) that reduces the nucleic acid-cleaving activity of the Cas protein. For example, the modified form of the Cas protein can have less than 90%, less than 80%, less than 70%, less than 60%, less than 50%, less than 40%, less than 30%, less than 20%, less than 10%, less than 5%, or less than 1% of the nucleic acid-cleaving activity of the wild-type Cas protein (e.g., Cas9 from *S. pyogenes*). The modified form of Cas protein can have no substantial nucleic acid-cleaving activity. When a Cas protein is a modified form that has no substantial nucleic acid-cleaving activity, it can be referred to as enzymatically inactive and/or "dead" (abbreviated by "d"). A dead Cas protein (e.g., dCas, dCas9) can bind to a target polynucleotide but may not cleave the target polynucleotide. In some aspects, a dead Cas protein is a dead Cas9 protein.

In some embodiments, a dCas (e.g., dCas9) polypeptide can associate with a single guide RNA (sgRNA) to activate or repress transcription of target DNA. sgRNAs can be introduced into cells expressing the engineered chimeric receptor polypeptide. In some cases, such cells contain one or more different sgRNAs that target the same nucleic acid. In other cases, the sgRNAs target different nucleic acids in the cell.

In some embodiments, the genetic modification moiety can comprise a catalytically inactive Cas polypeptide, where the nuclease activity of the Cas polypeptide is eliminated or substantially eliminated.

In some instances, the genetic modification moiety can comprise a catalytically inactivated Cas9 (dCas9), any derivative thereof; any variant thereof; or any fragment thereof.

In some instances, the genetic modification moiety can comprise a catalytically inactivated Cas12 (dCas12), any derivative thereof; any variant thereof; or any fragment thereof.

In some instances, the genetic modification moiety can comprise a catalytically inactivated Cas13 (dCas13); any derivative thereof; any variant thereof or any fragment thereof.

In some embodiments, the genetic modification moiety can be complexed with the at least one heterologous polynucleotide as described herein. In some embodiments, the at least one heterologous polynucleotide can be either heterologous DNA polynucleotide or heterologous RNA polynucleotide. In some embodiments, the genetic modification moiety can be complexed with at least one heterologous RNA polynucleotide. In some embodiments, the complexing with the at least one heterologous RNA polynucleotide direct and target the genetic modification moiety to the portion of the heterologous polynucleotide.

In some cases, the compositions and methods described herein comprise at least one heterologous polynucleotide. In some cases, the compositions and methods described herein comprise a plurality of heterologous nucleic acids. In some embodiments, the polynucleotide can be deoxyribonucleic acid (DNA). In some cases, the DNA sequence can be single-stranded or doubled-stranded. In some embodiments, the at least one heterologous nucleic acid polynucleotide can be ribonucleic acid (RNA).

In some embodiments, the genetic modification moiety can be complexed with the at least one heterologous RNA polynucleotide. The at least one heterologous RNA polynucleotide can comprise a nucleic-acid targeting region that comprises a complementary sequence to a nucleic acid sequence of the heterologous polynucleotide that encodes any one of the moieties described herein for specificity of the genetic modification moiety-dependent targeting. In some embodiments, the at least one heterologous RNA polynucleotide can be guide nucleic acid (or guide RNA) comprising two separate nucleic acid molecules, which can be referred to as a double guide nucleic acid or a single nucleic acid molecule, which can be referred to as a single guide nucleic acid (e.g., sgRNA). In some embodiments, the guide nucleic acid is a single guide nucleic acid comprising a fused CRISPR RNA (crRNA) and a transactivating crRNA (tracrRNA). In some embodiments, the guide nucleic acid is a single guide nucleic acid comprising a crRNA. In some embodiments, the guide nucleic acid is a single guide nucleic acid comprising a crRNA but lacking a tracRNA. In some embodiments, the guide nucleic acid is a double guide nucleic acid comprising non-fused crRNA and tracrRNA. An exemplary double guide nucleic acid can comprise a crRNA-like molecule and a tracrRNA-like molecule. An exemplary single guide nucleic acid can comprise a crRNA-like molecule. An exemplary single guide nucleic acid can comprise a fused crRNA-like molecule and a tracrRNA-like molecule.

A crRNA can comprise the nucleic acid-targeting segment (e.g., spacer region) of the guide nucleic acid and a stretch of nucleotides that can form one half of a double-stranded duplex of the Cas protein-binding segment of the guide nucleic acid.

A tracrRNA can comprise a stretch of nucleotides that forms the other half of the double-stranded duplex of the Cas protein-binding segment of the gRNA. A stretch of nucleotides of a crRNA can be complementary to and hybridize with a stretch of nucleotides of a tracrRNA to form the double-stranded duplex of the Cas protein-binding domain of the guide nucleic acid.

The crRNA and tracrRNA can hybridize to form a guide nucleic acid. The crRNA can also provide a single-stranded nucleic acid targeting segment (e.g., a spacer region) that hybridizes to a target nucleic acid recognition sequence (e.g., protospacer). The sequence of a crRNA, including spacer region, or tracrRNA molecule can be designed to be specific to the species in which the guide nucleic acid is to be used.

In some embodiments, the nucleic acid-targeting region of a guide nucleic acid can be between 18 to 72 nucleotides in length. The nucleic acid-targeting region of a guide nucleic acid (e.g., spacer region) can have a length of from about 12 nucleotides to about 100 nucleotides. For example, the nucleic acid-targeting region of a guide nucleic acid (e.g., spacer region) can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, from about 12 nt to about 19 nt, from about 12 nt to about 18 nt, from about 12 nt to about 17 nt, from about 12 nt to about 16 nt, or from about 12 nt to about 15 nt. Alternatively, the DNA-targeting segment can have a length of from about 18 nt to about 20 nt, from about 18 nt to about 25 nt, from about 18 nt to about 30 nt, from about 18 nt to about 35 nt, from about 18 nt to about 40 nt, from about 18 nt to about 45 nt, from about 18 nt to about 50 nt, from about 18 nt to about 60 nt, from about 18 nt to about 70 nt, from about 18 nt to about 80 nt, from about 18 nt to about 90 nt, from about 18 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt. The length of the nucleic acid-targeting region can be at least 5, 10, 15, 16, 17, 18, 19, 20, 21, 22, 23, 24, 25, 30 or more nucleotides. The length of the nucleic acid-targeting region (e.g., spacer sequence) can be at most 5, 10, 15, 16, 17, 18, 19, 20, 21, 22, 23, 24, 25, 30 or more nucleotides.

In some embodiments, the nucleic acid-targeting region of a guide nucleic acid (e.g., spacer) is 20 nucleotides in length. In some embodiments, the nucleic acid-targeting region of a guide nucleic acid is 19 nucleotides in length. In some embodiments, the nucleic acid-targeting region of a guide nucleic acid is 18 nucleotides in length. In some embodiments, the nucleic acid-targeting region of a guide nucleic acid is 17 nucleotides in length. In some embodiments, the nucleic acid-targeting region of a guide nucleic acid is 16 nucleotides in length. In some embodiments, the nucleic acid-targeting region of a guide nucleic acid is 21 nucleotides in length. In some embodiments, the nucleic acid-targeting region of a guide nucleic acid is 22 nucleotides in length.

The nucleotide sequence of the guide nucleic acid that is complementary to a nucleotide sequence (target sequence) of the target nucleic acid can have a length of, for example, at least about 12 nt, at least about 15 nt, at least about 18 nt, at least about 19 nt, at least about 20 nt, at least about 25 nt, at least about 30 nt, at least about 35 nt or at least about 40 nt. The nucleotide sequence of the guide nucleic acid that is complementary to a nucleotide sequence (target sequence) of the target nucleic acid can have a length of from about 12 nucleotides (nt) to about 80 nt, from about 12 nt to about 50 nt, from about 12 nt to about 45 nt, from about 12 nt to about 40 nt, from about 12 nt to about 35 nt, from about 12 nt to about 30 nt, from about 12 nt to about 25 nt, from about 12 nt to about 20 nt, from about 12 nt to about 19 nt, from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, or from about 20 nt to about 60 nt.

A protospacer sequence of a targeted polynucleotide can be identified by identifying a PAM within a region of interest and selecting a region of a desired size upstream or downstream of the PAM as the protospacer. A corresponding spacer sequence can be designed by determining the complementary sequence of the protospacer region.

A spacer sequence can be identified using a computer program (e.g., machine readable code). The computer program can use variables such as predicted melting temperature, secondary structure formation, and predicted annealing temperature, sequence identity, genomic context, chromatin accessibility, % GC, frequency of genomic occurrence, methylation status, presence of SNPs, and the like.

The percent complementarity between the nucleic acid-targeting sequence (e.g., a spacer sequence of the at least one heterologous polypeptide as disclosed herein) and the target nucleic acid (e.g., a protospacer sequence of the heterologous polynucleotide encoding any one of the moieties described herein) can be at least 50%, at least 60%, at least 70%, at least 75%, at least 80%, at least 85%, at least 90%, at least 95%, at least 97%, at least 98%, at least 99%, or 100%. The percent complementarity between the nucleic acid-targeting sequence and the target nucleic acid can be at least 60%, at least 70%, at least 75%, at least 80%, at least 85%, at least 90%, at least 95%, at least 97%, at least 98%, at least 99%, or 100% over about 20 contiguous nucleotides.

The Cas protein-binding segment of a guide nucleic acid can comprise two stretches of nucleotides (e.g., crRNA and tracrRNA) that are complementary to one another. The two stretches of nucleotides (e.g., crRNA and tracrRNA) that are complementary to one another can be covalently linked by intervening nucleotides (e.g., a linker in the case of a single guide nucleic acid). The two stretches of nucleotides (e.g., crRNA and tracrRNA) that are complementary to one another can hybridize to form a double stranded RNA duplex or hairpin of the Cas protein-binding segment, thus resulting in a stem-loop structure. The crRNA and the tracrRNA can be covalently linked via the 3' end of the crRNA and the 5' end of the tracrRNA. Alternatively, tracrRNA and crRNA can be covalently linked via the 5' end of the tracrRNA and the 3' end of the crRNA.

The Cas protein binding segment of a guide nucleic acid can have a length of from about 10 nucleotides to about 100 nucleotides, e.g., from about 10 nucleotides (nt) to about 20 nt, from about 20 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. For example, the Cas protein-binding segment of a guide nucleic acid can have a length of from about 15 nucleotides (nt) to about 80 nt, from about 15 nt to about 50 nt, from about 15 nt to about 40 nt, from about 15 nt to about 30 nt or from about 15 nt to about 25 nt.

The dsRNA duplex of the Cas protein-binding segment of the guide nucleic acid can have a length from about 6 base pairs (bp) to about 50 bp. For example, the dsRNA duplex of the protein-binding segment can have a length from about 6 bp to about 40 bp, from about 6 bp to about 30 bp, from about 6 bp to about 25 bp, from about 6 bp to about 20 bp, from about 6 bp to about 15 bp, from about 8 bp to about 40 bp, from about 8 bp to about 30 bp, from about 8 bp to about 25 bp, from about 8 bp to about 20 bp or from about 8 bp to about 15 bp. For example, the dsRNA duplex of the Cas protein-binding segment can have a length from about from about 8 bp to about 10 bp, from about 10 bp to about 15 bp, from about 15 bp to about 18 bp, from about 18 bp to about 20 bp, from about 20 bp to about 25 bp, from about 25 bp to about 30 bp, from about 30 bp to about 35 bp, from about 35 bp to about 40 bp, or from about 40 bp to about 50 bp.

In some embodiments, the dsRNA duplex of the Cas protein-binding segment can have a length of 36 base pairs. The percent complementarity between the nucleotide sequences that hybridize to form the dsRNA duplex of the protein-binding segment can be at least about 60%. For example, the percent complementarity between the nucleotide sequences that hybridize to form the dsRNA duplex of the protein-binding segment can be at least about 65%, at least about 70%, at least about 75%, at least about 80%, at least about 85%, at least about 90%, at least about 95%, at least about 98%, or at least about 99%. In some cases, the percent complementarity between the nucleotide sequences that hybridize to form the dsRNA duplex of the protein-binding segment is 100%.

The linker (e.g., that links a crRNA and a tracrRNA in a single guide nucleic acid) can have a length of from about 3 nucleotides to about 100 nucleotides. For example, the linker can have a length of from about 3 nucleotides (nt) to about 90 nt, from about 3 nucleotides (nt) to about 80 nt, from about 3 nucleotides (nt) to about 70 nt, from about 3 nucleotides (nt) to about 60 nt, from about 3 nucleotides (nt) to about 50 nt, from about 3 nucleotides (nt) to about 40 nt, from about 3 nucleotides (nt) to about 30 nt, from about 3 nucleotides (nt) to about 20 nt or from about 3 nucleotides (nt) to about 10 nt. For example, the linker can have a length of from about 3 nt to about 5 nt, from about 5 nt to about 10 nt, from about 10 nt to about 15 nt, from about 15 nt to about 20 nt, from about 20 nt to about 25 nt, from about 25 nt to about 30 nt, from about 30 nt to about 35 nt, from about 35 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt. In some embodiments, the linker of a DNA-targeting RNA is 4 nt.

Guide nucleic acids of the disclosure can include modifications or sequences that provide for additional desirable features (e.g., modified or regulated stability; subcellular targeting; tracking with a fluorescent label; a binding site for a protein or protein complex; and the like). Examples of such modifications include, for example, a 5' cap (a 7-methylguanylate cap (m7G)); a 3' polyadenylated tail (a 3' poly(A) tail); a riboswitch sequence (e.g., to allow for regulated stability and/or regulated accessibility by proteins and/or protein complexes); a stability control sequence; a sequence that forms a dsRNA duplex (a hairpin)); a modification or sequence that targets the RNA to a subcellular location (e.g., nucleus, mitochondria, chloroplasts, and the like); a modification or sequence that provides for tracking (e.g., direct conjugation to a fluorescent molecule, conjugation to a moiety that facilitates fluorescent detection, a sequence that allows for fluorescent detection, and so forth);

a modification or sequence that provides a binding site for proteins (e.g., proteins that act on DNA, including transcriptional activators, transcriptional repressors, DNA methyl transferases, DNA demethylases, histone acetyltransferases, histone deacetylases, and combinations thereof.

A guide nucleic acid can comprise one or more modifications (e.g., a base modification, a backbone modification), to provide the nucleic acid with a new or enhanced feature (e.g., improved stability). A guide nucleic acid can comprise a nucleic acid affinity tag. A nucleoside can be a base-sugar combination. The base portion of the nucleotide can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming guide nucleic acids, the phosphate groups can covalently link adjacent nucleosides to one another to form a linear polymeric compound. In turn, the respective ends of this linear polymeric compound can be further joined to form a circular compound; however, linear compounds can be suitable. In addition, linear compounds can have internal nucleotide base complementarity and can therefore fold in a manner as to produce a fully or partially double-stranded compound. Further, within guide nucleic acids, the phosphate groups can commonly be referred to as forming the internucleoside backbone of the guide nucleic acid. The linkage or backbone of the guide nucleic acid can be a 3' to 5' phosphodiester linkage.

A guide nucleic acid can comprise a modified backbone and/or modified internucleoside linkages. Modified backbones can include those that retain a phosphorus atom in the backbone and those that do not have a phosphorus atom in the backbone.

Suitable modified guide nucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage. Suitable guide nucleic acids having inverted polarity can comprise a single 3' to 3' linkage at the 3'-most internucleotide linkage (such as a single inverted nucleoside residue in which the nucleobase is missing or has a hydroxyl group in place thereof). Various salts (e.g., potassium chloride or sodium chloride), mixed salts, and free acid forms can also be included.

A guide nucleic acid can comprise one or more phosphorothioate and/or heteroatom internucleoside linkages, in particular —CH2-NH—O—CH2-, —CH2-N(CH3)-O—CH2- (a methylene (methylimino) or MMI backbone), —CH2-O—N(CH3)-CH2-, —CH2-N(CH3)-N(CH3)-CH2- and —O—N(CH3)-CH2-CH2- (wherein the native phosphodiester internucleotide linkage is represented as —O—P(=O)(OH)—O—CH2-).

A guide nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage replaces a phosphodiester linkage.

A guide nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A guide nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A guide nucleic acid can comprise linked morpholino units (morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be non-ionic mimics of guide nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A guide nucleic acid can comprise one or more substituted sugar moieties. Suitable polynucleotides can comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted C1 to C10 alkyl or C2 to C10 alkenyl and alkynyl. Particularly suitable are O((CH2)nO) mCH3, O(CH2)nOCH3, O(CH2)nNH2, O(CH2)nCH3, O(CH2)nONH2, and O(CH2)nON((CH2)nCH3)$_2$, where n and m are from 1 to about 10. A sugar substituent group can be selected from: C1 to C10 lower alkyl, substituted lower alkyl, alkenyl, alkynyl, alkaryl, aralkyl, O-alkaryl or O-aralkyl, SH, SCH3, OCN, Cl, Br, CN, CF$_3$, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an guide nucleic acid, or a group for improving the pharmacodynamic properties of an guide nucleic acid, and other substituents having similar properties. A suitable modification can include 2'-methoxyethoxy (2'-O—CH2 CH2OCH3, also known as 2'-O-(2-methoxyethyl) or 2'-MOE, an alkoxyalkoxy group). A further suitable modification can include 2'-dimethylaminooxyethoxy, (a O(CH2) 2ON(CH3)$_2$ group, also known as 2'-DMAOE), and 2'-dimethylaminoethoxyethoxy (also known as 2'-O-dimethyl-amino-ethoxy-ethyl or 2'-DMAEOE), 2'-O—CH2-O—CH2-N(CH3)2.

Other suitable sugar substituent groups can include methoxy (—O—CH3), aminopropoxy CH2 CH2NH2), allyl (—CH2-CH═CH2), —O-allyl CH2-CH═CH2) and fluoro (F). 2'-sugar substituent groups can be in the arabino (up) position or ribo (down) position. A suitable 2'-arabino modification is 2'-F. Similar modifications can also be made at other positions on the oligomeric compound, particularly the 3' position of the sugar on the 3' terminal nucleoside or in 2'-5' linked nucleotides and the 5' position of 5' terminal nucleotide. Oligomeric compounds can also have sugar mimetics such as cyclobutyl moieties in place of the pentofuranosyl sugar.

A guide nucleic acid can also include nucleobase (or "base") modifications or substitutions. As used herein, "unmodified" or "natural" nucleobases can include the purine bases, (e.g., adenine (A) and guanine (G)), and the pyrimidine bases, (e.g., thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g., 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (H¬pyrido(3',2':4,5)pyrrolo(2,3-d)pyrimidin-2-one).

Heterocyclic base moieties can include those in which the purine or pyrimidine base is replaced with other heterocycles, for example 7-deaza-adenine, 7-deazaguanosine, 2-aminopyridine and 2-pyridone. Nucleobases can be useful for increasing the binding affinity of a polynucleotide compound. These can include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions can increase nucleic acid duplex stability by 0.6-1.2° C. and can be suitable base substitutions (e.g., when combined with 2'-O-methoxyethyl sugar modifications).

A modification of a guide nucleic acid can comprise chemically linking to the guide nucleic acid one or more moieties or conjugates that can enhance the activity, cellular distribution or cellular uptake of the guide nucleic acid. These moieties or conjugates can include conjugate groups covalently bound to functional groups such as primary or secondary hydroxyl groups. Conjugate groups can include, but are not limited to, intercalators, reporter molecules, polyamines, polyamides, polyethylene glycols, polyethers, groups that enhance the pharmacodynamic properties of oligomers, and groups that can enhance the pharmacokinetic properties of oligomers. Conjugate groups can include, but are not limited to, cholesterols, lipids, phospholipids, biotin, phenazine, folate, phenanthridine, anthraquinone, acridine, fluoresceins, rhodamines, coumarins, and dyes. Groups that enhance the pharmacodynamic properties include groups that improve uptake, enhance resistance to degradation, and/or strengthen sequence-specific hybridization with the target nucleic acid. Groups that can enhance the pharmacokinetic properties include groups that improve uptake, distribution, metabolism or excretion of a nucleic acid. Conjugate moieties can include but are not limited to lipid moieties such as a cholesterol moiety, cholic acid a thioether, (e.g., hexyl-S-tritylthiol), a thiocholesterol, an aliphatic chain (e.g., dodecandiol or undecyl residues), a phospholipid (e.g., di-hexadecyl-rac-glycerol or triethylammonium 1,2-di-O-hexadecyl-rac-glycero-3-H-phosphonate), a polyamine or a polyethylene glycol chain, or adamantane acetic acid, a palmityl moiety, or an octadecylamine or hexylamino-carbonyl-oxycholesterol moiety.

Described herein, in some embodiments, are heterologous RNA polynucleotides comprising crRNAs. In some embodiments, the cRNA comprises targeting sequence that is complementary to the heterologous polynucleotide encoding any one of the moieties described herein.

In some embodiments, the crRNA comprises 5 nt to 100 nt. In some embodiments, the crRNA comprises 5 nt to 6 nt, 5 nt to 7 nt, 5 nt to 8 nt, 5 nt to 9 nt, 5 nt to 10 nt, 5 nt to 15 nt, 5 nt to 20 nt, 5 nt to 25 nt, 5 nt to 50 nt, 5 nt to 100 nt, 6 nt to 7 nt, 6 nt to 8 nt, 6 nt to 9 nt, 6 nt to 10 nt, 6 nt to 15 nt, 6 nt to 20 nt, 6 nt to 25 nt, 6 nt to 50 nt, 6 nt to 100 nt, 7 nt to 8 nt, 7 nt to 9 nt, 7 nt to 10 nt, 7 nt to 15 nt, 7 nt to 20 nt, 7 nt to 25 nt, 7 nt to 50 nt, 7 nt to 100 nt, 8 nt to 9 nt, 8 nt to 10 nt, 8 nt to 15 nt, 8 nt to 20 nt, 8 nt to 25 nt, 8 nt to 50 nt, 8 nt to 100 nt, 9 nt to 10 nt, 9 nt to 15 nt, 9 nt to 20 nt, 9 nt to 25 nt, 9 nt to 50 nt, 9 nt to 100 nt, 10 nt to 15 nt, 10 nt to 20 nt, 10 nt to 25 nt, 10 nt to 50 nt, 10 nt to 100 nt, 15 nt to 20 nt, 15 nt to 25 nt, 15 nt to 50 nt, 15 nt to 100 nt, 20 nt to 25 nt, 20 nt to 50 nt, 20 nt to 100 nt, 25 nt to 50 nt, 25 nt to 100 nt, or 50 nt to 100 nt. In some embodiments, the crRNA comprises 5 nt, 6 nt, 7 nt, 8 nt, 9 nt, 10 nt, 15 nt, 20 nt, 25 nt, 50 nt, or 100 nt. In some embodiments, the crRNA comprises at least 5 nt, 6 nt, 7 nt, 8 nt, 9 nt, 10 nt, 15 nt, 20 nt, 25 nt, or 50 nt. In some embodiments, the crRNA comprises at most 6 nt, 7 nt, 8 nt, 9 nt, 10 nt, 15 nt, 20 nt, 25 nt, 50 nt, or 100 nt. In some embodiments, the crRNA comprises at least 5 nt to 100 nt. In some embodiments, the crRNA comprises at least 5 nt to 6 nt, 5 nt to 7 nt, 5 nt to 8 nt, 5 nt to 9 nt, 5 nt to 10 nt, 5 nt to 15 nt, 5 nt to 20 nt, 5 nt to 25 nt, 5 nt to 50 nt, 5 nt to 100 nt, 6 nt to 7 nt, 6 nt to 8 nt, 6 nt to 9 nt, 6 nt to 10 nt, 6 nt to 15 nt, 6 nt to 20 nt, 6 nt to 25 nt, 6 nt to 50 nt, 6 nt to 100 nt, 7 nt to 8 nt, 7 nt to 9 nt, 7 nt to 10 nt, 7 nt to 15 nt, 7 nt to 20 nt, 7 nt to 25 nt, 7 nt to 50 nt, 7 nt to 100 nt, 8 nt to 9 nt, 8 nt to 10 nt, 8 nt to 15 nt, 8 nt to 20 nt, 8 nt to 25 nt, 8 nt to 50 nt, 8 nt to 100 nt, 9 nt to 10 nt, 9 nt to 15 nt, 9 nt to 20 nt, 9 nt to 25 nt, 9 nt to 50 nt, 9 nt to 100 nt, 10 nt to 15 nt, 10 nt to 20 nt, 10 nt to 25 nt, 10 nt to 50 nt, 10 nt to 100 nt, 15 nt to 20 nt, 15 nt to 25 nt, 15 nt to 50 nt, 15 nt to 100 nt, 20 nt to 25 nt, 20 nt to 50 nt, 20 nt to 100 nt, 25 nt to 50 nt, 25 nt to 100 nt, or 50 nt to 100 nt. In some embodiments, the crRNA comprises at least 5 nt, 6 nt, 7 nt, 8 nt, 9 nt, 10 nt, 15 nt, 20 nt, 25 nt, 50 nt, or 100 nt. In some embodiments, the crRNA comprises at least at least 5 nt, 6 nt, 7 nt, 8 nt, 9 nt, 10 nt, 15 nt, 20 nt, 25 nt, or 50 nt. In some embodiments, the crRNA comprises at least at most 6 nt, 7 nt, 8 nt, 9 nt, 10 nt, 15 nt, 20 nt, 25 nt, 50 nt, or 100 nt. In some embodiments, the crRNA comprises at most 5 nt to 100 nt. In some embodiments, the crRNA comprises at most 5 nt to 6 nt, 5 nt to 7 nt, 5 nt to 8 nt, 5 nt to 9 nt, 5 nt to 10 nt, 5 nt to 15 nt, 5 nt to 20 nt, 5 nt to 25 nt, 5 nt to 50 nt, 5 nt to 100 nt, 6 nt to 7 nt, 6 nt to 8 nt, 6 nt to 9 nt, 6 nt to 10 nt, 6 nt to 15 nt, 6 nt to 20 nt, 6 nt to 25 nt, 6 nt to 50 nt, 6 nt to 100 nt, 7 nt to 8 nt, 7 nt to 9 nt, 7 nt to 10 nt, 7 nt to 15 nt, 7 nt to 20 nt, 7 nt to 25 nt, 7 nt to 50 nt, 7 nt to 100 nt, 8 nt to 9 nt, 8 nt to 10 nt, 8 nt to 15 nt, 8 nt to 20 nt, 8 nt to 25 nt, 8 nt to 50 nt, 8 nt to 100 nt, 9 nt to 10 nt, 9 nt to 15 nt, 9 nt to 20 nt, 9 nt to 25 nt, 9 nt to 50 nt, 9 nt to 100 nt, 10 nt to 15 nt, 10 nt to 20 nt, 10 nt to 25 nt, 10 nt to 50 nt, 10 nt to 100 nt, 15 nt to 20 nt, 15 nt to 25 nt, 15 nt to 50 nt, 15 nt to 100 nt, 20 nt to 25 nt, 20 nt to 50 nt, 20 nt to 100 nt, 25 nt to 50 nt, 25 nt to 100 nt, or 50 nt to 100 nt. In some embodiments, the crRNA comprises at most 5 nt, 6 nt, 7 nt, 8 nt, 9 nt, 10 nt, 15 nt, 20 nt, 25 nt, 50 nt, or 100 nt. In some embodiments, the crRNA comprises at most at least 5 nt, 6 nt, 7 nt, 8 nt, 9 nt, 10 nt, 15 nt, 20 nt, 25 nt, or 50 nt. In some embodiments, the crRNA comprises at most at most 6 nt, 7 nt, 8 nt, 9 nt, 10 nt, 15 nt, 20 nt, 25 nt, 50 nt, or 100 nt.

In some embodiments, the genetic modification moiety and the heterologous polynucleotide can be delivered into the cell via the use of expression vectors. In the context of an expression vector, the vector can be readily introduced into a host cell, e.g., mammalian, bacterial, yeast, or insect cell by any method in the art. For example, the expression vector can be transferred into a host cell by physical, chemical, or biological means. In some embodiments, the genetic modification moiety and the heterologous polynucleotide can be delivered into the cell via physical methods such as calcium phosphate precipitation, lipofection, particle bombardment, microinjection, gene gun, electroporation, and the like. Methods for producing cells comprising vectors and/or exogenous nucleic acids are suitable for methods herein (see, e.g., Sambrook et al., 2012, Molecular Cloning: A Laboratory Manual, volumes 1-4, Cold Spring Harbor Press, NY). One method for the introduction of a polynucleotide into a host cell is calcium phosphate transfection. In some embodiments, the genetic modification moiety and the heterologous polynucleotide can be delivered into the cell via biological methods such as the use of DNA and RNA vectors. Viral vectors, and especially retroviral vectors, have become the most widely used method for inserting genes into mammalian, e.g., human cells. Other viral vectors, in some embodiments, are derived from lentivirus, poxviruses, herpes simplex virus I, adenoviruses and adeno-associated viruses, and the like. Exemplary viral vectors include retroviral vectors, adenoviral vectors, adeno-associated viral vectors (AAVs), pox vectors, parvoviral vectors, baculovirus vectors, measles viral vectors, or herpes simplex virus vectors (HSVs). In some instances, the retroviral vectors include gamma-retroviral vectors such as vectors derived from the Moloney Murine Keukemia Virus (MoMLV, MMLV, MuLV, or MLV) or the Murine Steam cell Virus (MSCV) genome. In some instances, the retroviral vectors also include lentiviral vectors such as those derived from the human immunodeficiency virus (HIV) genome. In some instances, AAV vectors include AAV1, AAV2, AAV4, AAV5, AAV6, AAV7, AAV8, or AAV9 serotype. In some instances, viral vector is a chimeric viral vector, comprising viral portions from two or more viruses. In additional instances, the viral vector is a recombinant viral vector. In some embodiments, the genetic modification moiety and the heterologous polynucleotide can be delivered into the cell via chemical means such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable sub-micron sized delivery system. In some embodiments, the genetic modification moiety and the heterologous polynucleotide can be delivered into the cell via a non-viral delivery system. Non-viral delivery system can be liposome. The use of lipid formulations is contemplated for the introduction of the nucleic acids into a host cell (in vitro, ex vivo or in vivo). In another aspect, the nucleic acid is associated with a lipid. The nucleic acid associated with a lipid, in some embodiments, is encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, in some embodiments, they are present in a bilayer structure, as micelles, or with a "collapsed" structure. Alternately, they are simply be interspersed in a solution, possibly forming aggregates that are not uniform in size or shape. Lipids are fatty substances which are, in some embodiments, naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes. Lipids suitable for use are obtained from commercial sources. For example, in some embodiments, dimyristyl phosphatidylcholine ("DMPC") is obtained from Sigma, St. Louis, Mo.; in some embodiments, dicetyl phosphate ("DCP") is obtained from K & K Laboratories (Plainview, N.Y.); cholesterol ("Choi"), in some embodiments, is obtained from Calbiochem-Behring; dimyristyl phosphatidylglycerol ("DMPG") and other lipids are often obtained from Avanti Polar Lipids, Inc.

(Birmingham, Ala.). Stock solutions of lipids in chloroform or chloroform/methanol are often stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes are often characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids, in some embodiments, assume a micellar structure or merely exist as nonuniform aggregates of lipid molecules. Also contemplated are lipofectamine-nucleic acid complexes. In some embodiments, the genetic modification moiety and the heterologous polynucleotide can be delivered into the cell can be packaged and delivered to the cell via extracellular vesicles. The extracellular vesicles can be any membrane-bound particles. In some embodiments, the extracellular vesicles can be any membrane-bound particles secreted by at least one cell. In some instances, the extracellular vesicles can be any membrane-bound particles synthesized in vitro. In some instances, the extracellular vesicles can be any membrane-bound particles synthesized without a cell. In some cases, the extracellular vesicles can be exosomes, microvesicles, retrovirus-like particles, apoptotic bodies, apoptosomes, oncosomes, exophers, enveloped viruses, exomeres, or other very large extracellular vesicles.

Identifying and Isolating Homogenous Population of Extracellular Vesicles

Described herein, in some embodiments, are methods for utilizing the platforms described herein to generate compositions comprising a homogeneous population of extracellular vesicles. In some embodiments, the method identifies and isolates the homogenous population of extracellular vesicles based on the dimensions (e.g. diameters or sizes) of the extracellular vesicles. In some embodiments, the method identifies and isolates the homogenous population of extracellular vesicles based on the mass of the extracellular vesicles. In some embodiments, the method identifies and isolates the homogeneous population of extracellular vesicles based on the number of units of immune checkpoint moiety encapsulated, secreted, or expressed on the surface of the extracellular vesicle. In some embodiments, the method identifies and isolates the homogenous population of extracellular vesicles based on a combination of the dimensions and the number of units if immune checkpoint moiety encapsulated, secreted, or expressed on the surface of the extrasellar vesicle. In some embodiments, the method identifies and isolates the homogenous population of extracellular vesicles based on a combination of dimensions and the number of unit of immune checkpoint moiety expressed on the surface of the extracellular vesicle.

In some embodiments, the method of identifying and isolating the homogenous population of extracellular vesicles comprises performing differential ultracentrifugation to isolate a homogenous population of extracellular vesicle based on density. In some embodiments the method comprises performing filtration or ultrafiltration to isolate homogenous population of extracellular vesicles based on weights or sizes. In some embodiments, the method comprises performing HPLC. In some embodiments, the method comprises performing extracellular vesicle precipitation, where water-excluding polymers such as polyethylene glycol (PEG) can tie up water molecules and force less soluble components out of solution. As such, the precipitate containing extracellular vesicle cam ne isolated by means of either low-speed centrifugation or filtration. In some embodiments, the method comprises performing affinity-based capture by capturing the extracellular vesicles by immunoaffinity. Examples of proteins or epitope displayed on the surface of the extracellular vesicles include CD9, CD63. CD81. Alix, caveolin-1, CD41, CD4, flotillin, Rab5, HSC70, and Lamp-3. In some embodiments, the method comprises performing microfluidics-based isolation method for extracellular vesicle for identifying and isolating a homogenous population of extracellular vesicle based on size, density, and immunoaffinity, innovative sorting mechanisms such as acoustic, electrophoretic and electromagnetic manipulations can be implemented. With the use of such devices, significant reductions in sample volume, reagent consumption, and isolation time are expected.

In some embodiments, the method of identifying and isolating the homogenous population of extracellular vesicles comprises basing on the number of immune checkpoint moiety expressed on the surface of the extracellular vesicle. In some embodiments, the method comprises immunoassay, where antibody recognizing the immune checkpoint moiety is used. In some embodiments, the antibody is conjugated to a detectable moiety. In some embodiments, the signal detected from the antibody recognizing and binding to the immune checkpoint moiety correlates with the number of immune checkpoint moiety expressed on the surface of the extracellular vesicle. Exemplary detectable moiety includes an enzymatic moiety (e.g., horseradish peroxidase (HRP), beta-galactosidase, alkaline phosphatase, etc), fluorescent dye, luminescent moiety, radioactive moiety, colorimetric label, colored latex particle or nanoparticle, and metal-conjugated moiety such as metallic nanolayer, metallic nanoparticle, or metallic nanoshell-conjugated moiety. In some embodiments, the detectable moiety is directly or indirectly tagged for a colorimetric assay (e.g., for detection of HRP or beta-galactosidase activity), visual inspection using light microscopy, immunofluorescence microscopy, confocal microscopy, by flow cytometry (FACS), autoradiography electron microscopy, immunostaining, or subcellular fractionation.

In some embodiments, the method of identifying and isolating the homogenous population of extracellular vehicles comprises identifying and isolating the homogenous population of extracellular vesicles based on both diameter and number of units of immune checkpoint moiety expressed on the surface of the extracellular vesicle. For example, the method identifies and isolates a homogenous population of extracellular vesicles comprising a diameter of about 50 nm and about 2000 units of immune checkpoint moiety expressed on the surface of the extracellular vesicles. In some embodiments, the method identifies and isolates a homogenous population of extracellular vesicles comprising a diameter of about 10 nm, 20 nm, 30 nm, 40 nm, 50 nm, 60 nm, 70, nm, 80 nm, 90 nm, 100 nm, 110 nm, 120 nm, 130 nm, 140 nm, 150 nm, 160 nm, 170 nm, 180 nm, 190 nm, 200 nm, or more and 500 units, 1000 units, 1500 units, 2000 units, 2500 units, 3000 units, 3500 units, 4000 units, 4500 units, 5000 units, 5500 units, 6000 units, 7500 units, 8000 units, 8500 units, 9000 units, 9500 units, 10000 units, 11000 nuts, 12000 units, 13000 units, 14000 units, 15000 units, or more of the immune checkpoint expressed on the surface of the extracellular vesicle.

Treatment

Disclosed herein, in some embodiments, are methods of treating a disease or a disorder in a subject, comprising administrating of therapeutic effective amount of the compositions or pharmaceutical compositions described herein to the subject. In some embodiments, the disease or disorder is an autoimmune disease, including Rheumatoid arthritis, Systemic lupus erythematosus, Psoriasis, Type 1 diabetes mellitus, Multiple sclerosis, Inflammatory bowel disease, Celiac disease, Crohn's disease, Graves' disease, Juvenile arthritis, Lyme disease chronic, Optic neuritis, Psoriatic arthritis, Scleritis, Scleroderma, Ulcerative colitis (UC), Uveitis, Inflammatory eye conditions, Vitiligo, COPD, complication from Organ transplantation, or graft-versus-host disease.

In some embodiments, the method comprises steps of: contacting the cell with the compositions or pharmaceutical compositions as described herein; upon said contacting, the immune checkpoint moiety is delivered to the target cell. In some embodiments, the immune checkpoint moiety modulates immune response or of the target cell. In some embodiments, the contacting occurs in vivo, ex vivo, or in vitro. In some embodiment, the composition or pharmaceutical composition can directly be administered to the subject.

In some embodiments, the composition or pharmaceutical composition can be administered to the subject alone (e.g., standalone treatment). In some embodiments, the composition is administered in combination with an additional agent. In some embodiments, the composition is a first-line treatment for the disease or condition. In some embodiments, the composition is a second-line, third-line, or fourth-line treatment, for the autoimmune disease.

In general, methods disclosed herein comprise administering a composition by oral administration. However, in some instances, methods comprise administering a composition by intraperitoneal injection. In some instances, methods comprise administering a composition in the form of an anal suppository. In some instances, methods comprise administering a composition by intravenous ("i.v.") administration. It is conceivable that one can also administer compositions disclosed herein by other routes, such as subcutaneous injection, intramuscular injection, intradermal injection, transdermal injection percutaneous administration, intranasal administration, intralymphatic injection, rectal administration intragastric administration, or any other suitable parenteral administration. In some embodiments, routes for local delivery closer to site of injury or inflammation are preferred over systemic routes. Routes, dosage, time points, and duration of administrating therapeutics can be adjusted. In some embodiments, administration of therapeutics is prior to, or after, onset of either, or both, acute and chronic symptoms of the disease or condition.

An effective dose and dosage of the compositions to prevent or treat the autoimmune diseases herein is defined by an observed beneficial response related to the autoimmune disease or condition, or symptom of the autoimmune disease. In some instances, the beneficial response comprises reduction of symptoms of autoimmune disease. Additional beneficial response comprises preventing, alleviating, arresting, or curing the autoimmune disease. In instances where the composition is not therapeutically effective or is not providing a sufficient alleviation of the disease or condition, or symptom of the disease or condition, then the dosage amount and/or route of administration can be changed, or an additional agent can be administered to the subject, along with the composition. In some embodiments, as a patient is started on a regimen of a composition, the patient is also weaned off (e.g., step-wise decrease in dose) a second treatment regimen.

Suitable dose and dosage administrated to a subject is determined by factors including, but no limited to, the particular composition, disease condition and its severity, the identity (e.g., weight, sex, age) of the subject in need of treatment, and can be determined according to the particular circumstances surrounding the case, including, e.g., the specific agent being administered, the route of administration, the condition being treated, and the subject being treated.

In some embodiments, the administration of the composition is hourly, once every 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours 22 hours, 23 hours, 1 day, 2 days, 3 days, 4 days, 5 days, 6 days, 7 days, 8 days, 9 days, 10 days, 11 days, 12 days, 13 days, 14 days, 15 days, 1 month, 2 months, 3 months, 4 months, 5 months, 6 months, 7 months, 8 months, 9 months, 10 months, 11 months, 1 year, 2 years, 3 years, 4 years, or 5 years, or 10 years. The effective dosage ranges can be adjusted based on subject's response to the treatment. Some routes of administration will require higher concentrations of effective amount of therapeutics than other routes.

In certain embodiments, where the patient's condition does not improve, upon the doctor's discretion the administration of composition is administered chronically, that is, for an extended period of time, including throughout the duration of the patient's life in order to ameliorate or otherwise control or limit the symptoms of the patient's disease or condition. In certain embodiments wherein a patient's status does improve, the dose of composition being administered can be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. In certain embodiments, the dose of drug being administered can be temporarily reduced or temporarily suspended for a certain length of time (i.e., a "drug diversion"). In specific embodiments, the length of the drug diversion is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug diversion is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. After a suitable length of time, the normal dosing schedule is optionally reinstated.

In some embodiments, once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

Toxicity and therapeutic efficacy of such therapeutic regimens are determined by standard pharmaceutical procedures in cell cultures or experimental animals, including, but not limited to, the determination of the LD50 and the ED50. The dose ratio between the toxic and therapeutic effects is the therapeutic index and it is expressed as the ratio between LD50 and ED50. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the composition described herein lies within a range of circulating concentrations that include the ED50 with minimal toxicity. In certain embodiments, the daily dosage range and/or the unit dosage amount varies within this range depending upon the dosage form employed and the route of administration utilized.

A composition can be used alone or in combination with an additional agent. In some cases, an "additional agent" as used herein is administered alone. The composition and the additional agent can be administered together or sequentially. The combination therapies can be administered within the same day, or can be administered one or more days, weeks, months, or years apart. Examples of additional agent can include other immune modulators such as antibodies targeting cytokines or small molecules.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLES

The following illustrative examples are representative of embodiments of the stimulation, systems, and methods described herein and are not meant to be limiting in any way.

Example 1. Mesenchymal Stem Cells (MSCs) and Their Correspondent Extracellular Vesicles (EVs) Comprise PD-L1

Figure 1:
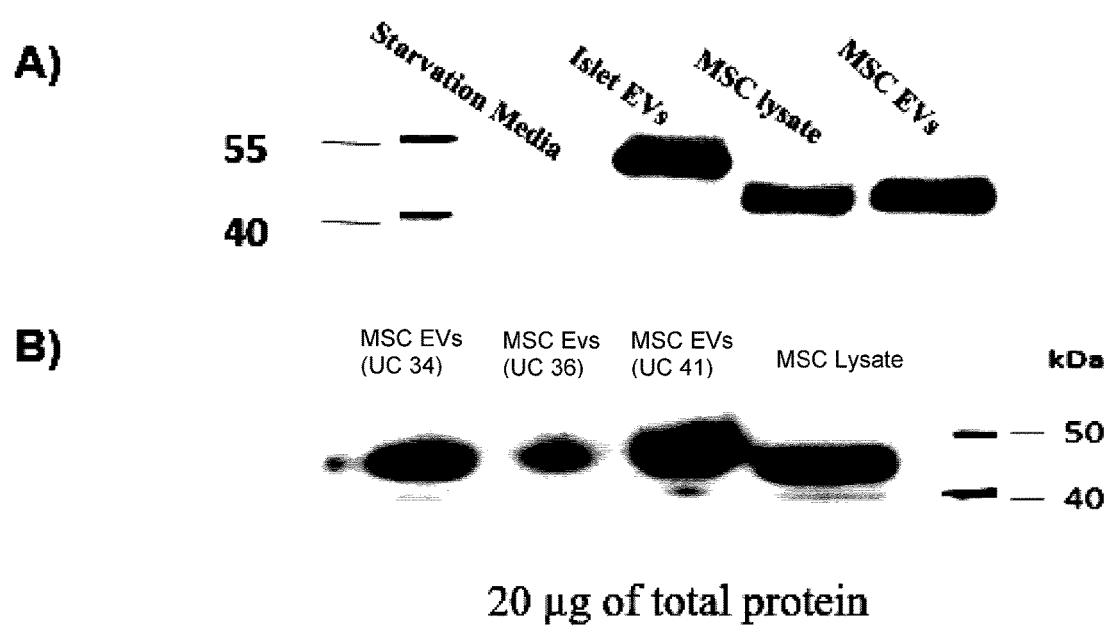
FIG. 1 illustrates proteomics analysis on the human MSC-derived exosomes detecting.

The presence of PD-L1 on MSCs and their correspondent extracellular vesicles was confirmed by western blotting. As shown in FIG. 1, a clear band with size of 45 kDa was detected in MSCs and correspondent exosomes. Starvation media was used as negative control and islet exosomes was used as positive control. To standardize these results, the same assay was performed on the MSC EVs from three different donors of umbilical cord MSCs.

MSC lystate and MSC EV samples were prepared by sonication with volumes of MSC lystate and MSC EV samples corresponding to 25 μg protein. These samples were analyzed using a gradient precast polyacrylamide gel (Mini-PROTEAN; Bio-Rad laboratories, Hercules, CA, USA). The samples were then transferred onto a nitrocellulose membrane which was blocked using 5% blotting grade Blocker Non-Fat Dry Milk (Bio-Rad Laboratories) in Tris-buffer saline (TBS) for 2 h. The membrane was subsequently incubated with primary antibodies against Purified anti-human CD274 (B7-H1, PD-L1) Antibody (Biolegend; cat #329701) in 0.25% blotting grade Blocker Non-Fat Dry Milk in TBS-Tween (TBST) overnight at 4° C. The membrane was then washed with TBST for 10 min, three times. Secondary antibodies ECL anti mouse IgG horseradish peroxidase-linked F(ab')2 fragment diluted in 0.25% blotting grade Blocker Non-Fat Dry Milk in TBST were incubated with the membrane for 1.5 h. The membranes were finally analyzed with ECL Prime Western Blotting Detection (GE Healthcare) and a VersaDoc 4000 MP (Bio-Rad Laboratories).

Example 2. MSC EVs Suppress CD25+CD8+ Immune Cells

Significant CD25+CD8+ immune cell suppression was observed in human peripheral blood mononuclear cells (PBMCs) stimulated with IL-2 (500 U/ml) for 6 days. It was also observed that this suppression was lessened in experimental groups wherein the PBMCs were also contacted with PD-L1 inhibiting antibodies. A schematic for this experiment is represented in FIG. 2.

The representative flow cytometry plots of FIG. 3 show that in the presence of blocking PD-L1, the suppressive activity of MSC EVs towards CD8+CD25+ population significantly decreases. Further, while the control group comprising isotype control antibodies shows the same suppressive activity similar to MSC EVs alone. These results show that suppressive activity of MSC EVs is primarily a function of the presence of PD-L1.

Example 3. MSCs Genetically Modified to Produce More Exosomal PD-L1 than Wildtype MSCs MSCs are harvested from the umbilical cord of healthy donors. Once harvested, these MSCs are cultured for further experimentation. Transmembrane CD63 is targeted for genetic modification by known techniques (e.g. CRISPR/Cas9). The extracellular domain of PD-L1 is fused to CD63. Several specific subsets of the amino acid sequence of CD63 have been identified as particularly advantageous regions of PD-L1 fusion: directly following RDKVMSE; directly following NNNFRQQ; and directly following YPKNNHT. These portions of CD63 are found in the Large Extracellular Loop (LEL) of CD63. 1, 2, 3, or more G45 linkers are used to fuse the extracellular domain of PD-L1 to CD63.

Following genetic modification of the MSCs, the genetically modified MSCS are cultured. Samples of genetically modified MSC lystate and genetically modified MSC EVs are prepared following the protocol of Example 1. These samples are analyzed by western blot analysis to test for the presence of PD-L1. Clear bands with size of 45 kDa are detected in genetically modified MSCs and their correspondent exosomes. These bands are darker in color than the western blot analysis of Example 1, indicating that the genetically modified MSCs and their correspondent exosomes produce more PD-L1 than wildtype MSCs and EVs produced from wildtype MSCs. Starvation media was used as negative control and islet exosomes was used as positive control.

Example 4. MSCs Genetically Modified to Produce Exosomal Immune Checkpoint Inhibitors The method of Example 3 is utilized to transcribe any immune checkpoint inhibitor selected from VISTA, PD-L1, CTLA-4, PD-L2, B7-1 (CD80), B7-2 (CD86), B7-H3 (CD276), B7-H2, B7-H4 (VTCN1), HVEM (CD270, TNFRSF14), Galectin 9, Galectin3, CEACAM1 (CD66a), OX-2 (CD200), PVR (CD155), PVRL2 (Nectin-2, CD112), FGL-1, PECAM-1, TSG-6, CD47, Stabilin-1 (Clever-1), Neuropilin 1, Neuropilin 2, CD158 (family), IGSF2 (CD101), CD155, GITRL, CD137L, OX40L, LIGHT, CD70, PD-1, RGMB, CTLA-4 (CD152), BTLA, CD160, Tim-3, CD200R, TIGIT, CD112R (PVRIG), LAG-3 (CD223), PECAM-1, CD44, SIRP alpha (CD172a), or a combination thereof.

Western blot analysis is conducted on the genetically modified MSCs and their correspondent EVs to test for the presence of the selected immune checkpoint inhibitor.

Example 5. Generation/Purification of Potent Genetically Modified MSCs and Their Correspondent EVs The genetically modified MSCs and their correspondent EVs from Example 3 are assayed to generate potent MSCs and their correspondent EVs sufficient for increased CD25+CD8+ immune cell suppression as compared to the results of Example 2.

The genetically modified MSCs and their correspondent EVs from Example 3 are prepared in a solution comprising anti-PD-L1 antibodies conjugated with detectable labels and soluble PD-1. The soluble PD-1 binds to exosomal PD-L1. Due to the interactions between the soluble PD-1 and the exosomal PD-L1 present on the surface of the MSCs and their correspondent EVs, the anti-PD-L1 antibodies conjugated with detectable labels selectively bind to the MSCs and EVs in the sample that express the higher levels of exosomal PD-L1 as compared to the MSCs and EVs wherein the correspondent exosomal PD-L1 is occupied by the soluble PD-1 present in the sample.

Using this assay, potent MSCs and EVs are generated/purified from the sample.

Example 6. The Potent Genetically Modified MSCs and Their Correspondent EVs Show Enhanced CD25+CD8+ Immune Cell Suppression The potent MSCs and EVs from Example 5 are assayed in the experiment of Example 2. The experimental groups comprising the potent MSCs and EVs show significantly increased CD25+CD8+ immune cell suppression compared to the results of FIG. 3.

Example 7. Potent Genetically Modified MSCs and Their Correspondent EVs for Treatment of Rheumatoid Arthritis Pharmaceutical compositions comprising the potent EVs from Examples 5 and 6 and pharmaceutically acceptable excipients are prepared to treat patients suffering from rheumatoid arthritis. The pharmaceutical compositions comprise between about $10^{1'6}$ to about $10^{^8}$ EVs or between about 1 μg to about 700 mg of EVs.

The pharmaceutical compositions are administered to patients suffering from rheumatoid arthritis at the site of inflammation. The increased CD25+CD8+ immune cell suppression of the EVs is sufficient for treating rheumatoid arthritis.

Example 8. Potent Genetically Modified MSCs and Their Correspondent EVs for Treatment of Graft-versus-Host Disease in a Patient Undergoing a Kidney Transplant Pharmaceutical compositions comprising the potent EVs from Examples 5 and 6 and pharmaceutically acceptable excipients are prepared to treat patients suffering from graft-versus-host disease in a patient undergoing a kidney transplant. The pharmaceutical compositions comprise between about $10^{^6}$ to about $10^{^8}$ EVs or between about 1 μg to about 700 mg of EVs.

The pharmaceutical compositions are administered to patients suffering from graft-versus-host disease in a patient undergoing a kidney transplant at the site of inflammation. The increased CD25+CD8+ immune cell suppression of the EVs is sufficient for treating graft-versus-host disease in a patient undergoing a kidney transplant.

While the foregoing disclosure has been described in some detail for purposes of clarity and understanding, it will be clear to one skilled in the art from a reading of this disclosure that various changes in form and detail can be made without departing from the true scope of the disclosure. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

---

The invention claimed is:

1. A composition comprising a plurality of extracellular vesicles, wherein an extracellular vesicle of the plurality of extracellular vesicles comprises a first immune checkpoint moiety and a second immune checkpoint moiety,
wherein the first immune checkpoint moiety is CD200 and the second immune checkpoint moiety is an extracellular domain of PD-L1,
said extracellular domain of PD-L1 is linked to a transmembrane moiety of the extracellular vesicle,
said transmembrane moiety is different from said second immune checkpoint moiety, and
wherein the second immune checkpoint moiety is exposed on a surface of said extracellular vesicle.

2. The composition of claim 1, wherein a second extracellular vesicle of the plurality of extracellular vesicles comprises a first immune checkpoint moiety coupled to a first transmembrane moiety and a second immune checkpoint moiety coupled to a second transmembrane moiety,
wherein the first immune checkpoint moiety and the second immune checkpoint moieties are different, and
wherein the first and second transmembrane moieties are different from the first and second immune checkpoint moieties.

3. The composition of claim 2, wherein the first transmembrane moiety and the second transmembrane moiety are different.

4. The composition of claim 1, wherein a plurality of immune checkpoint moieties are expressed on the surface of the extracellular vesicle.

5. The composition of claim 1, wherein the CD200 is coupled to a second transmembrane moiety, and the second transmembrane moiety is different from the CD200.

6. The composition of claim 1, wherein the plurality of extracellular vesicles comprises a heterogenous population of extracellular vesicles.

7. The composition of claim 1, wherein a second extracellular vesicle of the plurality of extracellular vesicles comprises a first immune checkpoint moiety and a second immune checkpoint moiety,
wherein the first immune checkpoint moiety is CD200 and the second immune checkpoint moiety is PD-L1.

8. The composition of claim 1, wherein a plurality of immune checkpoint moieties are expressed on the surface of the plurality of extracellular vesicles.

9. The composition of claim 1, wherein the composition is formulated for parenteral administration.

10. The composition of claim 9, wherein the composition is formulated for intravenous administration.

11. The composition of claim 1, wherein the composition is formulated for topical administration.

12. The composition of claim 11, the composition is formulated for topical administration to an eye.

13. The composition of claim 1, wherein the plurality of extracellular vesicles are exosomes.

14. The composition of claim 1, wherein the plurality of extracellular vesicles are derived from a mesenchymal stem cell.

* * * * *

SEQUENCE LISTING

```
<160> NUMBER OF SEQ ID NOS: 21

<210> SEQ ID NO 1
<211> LENGTH: 311
<212> TYPE: PRT
<213> ORGANISM: Homo sapiens

<400> SEQUENCE: 1

Met Gly Val Pro Thr Ala Leu Glu Ala Gly Ser Trp Arg Trp Gly Ser
```

```
                1               5                   10                  15
Leu Leu Phe Ala Leu Phe Leu Ala Ala Ser Leu Gly Pro Val Ala Ala
                20                  25                  30

Phe Lys Val Ala Thr Pro Tyr Ser Leu Tyr Val Cys Pro Glu Gly Gln
                35                  40                  45

Asn Val Thr Leu Thr Cys Arg Leu Leu Gly Pro Val Asp Lys Gly His
                50                  55                  60

Asp Val Thr Phe Tyr Lys Thr Trp Tyr Arg Ser Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
                100                 105                 110

Leu Ala Gln Arg His Gly Leu Glu Ser Ala Ser Asp His His Gly Asn
                115                 120                 125

Phe Ser Ile Thr Met Arg Asn Leu Thr Leu Leu Asp Ser Gly Leu Tyr
                130                 135                 140

Cys Cys Leu Val Val Glu Ile Arg His His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
                180                 185                 190

Ala Ala Ala Leu Ala Thr Gly Ala Cys Ile Val Gly Ile Leu Cys Leu
                195                 200                 205

Pro Leu Ile Leu Leu Leu Val Tyr Lys Gln Arg Gln Ala Ala Ser Asn
                210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
                260                 265                 270

Glu Ser Gly Arg His Leu Leu Ser Glu Pro Ser Thr Pro Leu Ser Pro
                275                 280                 285

Pro Gly Pro Gly Asp Val Phe Phe Pro Ser Leu Asp Pro Val Pro Asp
                290                 295                 300

Ser Pro Asn Phe Glu Val Ile
305                 310

<210> SEQ ID NO 2
<211> LENGTH: 290
<212> TYPE: PRT
<213> ORGANISM: Homo sapiens

<400> SEQUENCE: 2

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
                35                  40                  45

Asp Leu Ala Ala Leu Ile Val Tyr Trp Glu Met Glu Asp Lys Asn Ile
                50                  55                  60
```

```
Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 3
<211> LENGTH: 223
<212> TYPE: PRT
<213> ORGANISM: Homo sapiens

<400> SEQUENCE: 3

Met Ala Cys Leu Gly Phe Gln Arg His Lys Ala Gln Leu Asn Leu Ala
  1               5                  10                  15

Thr Arg Thr Trp Pro Cys Thr Leu Leu Phe Phe Leu Leu Phe Ile Pro
                 20                  25                  30

Val Phe Cys Lys Ala Met His Val Ala Gln Pro Ala Val Val Leu Ala
             35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
 65                  70                  75                  80

Val Thr Glu Val Cys Ala Ala Thr Tyr Met Met Gly Asn Glu Leu Thr
                 85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140
```

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
            195                 200                 205

Pro Glu Cys Glu Lys Gln Phe Gln Pro Tyr Phe Ile Pro Ile Asn
            210                 215                 220

<210> SEQ ID NO 4
<211> LENGTH: 410
<212> TYPE: PRT
<213> ORGANISM: Homo sapiens

<400> SEQUENCE: 4

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
                20                  25                  30

Leu Thr Asp Ser Glu Asn Ala Thr Cys Leu Tyr Ala Lys Trp Gln Met
            35                  40                  45

Asn Phe Thr Val Arg Tyr Glu Thr Thr Asn Lys Thr Tyr Lys Thr Val
        50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
                100                 105                 110

Ser Val Ser Phe Ser Tyr Asn Thr Gly Asp Asn Thr Thr Phe Pro Asp
            115                 120                 125

Ala Glu Asp Lys Gly Ile Leu Thr Val Asp Glu Leu Leu Ala Ile Arg
            130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
                180                 185                 190

Lys Thr Ser Thr Val Ala Pro Thr Ile His Thr Thr Val Pro Ser Pro
            195                 200                 205

Thr Thr Thr Pro Thr Pro Lys Glu Lys Pro Glu Ala Gly Thr Tyr Ser
            210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
            275                 280                 285

Lys Asn Glu Asn Arg Phe Tyr Leu Lys Glu Val Asn Ile Ser Met Tyr

```
                290                 295                 300
Leu Val Asn Gly Ser Val Phe Ser Ile Ala Asn Asn Leu Ser Tyr
305                 310                 315                 320

Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
                340                 345                 350

Gln Pro Phe Asn Val Thr Gln Gly Lys Tyr Ser Thr Ala Gln Asp Cys
                355                 360                 365

Ser Ala Asp Asp Asn Phe Leu Val Pro Ile Ala Val Gly Ala Ala
370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410

<210> SEQ ID NO 5
<211> LENGTH: 238
<212> TYPE: PRT
<213> ORGANISM: Homo sapiens

<400> SEQUENCE: 5

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
                20                  25                  30

Val Gly Ala Gln Leu Val Leu Ser Gln Thr Ile Ile Gln Gly Ala Thr
                35                  40                  45

Pro Gly Ser Leu Leu Pro Val Val Ile Ala Val Gly Val Phe Leu
50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
                100                 105                 110

Ser Glu Phe Asn Asn Asn Phe Arg Gln Gln Met Glu Asn Tyr Pro Lys
                115                 120                 125

Asn Asn His Thr Ala Ser Ile Leu Asp Arg Met Gln Ala Asp Phe Lys
130                 135                 140

Cys Cys Gly Ala Ala Asn Tyr Thr Asp Trp Glu Lys Ile Pro Ser Met
145                 150                 155                 160

Ser Lys Asn Arg Val Pro Asp Ser Cys Cys Ile Asn Val Thr Val Gly
                165                 170                 175

Cys Gly Ile Asn Phe Asn Glu Lys Ala Ile His Lys Glu Gly Cys Val
                180                 185                 190

Glu Lys Ile Gly Gly Trp Leu Arg Lys Asn Val Leu Val Val Ala Ala
                195                 200                 205

Ala Ala Leu Gly Ile Ala Phe Val Glu Val Leu Gly Ile Val Phe Ala
210                 215                 220

Cys Cys Leu Val Lys Ser Ile Arg Ser Gly Tyr Glu Val Met
225                 230                 235

<210> SEQ ID NO 6
<211> LENGTH: 119
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
                20                  25                  30

Val Gly Ala Gln Leu Val Leu Ser Gln Thr Ile Ile Gln Gly Ala Thr
            35                  40                  45

Pro Gly Ser Leu Leu Pro Val Val Ile Ile Ala Val Gly Val Phe Leu
        50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
                100                 105                 110

Ser Glu Gly Gly Gly Gly Ser
        115
```

<210> SEQ ID NO 7
<211> LENGTH: 339
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
                20                  25                  30

Val Gly Ala Gln Leu Val Leu Ser Gln Thr Ile Ile Gln Gly Ala Thr
            35                  40                  45

Pro Gly Ser Leu Leu Pro Val Val Ile Ile Ala Val Gly Val Phe Leu
        50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
                100                 105                 110

Ser Glu Gly Gly Gly Gly Ser Phe Thr Val Thr Val Pro Lys Asp Leu
        115                 120                 125

Tyr Val Val Glu Tyr Gly Ser Asn Met Thr Ile Glu Cys Lys Phe Pro
    130                 135                 140

Val Glu Lys Gln Leu Asp Leu Ala Ala Leu Ile Val Tyr Trp Glu Met
145                 150                 155                 160

Glu Asp Lys Asn Ile Ile Gln Phe Val His Gly Glu Glu Asp Leu Lys
                165                 170                 175

Val Gln His Ser Ser Tyr Arg Gln Arg Ala Arg Leu Leu Lys Asp Gln
            180                 185                 190
```

Leu Ser Leu Gly Asn Ala Ala Leu Gln Ile Thr Asp Val Lys Leu Gln
            195                 200                 205

Asp Ala Gly Val Tyr Arg Cys Met Ile Ser Tyr Gly Ala Asp Tyr
        210                 215                 220

Lys Arg Ile Thr Val Lys Val Asn Ala Pro Tyr Asn Lys Ile Asn Gln
225                 230                 235                 240

Arg Ile Leu Val Val Asp Pro Val Thr Ser Glu His Glu Leu Thr Cys
                245                 250                 255

Gln Ala Glu Gly Tyr Pro Lys Ala Glu Val Ile Trp Thr Ser Ser Asp
            260                 265                 270

His Gln Val Leu Ser Gly Lys Thr Thr Thr Thr Asn Ser Lys Arg Glu
        275                 280                 285

Glu Lys Leu Phe Asn Val Thr Ser Thr Leu Arg Ile Asn Thr Thr Thr
    290                 295                 300

Asn Glu Ile Phe Tyr Cys Thr Phe Arg Arg Leu Asp Pro Glu Glu Asn
305                 310                 315                 320

His Thr Ala Glu Leu Val Ile Pro Glu Leu Pro Leu Ala His Pro Pro
                325                 330                 335

Asn Glu Arg

<210> SEQ ID NO 8
<211> LENGTH: 129
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Gly Gly Gly Gly Ser Gly Gly Gly Gly Ser Gly Gly Gly Gly
        115                 120                 125

Ser

<210> SEQ ID NO 9
<211> LENGTH: 349
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Ile Ile Ala Gly Val Phe Leu
50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Gly Gly Gly Ser Gly Gly Gly Ser Gly Gly Gly
            115                 120                 125

Ser Phe Thr Val Thr Val Pro Lys Asp Leu Tyr Val Glu Tyr Gly
        130                 135                 140

Ser Asn Met Thr Ile Glu Cys Lys Phe Pro Val Glu Lys Gln Leu Asp
145                 150                 155                 160

Leu Ala Ala Leu Ile Val Tyr Trp Glu Met Glu Asp Lys Asn Ile Ile
                165                 170                 175

Gln Phe Val His Gly Glu Glu Asp Leu Lys Val Gln His Ser Ser Tyr
            180                 185                 190

Arg Gln Arg Ala Arg Leu Leu Lys Asp Gln Leu Ser Leu Gly Asn Ala
        195                 200                 205

Ala Leu Gln Ile Thr Asp Val Lys Leu Gln Asp Ala Gly Val Tyr Arg
210                 215                 220

Cys Met Ile Ser Tyr Gly Gly Ala Asp Tyr Lys Arg Ile Thr Val Lys
225                 230                 235                 240

Val Asn Ala Pro Tyr Asn Lys Ile Asn Gln Arg Ile Leu Val Val Asp
                245                 250                 255

Pro Val Thr Ser Glu His Glu Leu Thr Cys Gln Ala Glu Gly Tyr Pro
            260                 265                 270

Lys Ala Glu Val Ile Trp Thr Ser Ser Asp His Gln Val Leu Ser Gly
        275                 280                 285

Lys Thr Thr Thr Thr Asn Ser Lys Arg Glu Glu Lys Leu Phe Asn Val
290                 295                 300

Thr Ser Thr Leu Arg Ile Asn Thr Thr Thr Asn Glu Ile Phe Tyr Cys
305                 310                 315                 320

Thr Phe Arg Arg Leu Asp Pro Glu Glu Asn His Thr Ala Glu Leu Val
                325                 330                 335

Ile Pro Glu Leu Pro Leu Ala His Pro Pro Asn Glu Arg
            340                 345

<210> SEQ ID NO 10
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly

```
                    20                  25                  30
Val Gly Ala Gln Leu Val Leu Ser Gln Thr Ile Ile Gln Gly Ala Thr
            35                  40                  45

Pro Gly Ser Leu Leu Pro Val Val Ile Ile Ala Val Gly Val Phe Leu
        50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Val Met Ser Glu Phe Asn Asn Asn Phe Arg Gln Gln Gly Gly
        115                 120                 125

Gly Gly Ser
    130

<210> SEQ ID NO 11
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
                20                  25                  30

Val Gly Ala Gln Leu Val Leu Ser Gln Thr Ile Ile Gln Gly Ala Thr
            35                  40                  45

Pro Gly Ser Leu Leu Pro Val Val Ile Ile Ala Val Gly Val Phe Leu
        50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Val Met Ser Glu Phe Asn Asn Asn Phe Arg Gln Gln Gly Gly
        115                 120                 125

Gly Gly Ser Phe Thr Val Thr Val Pro Lys Asp Leu Tyr Val Val Glu
    130                 135                 140

Tyr Gly Ser Asn Met Thr Ile Glu Cys Lys Phe Pro Val Glu Lys Gln
145                 150                 155                 160

Leu Asp Leu Ala Ala Leu Ile Val Tyr Trp Glu Met Glu Asp Lys Asn
                165                 170                 175

Ile Ile Gln Phe Val His Gly Glu Glu Asp Leu Lys Val Gln His Ser
            180                 185                 190

Ser Tyr Arg Gln Arg Ala Arg Leu Leu Lys Asp Gln Leu Ser Leu Gly
        195                 200                 205

Asn Ala Ala Leu Gln Ile Thr Asp Val Lys Leu Gln Asp Ala Gly Val
    210                 215                 220

Tyr Arg Cys Met Ile Ser Tyr Gly Gly Ala Asp Tyr Lys Arg Ile Thr
225                 230                 235                 240
```

```
Val Lys Val Asn Ala Pro Tyr Asn Lys Ile Asn Gln Arg Ile Leu Val
                245                 250                 255

Val Asp Pro Val Thr Ser Glu His Glu Leu Thr Cys Gln Ala Glu Gly
            260                 265                 270

Tyr Pro Lys Ala Glu Val Ile Trp Thr Ser Ser Asp His Gln Val Leu
            275                 280                 285

Ser Gly Lys Thr Thr Thr Thr Asn Ser Lys Arg Glu Glu Lys Leu Phe
        290                 295                 300

Asn Val Thr Ser Thr Leu Arg Ile Asn Thr Thr Thr Asn Glu Ile Phe
305                 310                 315                 320

Tyr Cys Thr Phe Arg Arg Leu Asp Pro Glu Glu Asn His Thr Ala Glu
                325                 330                 335

Leu Val Ile Pro Glu Leu Pro Leu Ala His Pro Pro Asn Glu Arg
                340                 345                 350

<210> SEQ ID NO 12
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
                100                 105                 110

Ser Glu Val Met Ser Glu Phe Asn Asn Asn Phe Arg Gln Gln Gly Gly
            115                 120                 125

Gly Gly Ser Gly Gly Gly Gly Ser Gly Gly Gly Gly Ser
        130                 135                 140

<210> SEQ ID NO 13
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45
```

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
                100                 105                 110

Ser Glu Val Met Ser Glu Phe Asn Asn Asn Phe Arg Gln Gln Gly Gly
                115                 120                 125

Gly Gly Ser Gly Gly Gly Ser Gly Gly Gly Ser Phe Thr Val
        130                 135                 140

Thr Val Pro Lys Asp Leu Tyr Val Val Glu Tyr Gly Ser Asn Met Thr
145                 150                 155                 160

Ile Glu Cys Lys Phe Pro Val Glu Lys Gln Leu Asp Leu Ala Ala Leu
                165                 170                 175

Ile Val Tyr Trp Glu Met Glu Asp Lys Asn Ile Ile Gln Phe Val His
                180                 185                 190

Gly Glu Glu Asp Leu Lys Val Gln His Ser Ser Tyr Arg Gln Arg Ala
                195                 200                 205

Arg Leu Leu Lys Asp Gln Leu Ser Leu Gly Asn Ala Ala Leu Gln Ile
210                 215                 220

Thr Asp Val Lys Leu Gln Asp Ala Gly Val Tyr Arg Cys Met Ile Ser
225                 230                 235                 240

Tyr Gly Gly Ala Asp Tyr Lys Arg Ile Thr Val Lys Val Asn Ala Pro
                245                 250                 255

Tyr Asn Lys Ile Asn Gln Arg Ile Leu Val Val Asp Pro Val Thr Ser
                260                 265                 270

Glu His Glu Leu Thr Cys Gln Ala Glu Gly Tyr Pro Lys Ala Glu Val
                275                 280                 285

Ile Trp Thr Ser Ser Asp His Gln Val Leu Ser Gly Lys Thr Thr Thr
                290                 295                 300

Thr Asn Ser Lys Arg Glu Glu Lys Leu Phe Asn Val Thr Ser Thr Leu
305                 310                 315                 320

Arg Ile Asn Thr Thr Thr Asn Glu Ile Phe Tyr Cys Thr Phe Arg Arg
                325                 330                 335

Leu Asp Pro Glu Glu Asn His Thr Ala Glu Leu Val Ile Pro Glu Leu
                340                 345                 350

Pro Leu Ala His Pro Pro Asn Glu Arg
                355                 360

<210> SEQ ID NO 14
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
                20                  25                  30

Val Gly Ala Gln Leu Val Leu Ser Gln Thr Ile Ile Gln Gly Ala Thr
                35                  40                  45

```
Pro Gly Ser Leu Leu Pro Val Ile Ile Ala Val Gly Val Phe Leu
    50                  55                  60

Phe Leu Val Ala Phe Val Gly Cys Cys Gly Ala Cys Lys Glu Asn Tyr
 65                  70                  75                  80

Cys Leu Met Ile Thr Phe Ala Ile Phe Leu Ser Leu Ile Met Leu Val
                 85                  90                  95

Glu Val Ala Ala Ala Ile Ala Gly Tyr Val Phe Arg Asp Lys Val Met
                100                 105                 110

Ser Glu Val Met Ser Glu Phe Asn Asn Asn Phe Arg Gln Gln Met Glu
            115                 120                 125

Asn Tyr Pro Lys Asn Asn His Thr Gly Gly Gly Ser
    130                 135                 140

<210> SEQ ID NO 15
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Ala Val Glu Gly Gly Met Lys Cys Val Lys Phe Leu Leu Tyr Val
 1               5                  10                  15

Leu Leu Leu Ala Phe Cys Ala Cys Ala Val Gly Leu Ile Ala Val Gly
                20                  25                  30

Val Gly Ala Gln Leu Val Leu Ser Gln Thr Ile Ile Gln Gly Ala Thr
                35                  40                  45

Pro Gly Ser Leu Leu Pro Val Val Ile Ile Ala Val Gly Val Phe Leu
    50                  55                  60

Phe Leu Val Ala Phe Val Gly Cys Cys Gly Ala Cys Lys Glu Asn Tyr
 65                  70                  75                  80

Cys Leu Met Ile Thr Phe Ala Ile Phe Leu Ser Leu Ile Met Leu Val
                 85                  90                  95

Glu Val Ala Ala Ala Ile Ala Gly Tyr Val Phe Arg Asp Lys Val Met
                100                 105                 110

Ser Glu Val Met Ser Glu Phe Asn Asn Asn Phe Arg Gln Gln Met Glu
            115                 120                 125

Asn Tyr Pro Lys Asn Asn His Thr Gly Gly Gly Ser Phe Thr Val
    130                 135                 140

Thr Val Pro Lys Asp Leu Tyr Val Val Glu Tyr Gly Ser Asn Met Thr
145                 150                 155                 160

Ile Glu Cys Lys Phe Pro Val Glu Lys Gln Leu Asp Leu Ala Ala Leu
                165                 170                 175

Ile Val Tyr Trp Glu Met Glu Asp Lys Asn Ile Ile Gln Phe Val His
                180                 185                 190

Gly Glu Glu Asp Leu Lys Val Gln His Ser Ser Tyr Arg Gln Arg Ala
            195                 200                 205

Arg Leu Leu Lys Asp Gln Leu Ser Leu Gly Asn Ala Ala Leu Gln Ile
    210                 215                 220

Thr Asp Val Lys Leu Gln Asp Ala Gly Val Tyr Arg Cys Met Ile Ser
225                 230                 235                 240

Tyr Gly Gly Ala Asp Tyr Lys Arg Ile Thr Val Lys Val Asn Ala Pro
                245                 250                 255

Tyr Asn Lys Ile Asn Gln Arg Ile Leu Val Val Asp Pro Val Thr Ser
```

```
                    260                 265                 270
Glu His Glu Leu Thr Cys Gln Ala Glu Gly Tyr Pro Lys Ala Glu Val
                275                 280                 285

Ile Trp Thr Ser Ser Asp His Gln Val Leu Ser Gly Lys Thr Thr Thr
            290                 295                 300

Thr Asn Ser Lys Arg Glu Lys Leu Phe Asn Val Thr Ser Thr Leu
305                 310                 315                 320

Arg Ile Asn Thr Thr Asn Glu Ile Phe Tyr Cys Thr Phe Arg Arg
                325                 330                 335

Leu Asp Pro Glu Glu Asn His Thr Ala Glu Leu Val Ile Pro Glu Leu
                340                 345                 350

Pro Leu Ala His Pro Pro Asn Glu Arg
            355                 360

<210> SEQ ID NO 16
<211> LENGTH: 151
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45

Pro Gly Ser Leu Leu Pro Val Val Ile Ala Val Gly Val Phe Leu
    50                  55                  60

Phe Leu Val Ala Phe Val Gly Cys Cys Gly Ala Cys Lys Glu Asn Tyr
65                  70                  75                  80

Cys Leu Met Ile Thr Phe Ala Ile Phe Leu Ser Leu Ile Met Leu Val
                85                  90                  95

Glu Val Ala Ala Ala Ile Ala Gly Tyr Val Phe Arg Asp Lys Val Met
            100                 105                 110

Ser Glu Val Met Ser Glu Phe Asn Asn Asn Phe Arg Gln Gln Met Glu
        115                 120                 125

Asn Tyr Pro Lys Asn Asn His Thr Gly Gly Gly Ser Gly Gly Gly
    130                 135                 140

Gly Ser Gly Gly Gly Gly Ser
145                 150

<210> SEQ ID NO 17
<211> LENGTH: 371
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Ala Val Glu Gly Gly Met Lys Cys Val Lys Phe Leu Leu Tyr Val
1               5                   10                  15

Leu Leu Leu Ala Phe Cys Ala Cys Ala Val Gly Leu Ile Ala Val Gly
            20                  25                  30

Val Gly Ala Gln Leu Val Leu Ser Gln Thr Ile Ile Gln Gly Ala Thr
        35                  40                  45
```

```
                35                  40                  45
        Pro Gly Ser Leu Leu Pro Val Ile Ile Ala Val Gly Val Phe Leu
            50                  55                  60

Phe Leu Val Ala Phe Val Gly Cys Cys Gly Ala Cys Lys Glu Asn Tyr
        65                  70                  75                  80

Cys Leu Met Ile Thr Phe Ala Ile Phe Leu Ser Leu Ile Met Leu Val
                        85                  90                  95

Glu Val Ala Ala Ile Ala Gly Tyr Val Phe Arg Asp Lys Val Met
                    100                 105                 110

Ser Glu Val Met Ser Glu Phe Asn Asn Phe Arg Gln Gln Met Glu
                    115                 120                 125

Asn Tyr Pro Lys Asn Asn His Thr Gly Gly Gly Ser Gly Gly Gly
                    130                 135                 140

Gly Ser Gly Gly Gly Ser Phe Thr Val Thr Val Pro Lys Asp Leu
        145                 150                 155                 160

Tyr Val Val Glu Tyr Gly Ser Asn Met Thr Ile Glu Cys Lys Phe Pro
                        165                 170                 175

Val Glu Lys Gln Leu Asp Leu Ala Ala Leu Ile Val Tyr Trp Glu Met
                    180                 185                 190

Glu Asp Lys Asn Ile Ile Gln Phe Val His Gly Glu Glu Asp Leu Lys
                    195                 200                 205

Val Gln His Ser Ser Tyr Arg Gln Arg Ala Arg Leu Leu Lys Asp Gln
                    210                 215                 220

Leu Ser Leu Gly Asn Ala Ala Leu Gln Ile Thr Asp Val Lys Leu Gln
        225                 230                 235                 240

Asp Ala Gly Val Tyr Arg Cys Met Ile Ser Tyr Gly Gly Ala Asp Tyr
                        245                 250                 255

Lys Arg Ile Thr Val Lys Val Asn Ala Pro Tyr Asn Lys Ile Asn Gln
                    260                 265                 270

Arg Ile Leu Val Val Asp Pro Val Thr Ser Glu His Glu Leu Thr Cys
                    275                 280                 285

Gln Ala Glu Gly Tyr Pro Lys Ala Glu Val Ile Trp Thr Ser Ser Asp
                    290                 295                 300

His Gln Val Leu Ser Gly Lys Thr Thr Thr Thr Asn Ser Lys Arg Glu
        305                 310                 315                 320

Glu Lys Leu Phe Asn Val Thr Ser Thr Leu Arg Ile Asn Thr Thr Thr
                        325                 330                 335

Asn Glu Ile Phe Tyr Cys Thr Phe Arg Arg Leu Asp Pro Glu Glu Asn
                    340                 345                 350

His Thr Ala Glu Leu Val Ile Pro Glu Leu Pro Leu Ala His Pro Pro
                    355                 360                 365

Asn Glu Arg
            370

<210> SEQ ID NO 18
<211> LENGTH: 7
<212> TYPE: PRT
<213> ORGANISM: Homo sapiens

<400> SEQUENCE: 18

Arg Asp Lys Val Met Ser Glu
1               5

<210> SEQ ID NO 19
<211> LENGTH: 7
```

```
<212> TYPE: PRT
<213> ORGANISM: Homo sapiens

<400> SEQUENCE: 19

Asn Asn Asn Phe Arg Gln Gln
1               5

<210> SEQ ID NO 20
<211> LENGTH: 7
<212> TYPE: PRT
<213> ORGANISM: Homo sapiens

<400> SEQUENCE: 20

Tyr Pro Lys Asn Asn His Thr
1               5

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(15)
<223> OTHER INFORMATION: This sequence may encompass 1-3 "Gly Gly Gly
      Gly Ser" repeating units
<220> FEATURE:
<223> OTHER INFORMATION: See specification as filed for detailed
      description of substitutions and preferred embodiments

<400> SEQUENCE: 21

Gly Gly Gly Gly Ser Gly Gly Gly Gly Ser Gly Gly Gly Gly Ser
1               5                   10                  15
```